United States Patent
Allan et al.

(10) Patent No.: US 9,834,513 B2
(45) Date of Patent: *Dec. 5, 2017

(54) BENZYLAMINE DERIVATIVES

(71) Applicant: KALVISTA PHARMACEUTICALS LIMITED, Salisbury (GB)

(72) Inventors: Christine Elizabeth Allan, Eastleigh (GB); Andrzej Roman Batt, Southampton (GB); Rebecca Louise Davie, Salisbury (GB); Hannah Joy Edwards, Salisbury (GB); David Michael Evans, Salisbury (GB); Stephen John Pethen, Salisbury (GB)

(73) Assignee: Kalvista Pharmceuticals Limited, Salisbury, England (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/602,688

(22) Filed: May 23, 2017

(65) Prior Publication Data

US 2017/0253561 A1    Sep. 7, 2017

Related U.S. Application Data

(63) Continuation of application No. 14/759,542, filed as application No. PCT/GB2014/050043 on Jan. 8, 2014, now Pat. No. 9,670,157.

(60) Provisional application No. 61/750,074, filed on Jan. 8, 2013, provisional application No. 61/865,732, filed on Aug. 14, 2013.

(30) Foreign Application Priority Data

Jan. 8, 2013   (GB) .................................. 1300304.1

(51) Int. Cl.
```
C07D 207/34      (2006.01)
C07D 231/14      (2006.01)
C07D 417/14      (2006.01)
C07D 417/06      (2006.01)
C07D 413/06      (2006.01)
C07D 409/14      (2006.01)
C07D 409/06      (2006.01)
C07D 403/10      (2006.01)
C07D 401/14      (2006.01)
C07D 401/10      (2006.01)
C07D 401/06      (2006.01)
C07D 249/10      (2006.01)
```

(52) U.S. Cl.
CPC ......... C07D 207/34 (2013.01); C07D 231/14 (2013.01); C07D 249/10 (2013.01); C07D 401/06 (2013.01); C07D 401/10 (2013.01); C07D 401/14 (2013.01); C07D 403/10 (2013.01); C07D 409/06 (2013.01); C07D 409/14 (2013.01); C07D 413/06 (2013.01); C07D 417/06 (2013.01); C07D 417/14 (2013.01)

(58) Field of Classification Search
CPC .. C07D 207/37; C07D 401/14; C07D 401/06; C07D 401/10; C07D 231/14; C07D 403/10; C07D 409/06; C07D 409/14; C07D 413/06; C07D 417/06; C07D 417/14; C07D 249/10

See application file for complete search history.

(56) References Cited

U.S. PATENT DOCUMENTS

| 5,187,157 A | 2/1993 | Kettner et al. |
| 7,101,878 B1 | 9/2006 | Anderson et al. |
| 8,207,378 B2 | 6/2012 | Steinmetzer et al. |

FOREIGN PATENT DOCUMENTS

| EP | 1568698 A1 | 8/2005 |
| EP | 2281885 A1 | 2/2011 |
| WO | WO9204371 A1 | 3/1992 |
| WO | WO9429335 A1 | 12/1994 |
| WO | WO9507921 A1 | 3/1995 |
| WO | WO03076458 A2 | 9/2003 |
| WO | WO2004062657 A1 | 7/2004 |
| WO | WO2005123680 A1 | 12/2005 |
| WO | WO2006114313 A1 | 11/2006 |

(Continued)

OTHER PUBLICATIONS

Kenniston, J Bio Chem, vol. 289 (34), 23596-23608, 2014.*
Bryant, Cardiovasc Hematol Agents Med Chem, vol. 7(3), 234-250, 2009.*
Prassas, Nature Reviews Drug Discovery, vol. 14, 183-202, 2015.*
Babu, "Drug Discovery at BioCryst Pharmaceuticals Inc.", Presentation, http://files.shareholder.com/downloads/BCRX/0x0x403076/97a18d6e-1621-4fc6-8f5fd0828bddab4f/, Sep. 16, 2010, 18 pages.
Caddick et al., "Convenient Synthesis of Protected Primary Amines from Nitriles", Tetrahedron Letters, Apr. 29, 2000, 41(18), 3513-3516.

(Continued)

*Primary Examiner* — D M Seaman
(74) *Attorney, Agent, or Firm* — Baker & Hostetler LLP

(57) ABSTRACT

The present invention provides compounds of formula (I):

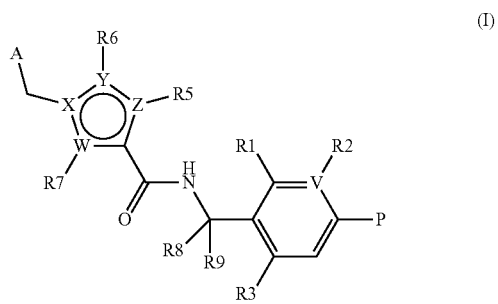

compositions comprising such compounds; the use of such compounds in therapy (for example in the treatment or prevention of a disease or condition in which plasma kallikrein activity is implicated); and methods of treating patients with such compounds; wherein R1 to R3, R5 to R9, A, P, V, W, X, Y and Z are as defined herein.

26 Claims, No Drawings

(56) References Cited

FOREIGN PATENT DOCUMENTS

| | | |
|---|---|---|
| WO | WO2008016883 A2 | 2/2008 |
| WO | WO2008049595 A1 | 5/2008 |
| WO | WO2009097141 A1 | 8/2009 |
| WO | WO2009106980 A2 | 9/2009 |
| WO | WO2009114677 A1 | 9/2009 |
| WO | WO2011075684 A1 | 6/2011 |
| WO | WO2011094496 A2 | 8/2011 |
| WO | WO2011118672 A1 | 9/2011 |
| WO | WO2012004678 A2 | 1/2012 |
| WO | WO2012017020 A1 | 2/2012 |
| WO | WO2012142308 A1 | 10/2012 |
| WO | WO2012174362 A1 | 12/2012 |
| WO | WO2013111107 A1 | 8/2013 |
| WO | WO2013111108 A1 | 8/2013 |
| WO | WO2014108406 A1 | 7/2014 |

OTHER PUBLICATIONS

Chilcote et al., "ASP-634: An Oral Drug Candidate for Diabetic MacularEdema", ARVO 2012 May 6-May 9, 2012, Fort Lauderdale, Florida, (Presentation 2240), 1 page.

Clermont et al., "Plasma Kallikrein Mediates Retinal Vascular Dysfunction and Induces Retinal Thickening in Diabetic Rats", Diabetes, May 2011, 60, 1590-1598.

Elman et al., "Randomized Trial Evaluating Ranibizumab Plus Prompt or Deferred Laser or Triamcinolone Plus Prompt Laser for Diabetic Macular Edema", Opthalmology, Jun. 2010, 117(6), 1064-1077.

Evans et al., "Selective Inhibitors of Plasma Kallikrein", Immunolpharmocology, 1996, 32, 115-116.

Garrett et al., "Peptide Aldehyde Inhibitors of the Kallikreins: An Investigation of Subsite Interactions with Tripeptides Containing Structural Variations at the Amino Terminus", J. Peptide Res., 1998, 52, 62-71.

Griesbacher et al., "Involvement of Tissue Kallikrein But Not Plasma Kallikrein in the Development of Symptoms Mediated by Endogenous Kinins in Acute Pancreatitis in Rats", British Journal of Pharmacology, 2002, 137, 692-700.

Johansen et al., "Assay of Kallikrein Inhibitors and Levels of Acetone-Activated Kallikrein in Plasma Specimens from Reactors to Dextran or to Contrast Media", International Journal Tissue Reactions, 1986, 8, 185-192.

Kolte et al., "Biochemical Characterization of a Novel High-Affinity and Specific Plasma Kallikrein Inhibitor", British Journal of Pharmacology, Nov. 25, 2010, 162, 1639-1649.

Lehmann, "Ecallantide (DX-88), a Plasma Kallikrein Inhibitor for the Treatment of Hereditary Angioedema and the Prevention of Blood Loss in On-Pump Cardiothoracic Surgery", Expert Opinion Biol. Ther., Aug. 2008, 8, 1187-1199.

Leinweber, "Possible Physiological Roles of Carboxylic Ester Hydrolases", Drug Metabolism Reviews, 1987, 18(4), 379-439.

Liang et al., "Fast-Dissolving Intraoral Drug Delivery Systems", Expert Opinion in Therapeutic Patents, 2001, 11(6), 981-986.

Lieberman et al., "Pharmaceutical Dosage Forms: Tablets", Marcel Dekker, 1980, 2, 15 pages.

Marceau et al., "Bradykinin Receptor Ligands: Therapeutic Perspectives", Nature Review, Drug Discovery 2004, Oct. 2004, 3, 845-852.

Okada et al., "Development of Potent and Selective Plasmin and Plasma Kallikrein Inhibitors and Studies on the Structure-Activity Relationship", Chem. Pharm. Bull., 2000, 48, 12, 1964-1972.

Remington's Pharmaceutical Sciences, 19th Edition, Gennaro, Mack Publishing Company, 1995, 5 pages.

Shori et al., "New Specific Assays for Tonin and Tissue Kallikrein Activities in Rat Submandibular Glands: Assays Reveal Differences in the Effects of Sympathetic and Parasympathetic Stimulation on Proteinases in Saliva", Biochemical Pharmacology, Mar. 17, 1992, 43(6), 1209-1217.

Stahl et al., "Handbook of Pharmaceutical Salts: Properties, Selection and Use", Wiley-VCH, Weinheim, Germany, 2002, 1 page.

Stürzbecher et al., "Novel Plasma Kallikrein Inhibitors of the Benzamidine Type", Brazilian J. med. Biol. Res., 1994, 27, 1929-1934.

Stürzebecher et al., "Inhibition of Human Mast Cell Tryptase by Benzamidine Derivatives", Biological Chemistry Hoppe-Seyler, Oct. 1992, 373(2), 1025-1030.

Teno et al., "Development of Active Center-Directed Plasmin and Plasma Kallikrein Inhibitors and Studies on the Structure-Inhibitory Activity Relationship", Chem. Pharm. Bull., Jun. 1993, 41, 1079-1090.

Wermuth, "The Practice of Medicinal Chemistry", 2nd Edition, 2003, 561-585.

Young et al., "Small Molecule Inhibitors of Plasma Kallikrein", Bioorg. Med. Chem. Letts., Apr. 2006, 16, 7, 2034-2036.

Zhang et al., "Discovery of Highly Potent Small Molecule Kallikrein Inhibitors", Medicinal Chemistry 2, 2006, 545-553.

Björkqvist et al., "Plasma kallikrein: the bradykinin-producing enzyme", Thrombosis and Haemotasis, 2013, 110, 399-407.

Bryant et al., "Human plasma kallikrein-kinin system: Physiological and biochemical parameters", Cardiovascular & Hematological Agents in Medicinal Chemistry, Jul. 2009, 7(3), 234-250.

Clermont et al., "Plasma Kallikrein Mediates Retinal Vascular Dysfunction and Induces Retinal Thickening in Diabetic Rats", Diabetes, 2011, 1-9.

Colman, "Plasma and tissue kallikrein in arthritis and inflammatory bowel disease", Immunopharmology, 1999, 43, 103-108.

Davis III et al., "Biological activities of C1 inhibitor", Molecular Immunology, 2008, 45, 4057-4063.

Feener at al., "Role of plasma kallikrein in diabetes and metabolism", Thrombosis and Haemostasis, Sep. 2013, 110(3), 434-441.

Ikeda et al., "Host Stromal Bradykinin B2 Receptor Signaling Facilitates Tumor-Associated Angiogenesis and Tumor Growth", Cancer Research, Aug. 2004, 64, 5178-5185.

Jaffa et al., "Plasma Prekallikrein A Risk Marker for Hypertension and Nephropathy in Type 1 Diabetes", Diabetes, May 2003, vol. 52, 1215-1221.

Katsuura et al., "Effects of a Highly Selective Synthetic Inhibitor of Plasma Kallikrein on Disseminated Intravascular Coagulation in Rats", Thrombosis Research, 1996, vol. 82, No. 4, 361-368.

Lehmann, "Escallantide (DX-88), a plasma kallikrein inhibitor for the treatment of hereditary angioedema and the prevention of blood loss in on-pump cardiothoracic surgery", Expert Opinion on Biological Therapy, 2008, 8(8), 1187-1199.

Siebeck et al., "Inhibition of Plasma Kallikrein With Aprotinin in Porcine Endotoxin Shock", The Journal of Trauma, 1993, vol. 34, No. 2, 193-198.

Tombran-Tink et al., "Opthamology Research", Visual Dysfunction in Diabetes The Science of Patient Impairment and Health Care, 2012, 4 pages.

Luthin et al., "The Discovery of Novel Small Molecule Non-peptide Gonadotropin Releasing Hormone (GnRH) Receptor Antagonists" Bioorg Med Chem Lett, 12, 2002, pp. 3467-3470.

\* cited by examiner

BENZYLAMINE DERIVATIVES

CROSS-REFERENCE TO RELATED APPLICATIONS

This application is a continuation of U.S. patent application Ser. No. 14/759,542, filed Jul. 7, 2015, which is the National Stage of International Patent Application No. PCT/GB2014/050043 filed Jan. 8, 2014, which claims the benefit of Great Britain Patent Application No. 1300304.1, filed Jan. 8, 2013; U.S. Provisional Patent Application No. 61/750,074, filed Jan. 8, 2013; and U.S. Provisional Patent Application No. 61/865,732, filed Aug. 14, 2013, the disclosures of which are incorporated herein by reference in their entireties.

TECHNICAL FIELD

This invention relates to benzylamine derivatives and to pharmaceutical compositions containing and the uses of, such derivatives.

BACKGROUND

The benzylamine derivatives of the present invention are inhibitors of plasma kallikrein and have a number of therapeutic applications, particularly in the treatment of retinal vascular permeability associated with diabetic retinopathy and diabetic macular edema.

Plasma kallikrein is a trypsin-like serine protease that can liberate kinins from kininogens (see K. D. Bhoola et al., "Kallikrein-Kinin Cascade", *Encyclopedia of Respiratory Medicine*, p 483-493; J. W. Bryant et al., "Human plasma kallikrein-kinin system: physiological and biochemical parameters" *Cardiovascular and haematological agents in medicinal chemistry*, 7, p 234-250, 2009; K. D. Bhoola et al., *Pharmacological Rev.*, 1992, 44, 1; and D. J. Campbell, "Towards understanding the kallikrein-kinin system: insights from the measurement of kinin peptides", *Brazilian Journal of Medical and Biological Research* 2000, 33, 665-677). It is an essential member of the intrinsic blood coagulation cascade although its role in this cascade does not involve the release of bradykinin or enzymatic cleavage. Plasma prekallikrein is encoded by a single gene and synthesized in the liver. It is secreted by hepatocytes as an inactive plasma prekallikrein that circulates in plasma as a heterodimer complex bound to high molecular weight kininogen which is activated to give the active plasma kallikrein. Kinins are potent mediators of inflammation that act through G protein-coupled receptors and antagonists of kinins (such as bradykinin antagonists) have previously been investigated as potential therapeutic agents for the treatment of a number of disorders (F. Marceau and D. Regoli, Nature Rev., Drug Discovery, 2004, 3, 845-852).

Plasma kallikrein is thought to play a role in a number of inflammatory disorders. The major inhibitor of plasma kallikrein is the serpin C1 esterase inhibitor. Patients who present with a genetic deficiency in C1 esterase inhibitor suffer from hereditary angioedema (HAE) which results in intermittent swelling of face, hands, throat, gastro-intestinal tract and genitals. Blisters formed during acute episodes contain high levels of plasma kallikrein which cleaves high molecular weight kininogen liberating bradykinin leading to increased vascular permeability. Treatment with a large protein plasma kallikrein inhibitor has been shown to effectively treat HAE by preventing the release of bradykinin which causes increased vascular permeability (A. Lehmann "Ecallantide (DX-88), a plasma kallikrein inhibitor for the treatment of hereditary angioedema and the prevention of blood loss in on-pump cardiothoracic surgery" *Expert Opin. Biol. Ther.* 8, p 1187-99).

The plasma kallikrein-kinin system is abnormally abundant in patients with advanced diabetic macular edema. It has been recently published that plasma kallikrein contributes to retinal vascular dysfunctions in diabetic rats (A. Clermont et al. "Plasma kallikrein mediates retinal vascular dysfunction and induces retinal thickening in diabetic rats" *Diabetes*, 2011, 60, p 1590-98). Furthermore, administration of the plasma kallikrein inhibitor ASP-440 ameliorated both retinal vascular permeability and retinal blood flow abnormalities in diabetic rats. Therefore a plasma kallikrein inhibitor should have utility as a treatment to reduce retinal vascular permeability associated with diabetic retinopathy and diabetic macular edema.

Other complications of diabetes such as cerebral haemorrhage, nephropathy, cardiomyopathy and neuropathy, all of which have associations with plasma kallikrein may also be considered as targets for a plasma kallikrein inhibitor.

Synthetic and small molecule plasma kallikrein inhibitors have been described previously, for example by Garrett et al. ("Peptide aldehyde . . . " *J. Peptide Res.* 52, p 62-71 (1998)), T. Griesbacher et al. ("Involvement of tissue kallikrein but not plasma kallikrein in the development of symptoms mediated by endogenous kinins in acute pancreatitis in rats" *British Journal of Pharmacology* 137, p 692-700 (2002)), Evans ("Selective dipeptide inhibitors of kallikrein" WO03/076458), Szelke et al. ("Kininogenase inhibitors" WO92/04371), D. M. Evans et al. (*Immunolpharmacology*, 32, p 115-116 (1996)), Szelke et al. ("Kininogen inhibitors" WO95/07921), Antonsson et al. ("New peptides derivatives" WO94/29335), J. Corte et al. ("Six membered heterocycles useful as serine protease inhibitors" WO2005/123680), J. Stürzbecher et al. (*Brazilian J. Med. Biol. Res* 27, p 1929-34 (1994)), Kettner et al. (U.S. Pat. No. 5,187,157), N. Teno et al. (*Chem. Pharm. Bull.* 41, p 1079-1090 (1993)), W. B. Young et al. ("Small molecule inhibitors of plasma kallikrein" *Bioorg. Med. Chem. Letts.* 16, p 2034-2036 (2006)), Okada et al. ("Development of potent and selective plasmin and plasma kallikrein inhibitors and studies on the structure-activity relationship" *Chem. Pharm. Bull.* 48, p 1964-72 (2000)), Steinmetzer et al. ("Trypsin-like serine protease inhibitors and their preparation and use" WO08/049595), Zhang et al. ("Discovery of highly potent small molecule kallikrein inhibitors" *Medicinal Chemistry* 2, p 545-553 (2006)), Sinha et al. ("Inhibitors of plasma kallikrein" WO08/016883), Shigenaga et al. ("Plasma Kallikrein Inhibitors" WO2011/118672), and Kolte et al. ("Biochemical characterization of a novel high-affinity and specific kallikrein inhibitor", British Journal of Pharmacology (2011), 162(7), 1639-1649). Also, Steinmetzer et al. ("Serine protease inhibitors" WO2012/004678) describes cyclized peptide analogs which are inhibitors of human plasmin and plasma kallikrein.

To date, no small molecule synthetic plasma kallikrein inhibitor has been approved for medical use. The molecules described in the known art suffer from limitations such as poor selectivity over related enzymes such as KLK1, thrombin and other serine proteases, and poor oral availability. The large protein plasma kallikrein inhibitors present risks of anaphylactic reactions, as has been reported for Ecallantide. Thus there remains a need for compounds that selectively inhibit plasma kallikrein, that do not induce anaphylaxis and that are orally available. Furthermore, the vast majority of molecules in the known art feature a highly polar and ionisable guanidine or amidine functionality. It is well known that such functionalities may be limiting to gut permeability and therefore to oral availability. For example, it has been reported by Tamie J. Chilcote and Sukanto Sinha ("ASP-634: An Oral Drug Candidate for Diabetic Macular Edema", ARVO 2012 May 6-May 9, 2012, Fort Lauderdale, Fla., Presentation 2240) that ASP-440, a benzamidine, suffers from poor oral availability. It is further reported that absorption may be improved by creating a prodrug such as ASP-634. However, it is well known that prodrugs can suffer from several drawbacks, for example, poor chemical stability and potential toxicity from the inert carrier or from unexpected metabolites.

There are only few reports of plasma kallikrein inhibitors that do not feature guanidine or amidine functionalities. For example, BioCryst Pharmaceuticals Inc. have reported the discovery of BCX4161 which is a benzylamine derivative (http://files.shareholder.com/downloads/BCRX/ 0x0x403076/97a18d6e-1621-4fc6-8f5f-d0828bddab4f/ Dr._Yarlagadda_S._Babu_Ph.D._Drug_Discovery.pdf). Data relating to its oral exposure in the rat are reported in their Second Quarter 2012 Financial Results & Corporate Update. Oral efficacy in a rat model is reported but at the relatively high dose of 100 mg/kg. Another example is Brandl et al. ("N-((6-amino-pyridin-3-yl)methyl)-heteroaryl-carboxamides as inhibitors of plasma kallikrein" WO2012/017020), which describes compounds that feature an amino-pyridine functionality. Oral efficacy in a rat model is demonstrated at relatively high doses of 30 mg/kg and 100 mg/kg but the pharmacokinetic profile is not reported. Thus it is not yet known whether such compounds will provide sufficient oral availability or efficacy for progression to the clinic.

Therefore there remains a need to develop new plasma kallikrein inhibitors that will have utility to treat a wide range of disorders, in particular to reduce retinal vascular permeability associated with diabetic retinopathy and diabetic macular edema. Preferred compounds will possess a good pharmacokinetic profile and in particular will be suitable as drugs for oral delivery.

SUMMARY OF THE INVENTION

The present invention relates to a series of benzylamine derivatives that are inhibitors of plasma kallikrein. These compounds demonstrate good selectivity for plasma kallikrein and are potentially useful in the treatment of impaired visual acuity, diabetic retinopathy, macular edema, hereditary angioedema, diabetes, pancreatitis, cerebral haemorrhage, nephropathy, cardiomyopathy, neuropathy, inflammatory bowel disease, arthritis, inflammation, septic shock, hypotension, cancer, adult respiratory distress syndrome, disseminated intravascular coagulation, cardiopulmonary bypass surgery and bleeding from post operative surgery. The invention further relates to pharmaceutical compositions of the inhibitors, to the use of the compositions as therapeutic agents, and to methods of treatment using these compositions.

In an aspect, the present invention provides compounds of formula I

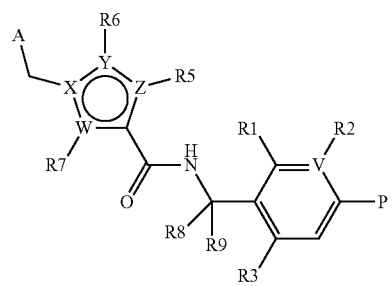

Formula (I)

wherein,

V is selected from C and N such that the aromatic ring containing V is phenyl or pyridine;

R2 is absent when V is N; or, when present, R2 is selected from H, alkyl, alkoxy, CN, halo and $CF_3$;

R1 and R3 are independently selected from H, alkyl, alkoxy, CN, halo and $CF_3$;

W, X, Y and Z are independently selected from C, N, O and S, such that the ring containing W, X, Y and Z is a five-membered aromatic heterocycle;

wherein,

R5, R6 and R7 are independently absent or independently selected from H, alkyl, halo, aryl, heteroaryl and $CF_3$;

P is —C(R10)(R11)$NH_2$;

R8 and R9 are independently selected from H and alkyl, or may together form a cycloalkyl ring;

R10 and R11 are independently selected from H and alkyl, or may together form a cycloalkyl ring or a cyclic ether;

A is selected from N-linked morpholine, aryl, heteroaryl, alkyl is a linear saturated hydrocarbon having up to 10 carbon atoms ($C_1$-$C_{10}$) or a branched saturated hydrocarbon of between 3 and 10 carbon atoms ($C_3$-$C_{10}$); alkyl may optionally be substituted with 1 or 2 substituents independently selected from ($C_1$-$C_6$)alkoxy, OH, CN, $CF_3$, —COOR12, —CONR12R13, H($CH_2$)$_{1-3}$CON(R12) ($CH_2$)$_{1-3}$—, fluoro and —NR12R13;

cycloalkyl is a monocyclic saturated hydrocarbon of between 3 and 7 carbon atoms; wherein cycloalkyl may be optionally substituted with a substituent selected from alkyl, alkoxy and NR12R13;

a cyclic ether is a monocyclic saturated hydrocarbon of between 4 and 7 carbon atoms, wherein one of the ring carbons is replaced by an oxygen atom;

alkoxy is a linear O-linked hydrocarbon of between 1 and 6 carbon atoms ($C_1$-$C_6$) or a branched O-linked hydrocarbon of between 3 and 6 carbon atoms ($C_3$-$C_6$); alkoxy may optionally be substituted with 1 or 2 substituents independently selected from aryl, OH, CN, $CF_3$, —COOR12, —CONR12R13, fluoro and NR12R13;

aryl is phenyl, biphenyl or naphthyl; aryl may be optionally substituted with 1, 2 or 3 substituents independently selected from alkyl, alkoxy, OH, halo, CN, -morpholinyl, -piperidinyl, heteroaryl, aryl[b], —O-aryl[b], —($CH_2$)$_{1-3}$-aryl[b], —($CH_2$)$_{1-3}$-heteroaryl, —COOR12, —CONR12R13, —($CH_2$)$_{1-3}$—NR14R15, $CF_3$ and NR12R13;

aryl[b] is phenyl, biphenyl or naphthyl, which may be optionally substituted with 1, 2 or 3 substituents independently selected from alkyl, alkoxy, OH, halo, CN, morpholinyl, piperidinyl, —COOR12, —CONR12R13, $CF_3$ and NR12R13;

heteroaryl is a 5, 6, 9 or 10 membered mono- or bi-cyclic aromatic ring, containing, where possible, 1, 2 or 3 ring members independently selected from N, NR12, S and O;

heteroaryl may be optionally substituted with 1, 2 or 3 substituents independently selected from alkyl, alkoxy, OH, halo, CN, morpholinyl, piperidinyl, aryl, —(CH$_2$)$_{1-3}$-aryl, heteroaryl$^b$, —COOR12, —CONR12R13, CF$_3$ and NR12R13;

heteroaryl$^b$ is a 5, 6, 9 or 10 membered mono- or bi-cyclic aromatic ring, containing, where possible, 1, 2 or 3 ring members independently selected from N, NR12, S and O; wherein heteroaryl$^b$ may be optionally substituted with 1, 2 or 3 substituents independently selected from alkyl, alkoxy, OH, halo, CN, morpholinyl, piperidinyl, aryl, —(CH$_2$)$_{1-3}$-aryl, —COOR12, —CONR12R13, CF$_3$ and NR12R13;

R12 and R13 are independently selected from H and alkyl; or R12 and R13 together with the nitrogen to which they are attached form a 4-, 5-, 6- or 7-membered heterocyclic ring which may be saturated or unsaturated with 1 or 2 double bonds;

R14 and R15 together with the nitrogen to which they are attached form a 4-, 5-, 6- or 7-membered heterocyclic ring which may be saturated or unsaturated with 1 or 2 double bonds, and optionally may be oxo substituted;

wherein, when R5, R6 and R7 are absent or H, then:

either

R10 and R11 together form a cycloalkyl ring or a cyclic ether;

or

A is aryl and aryl is phenyl, biphenyl or naphthyl substituted with 1, 2 or 3 substituents independently selected from OH, heteroaryl, aryl$^b$, —(CH$_2$)$_{1-3}$-aryl$^b$, —(CH$_2$)$_{1-3}$-heteroaryl, —COOR12, —CONR12R13, and —(CH$_2$)$_3$-NR14R15; wherein, aryl$^b$ is phenyl, biphenyl or naphthyl, wherein aryl$^b$ is substituted with 1, 2 or 3 substituents independently selected from alkyl, alkoxy, OH, halo, CN, morpholinyl, piperidinyl, —COOR12, —CONR12R13, CF$_3$ and NR12R13; and heteroaryl is a 5, 6, 9 or 10 membered mono- or bi-cyclic aromatic ring, containing, where possible, 1, 2 or 3 ring members independently selected from N, NR12, S and O, wherein heteroaryl is substituted with 1, 2 or 3 substituents independently selected from alkyl, alkoxy, halo, CN, aryl, morpholinyl, piperidinyl, —(CH$_2$)$_{1-3}$-aryl, heteroaryl$^b$, —COOR12, —CONR12R13, CF$_3$ and —NR12R13;

or

A is heteroaryl and heteroaryl is a 5, 6, 9 or 10 membered mono- or bi-cyclic aromatic ring, containing, where possible, 1, 2 or 3 ring members independently selected from N, NR12, S and O, wherein heteroaryl is substituted with 1, 2 or 3 substituents independently selected from aryl, —(CH$_2$)$_{1-3}$-aryl, heteroaryl$^b$, —COOR12, and —CONR12R13;

wherein, aryl is phenyl, biphenyl or naphthyl, wherein aryl is substituted with 1, 2 or 3 substituents independently selected from alkyl, alkoxy, OH, halo, CN, morpholinyl, piperidinyl, heteroaryl, aryl$^b$, —O-aryl$^b$, —(CH$_2$)$_{1-3}$-aryl$^b$, —(CH$_2$)$_{1-3}$-heteroaryl, —COOR12, —CONR12R13, —COR12R13, —(CH$_2$)$_{1-3}$—NR14R15, CF$_3$ and —NR12R13; and heteroaryl$^b$ is a 5, 6, 9 or 10 membered mono- or bi-cyclic aromatic ring, containing, where possible, 1, 2 or 3 ring members independently selected from N, NR12, S and O, wherein heteroaryl$^b$ is substituted with 1, 2 or 3 substituents independently selected from alkyl, alkoxy, halo, CN, morpholinyl, piperidinyl, aryl, —(CH$_2$)$_{1-3}$-aryl, —COOR12, —CONR12R13, CF$_3$ and NR12R13;

and tautomers, isomers, stereoisomers (including enantiomers, diastereoisomers and racemic and scalemic mixtures thereof), pharmaceutically acceptable salts and solvates thereof.

In another aspect the present invention provides a prodrug of a compound of formula (I) as herein defined, or a pharmaceutically acceptable salt thereof.

In yet another aspect the present invention provides an N-oxide of a compound of formula (I) as herein defined, or a prodrug or pharmaceutically acceptable salt thereof.

It will be understood that certain compounds of the present invention may exist in solvated, for example hydrated, as well as unsolvated forms. It is to be understood that the present invention encompasses all such solvated forms.

In an aspect the invention comprises a subset of the compounds of formula (I):

$$\text{(I)}$$

wherein A, W, X, Y, Z, V, P, R1, R2, R3, R5, R6, R7, R8 and R9 are as defined above, with the proviso that at least one of R5, R6 and R7 must be present and be independently selected from alkyl, halo, aryl, heteroaryl and CF$_3$;

and tautomers, isomers, stereoisomers (including enantiomers, diastereoisomers and racemic and scalemic mixtures thereof), pharmaceutically acceptable salts and solvates thereof.

In an aspect, the invention comprises a subset of the compounds of formula (I) wherein:

R1 is H, F, Cl, CF$_3$, OCH$_3$ or CH$_3$;

R2 is H or F if V is C; or R2 is absent if V is N; and

R3 is H or CH$_3$;

and tautomers, isomers, stereoisomers (including enantiomers, diastereoisomers and racemic and scalemic mixtures thereof), pharmaceutically acceptable salts and solvates thereof.

In another aspect, the invention comprises a subset of the compounds of formula (I) wherein:

W is C;

X is N;

Y is C;

Z is C;

R5 is H;

R6 and R7 are CH$_3$;

R8 and R9 are H; and

R10 and R11 are both H or together form a cyclopropane ring;

and tautomers, isomers, stereoisomers (including enantiomers, diastereoisomers and racemic and scalemic mixtures thereof), pharmaceutically acceptable salts and solvates thereof.

In another aspect, the invention comprises a subset of the compounds of formula (I) wherein:

W is C;
X is N;
Y is C;
Z is C;
R5 is H;
R6 and R7 are CH₃;
R8 and R9 are both H;
R10 and R11 are both H or together form a cyclopropane ring; and
A is selected from:

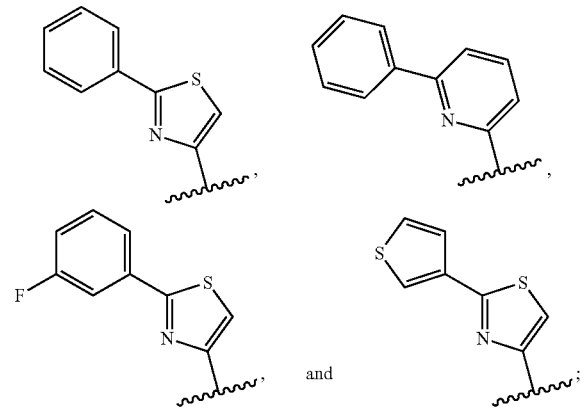

and tautomers, isomers, stereoisomers (including enantiomers, diastereoisomers and racemic and scalemic mixtures thereof), pharmaceutically acceptable salts and solvates thereof.

In another aspect, the invention comprises a subset of the compounds of formula (I) wherein:
R1 is H, F, Cl, CF₃, OCH₃ or CH₃;
R2 is H or F if V is C; or R2 is absent if V is N; and
R3 is H or CH₃;
W is C;
X is N;
Y is C;
Z is C;
R5 is H;
R6 and R7 are CH₃;
R8 and R9 are both H;
R10 and R11 are both H or together form a cyclopropane ring; and
A is selected from:

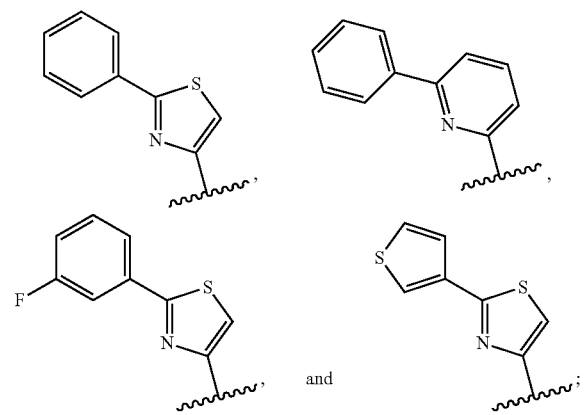

and tautomers, isomers, stereoisomers (including enantiomers, diastereoisomers and racemic and scalemic mixtures thereof), pharmaceutically acceptable salts and solvates thereof.

In another aspect, the invention comprises a subset of the compounds of formula (I) wherein:
V is C;
R1 is H or CH₃;
R2 is H or F;
R3 is H or CH₃;
W, X, Y and Z are independently selected from C and N, such that the ring containing W, X, Y and Z is a five-membered aromatic heterocycle;
R5, R6 and R7 are independently absent, or are independently selected from H and alkyl;
R8 and R9 are both H;
R10 and R11 together form a cyclopropane ring; and
A is selected from:

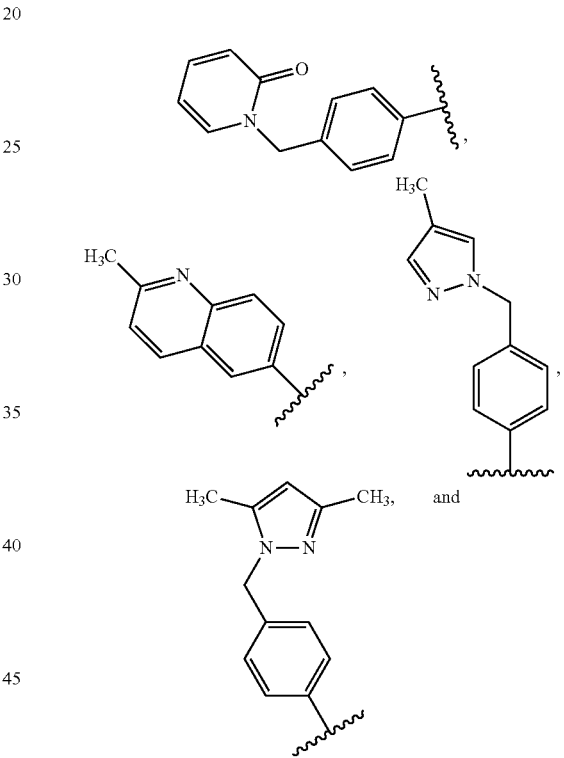

In another aspect, the invention comprises a subset of the compounds of formula (I) wherein:
V is C;
R1 is H or CH₃;
R2 is H;
R3 is H or CH₃;
W, X, Y and Z are independently selected from C and N, such that the ring containing W, X, Y and Z is a five-membered aromatic heterocycle;

R5, R6 and R7 are independently absent, or are independently selected from H, alkyl, halo, aryl, heteroaryl and CF$_3$;

R8 and R9 are both H;

R10 and R11 are both H or together form a cyclopropane ring; and

A is selected from:

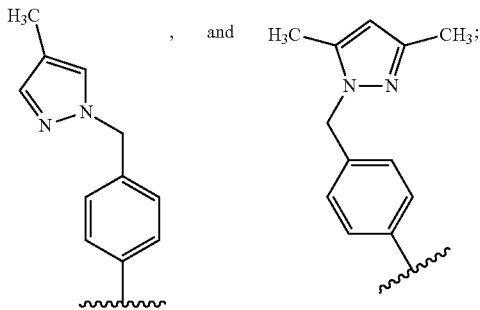

and tautomers, isomers, stereoisomers (including enantiomers, diastereoisomers and racemic and scalemic mixtures thereof), pharmaceutically acceptable salts and solvates thereof.

In another aspect, the invention comprises a subset of the compounds of formula (I) wherein A is selected from:

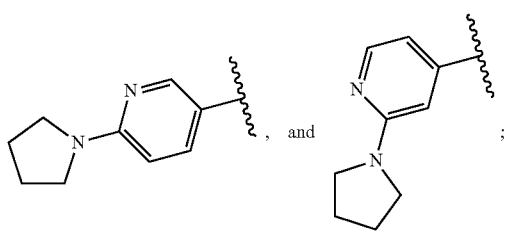 [SMILES: *c1ccc(N2CCCC2)nc1 ; *c1ccnc(N2CCCC2)c1]

In an aspect, the invention comprises compounds of formula (II):

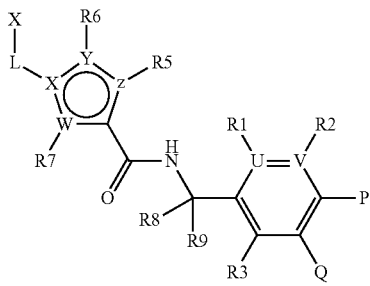

Formula (II)

wherein,

U and V are independently selected from C and N such that the aromatic ring containing U and V is phenyl, pyridine or pyrazine;

R1 is absent when U is N;

R2 is absent when V is N;

or, when present, R1 and R2 are independently selected from H, alkyl, alkoxy, CN, halo and CF$_3$;

R3 is selected from H, alkyl, alkoxy, CN, halo and CF$_3$;

W, X, Y and Z are independently selected from C, N, O and S, such that the five-membered ring containing W, X, Y and Z is an aromatic heterocycle;

R5, R6 and R7 are independently absent, or are independently selected from H, alkyl, halo, aryl, heteroaryl and CF$_3$;

or, optionally, when Y and/or Z is C, R5 and R6 may together form an aromatic ring, optionally containing 1 or 2 atoms selected from N, O or S, fused to the five-membered heterocyclic aromatic ring containing W, X, Y and Z; wherein the resulting aromatic fused bicycle may be optionally mono-, di- or tri-substituted with a substituent selected from alkyl, alkoxy, OH, halo, CN, —COOR12, —CONR12R13, CF$_3$ and NR12R13;

P and Q are, independently, H or —C(R10)(R11)NH$_2$;

R8 and R9 are independently selected from H and alkyl, or may together form a cycloalkyl ring;

R10 and R11 are independently selected from H and alkyl, or may together form a cycloalkyl ring or a cyclic ether;

L is a linker selected from a covalent bond, —(CH$_2$)$_{1-10}$—, —O—(CH$_2$)$_{2-10}$—, —(CH$_2$)$_{1-10}$—O—(CH$_2$)$_{1-10}$—, —(CH$_2$)$_{1-10}$—NH—(CH$_2$)$_{1-10}$—, —CONH—(CH$_2$)$_{1-10}$—, —CO—, and —SO$_2$—;

A is selected from N-linked morpholine, aryl, and heteroaryl;

alkyl is a linear saturated hydrocarbon having up to 10 carbon atoms (C$_1$-C$_{10}$) or a branched saturated hydrocarbon of between 3 and 10 carbon atoms (C$_3$-C$_{10}$); alkyl may optionally be substituted with 1 or 2 substituents independently selected from (C$_1$-C$_6$)alkoxy, OH, CN, CF$_3$, —COOR12, —CONR12R13, H(CH$_2$)$_{1-3}$CON(R12)(CH$_2$)$_{1-3}$—, fluoro and —NR12R13;

cycloalkyl is a monocyclic saturated hydrocarbon of between 3 and 7 carbon atoms; wherein cycloalkyl may be optionally substituted with a substituent selected from alkyl, alkoxy and NR12R13;

a cyclic ether is a monocyclic saturated hydrocarbon of between 4 and 7 carbon atoms, wherein one of the ring carbons is replaced by an oxygen atom;

alkoxy is a linear O-linked hydrocarbon of between 1 and 6 carbon atoms (C$_1$-C$_6$) or a branched O-linked hydrocarbon of between 3 and 6 carbon atoms (C$_3$-C$_6$); alkoxy may optionally be substituted with 1 or 2 substituents independently selected from aryl, OH, CN, CF$_3$, —COOR12, —CONR12R13, fluoro and NR12R13;

aryl is phenyl, biphenyl or naphthyl; aryl may be optionally substituted with 1, 2 or 3 substituents independently selected from alkyl, alkoxy, OH, halo, CN, -morpholinyl, -piperidinyl, heteroaryl, aryl$^b$, —O-aryl$^b$, —(CH$_2$)$_{1-3}$-aryl$^b$, —(CH$_2$)$_{1-3}$-heteroaryl, —COOR12, —CONR12R13, —COR14R15, —(CH$_2$)$_{1-3}$—NR14R15, CF$_3$ and NR12R13;

aryl$^b$ is phenyl, biphenyl or naphthyl, which may be optionally substituted with 1, 2 or 3 substituents independently selected from alkyl, alkoxy, OH, halo, CN, morpholinyl, piperidinyl, —COOR12, —CONR12R13, CF$_3$ and NR12R13;

heteroaryl is a 5, 6, 9 or 10 membered mono- or bi-cyclic aromatic ring, containing, where possible, 1, 2 or 3 ring members independently selected from N, NR12, S and O; heteroaryl may be optionally substituted with 1, 2 or 3 substituents independently selected from alkyl, alkoxy, OH, halo, CN, morpholinyl, piperidinyl, aryl, —(CH$_2$)$_{1-3}$-aryl, heteroaryl$^b$, —COOR12, —CONR12R13, CF$_3$ and NR12R13;

heteroaryl$^b$ is a 5, 6, 9 or 10 membered mono- or bi-cyclic aromatic ring, containing, where possible, 1, 2 or 3 ring members independently selected from N, NR12, S and O; wherein heteroaryl$^b$ may be optionally substituted with 1, 2 or 3 substituents independently selected from alkyl, alkoxy, OH, halo, CN, morpholinyl, piperidinyl, aryl, —(CH$_2$)$_{1-3}$-aryl, —COOR12, —CONR12R13, CF$_3$ and NR12R13;

R12 and R13 are independently selected from H and alkyl;

R14 and R15 together with the nitrogen to which they are attached form a 4-, 5-, 6- or 7-membered heterocyclic ring which may be saturated or unsaturated with 1 or 2 double bonds, and optionally may be oxo substituted;

wherein,
when R5, R6 and R7 are absent or H, then:
either
R10 and R11 together form a cycloalkyl ring or a cyclic ether;
or
A is aryl and aryl is phenyl, biphenyl or naphthyl substituted with 1, 2 or 3 substituents independently selected from OH, heteroaryl, aryl$^b$, —O-aryl$^b$, —(CH$_2$)$_{1-3}$-aryl$^b$, —(CH$_2$)$_{1-3}$-heteroaryl, —COOR12, —CONR12R13, and —(CH$_2$)$_3$—NR14R15; wherein, aryl$^b$ is phenyl, biphenyl or naphthyl, wherein aryl$^b$ is substituted with 1, 2 or 3 substituents independently selected from alkyl, alkoxy, OH, halo, CN, morpholinyl, piperidinyl, —COOR12, —CONR12R13, CF$_3$ and NR12R13; and heteroaryl is a 5, 6, 9 or 10 membered mono- or bi-cyclic aromatic ring, containing, where possible, 1, 2 or 3 ring members independently selected from N, NR12, S and O, wherein heteroaryl is substituted with 1, 2 or 3 substituents independently selected from alkyl, alkoxy, halo, CN, aryl, morpholinyl, piperidinyl, —(CH$_2$)$_{1-3}$-aryl, heteroaryl$^b$, —COOR12, —CONR12R13, CF$_3$ and —NR12R13;

or
A is heteroaryl and heteroaryl is a 5, 6, 9 or 10 membered mono- or bi-cyclic aromatic ring, containing, where possible, 1, 2 or 3 ring members independently selected from N, NR12, S and O, wherein heteroaryl is substituted with 1, 2 or 3 substituents independently selected from aryl, —(CH$_2$)$_{1-3}$-aryl, heteroaryl$^b$, —COOR12, and —CONR12R13;

wherein,
aryl is phenyl, biphenyl or naphthyl, wherein aryl is substituted with 1, 2 or 3 substituents independently selected from alkyl, alkoxy, OH, halo, CN, morpholinyl, piperidinyl, heteroaryl, aryl$^b$, —O-aryl$^b$, —(CH$_2$)$_{1-3}$-aryl$^b$, —(CH$_2$)$_{1-3}$-heteroaryl, —COOR12, —CONR12R13, —COR12R13, —(CH$_2$)$_{1-3}$—NR14R15, CF$_3$ and —NR12R13; and heteroaryl$^b$ is a 5, 6, 9 or 10 membered mono- or bi-cyclic aromatic ring, containing, where possible, 1, 2 or 3 ring members independently selected from N, NR12, S and O, wherein heteroaryl$^b$ is substituted with 1, 2 or 3 substituents independently selected from alkyl, alkoxy, halo, CN, morpholinyl, piperidinyl, aryl, —(CH$_2$)$_{1-3}$-aryl, —COOR12, —CONR12R13, CF$_3$ and NR12R13;

and tautomers, isomers, stereoisomers (including enantiomers, diastereoisomers and racemic and scalemic mixtures thereof), pharmaceutically acceptable salts and solvates thereof.

The present invention also comprises the following aspects and combinations thereof:

V is selected from C and N such that the aromatic ring containing V is phenyl or pyridine.

In an embodiment, V is N such that the aromatic ring containing V is pyridine.

In an embodiment, V is C such that the aromatic ring containing V is phenyl.

In a preferred embodiment U is C.

R2 is absent when V is N.

R1 and, when present, R2 are independently selected from H, alkyl, alkoxy, CN, halo and CF$_3$.

In an embodiment, R1 and, when present, R2 are independently selected from H, alkyl, alkoxy, halo and CF$_3$.

In an embodiment, R1 and, when present, R2 are independently selected from H, methyl, methoxy, Cl, F and CF$_3$.

In an embodiment, R1 is selected from H, methyl, methoxy, Cl, F and CF$_3$.

In an embodiment, R1 is selected from alkyl, alkoxy, CN, halo and CF$_3$.

In a preferred embodiment, R1 is selected from H and methyl.

In a more preferred embodiment, R1 is H.

In an embodiment, when present, R2 is selected from H, methyl, methoxy, and F.

In a preferred embodiment, when present, R2 is H.

R3 is selected from H, alkyl, alkoxy, CN, halo and CF$_3$;

In an embodiment, R3 is selected from H and alkyl.

In an embodiment, R3 is selected from H and methyl.

In a more preferred embodiment, R3 is H.

In an embodiment, when R2 is present, R1 is selected from H, methyl, methoxy, Cl, F and CF$_3$; R2 is H; and R3 is selected from H and methyl.

In an embodiment, R2 is present and R1, R2 and R3 are H.

In an embodiment, R1 and R3 are methyl.

In an embodiment, when R2 is present, R1 and R3 are methyl; and R2 is H.

In a preferred embodiment, R1 is methyl.

W, X, Y and Z are independently selected from C, N, O and S, such that the ring containing W, X, Y and Z is a five-membered aromatic heterocycle.

In an embodiment, W, X, Y and Z are independently selected from C and N, such that the ring containing W, X, Y and Z is a five-membered aromatic heterocycle.

In an embodiment, W, X, Y and Z are independently selected from C and N, such that the ring containing W, X, Y and Z is selected from pyrrole, pyrazole, imidazole, 1, 2, 3-triazole and 1,2,4-triazole.

In a preferred embodiment, X is N.

In an embodiment, W is C, X and Y are N and Z is C or N.

In an embodiment, X and Y are N and W and Z are C.

In an embodiment, X, Y and Z are N and W is C.

In a more preferred embodiment, X is N and W, Y and Z are C.

R5, R6 and R7 are independently absent, or are independently selected from H, alkyl, halo, aryl, heteroaryl and CF$_3$.

In an embodiment, R5 is absent or is selected from H, alkyl, CF$_3$ and aryl.

In an embodiment, R5 is absent or is selected from H, methyl CF$_3$ and phenyl.

In a preferred embodiment R5 is H.

In an embodiment, R6 and R7 are independently absent, or are independently selected from H, alkyl, aryl and CF$_3$.

In an embodiment, R6 and R7 are independently absent, or are independently selected from H, methyl, ethyl, n-propyl, phenyl and CF$_3$.

In a preferred embodiment, R6 and R7 are methyl.

In an embodiment, X and Y are N, W and Z are C, and R5 and R7 are H.

In an embodiment, X, Y and Z are N, W is C, and R7 is H.

In a preferred embodiment, X is N, W, Y and Z are C, R5 is H and R6 and R7 are methyl.

R14 and R15 together with the nitrogen to which they are attached form a 4-, 5-, 6- or 7-membered heterocyclic ring which may be saturated or unsaturated with 1 or 2 double bonds, and optionally may be oxo substituted.

In a preferred embodiment, P is —C(R10)(R11)NH$_2$ and Q is H.

R8 and R9 are independently selected from H and alkyl, or may together form a cycloalkyl ring.

In an embodiment, R8 and R9 are independently selected from H and alkyl, or may together form a cyclopropyl ring.

In an embodiment, R8 and R9 are independently selected from H and methyl, or may together form a cyclopropyl ring.

In a preferred embodiment, R8 and R9 are H.

R10 and R11 are independently selected from H and alkyl, or may together form a cycloalkyl ring or a cyclic ether.

In an embodiment, R10 and R11 are independently selected from H and alkyl, or may together form a cyclopropyl ring.

In an embodiment, R10 and R11 are independently selected from H and methyl, or may together form a cyclopropyl ring.

In a preferred embodiment, R10 and R11 are H.

In a preferred embodiment, L is methylene.

A is selected from N-linked morpholine, aryl, and heteroaryl.

In an embodiment, A is selected from aryl, and heteroaryl.

In an embodiment, A is selected from:

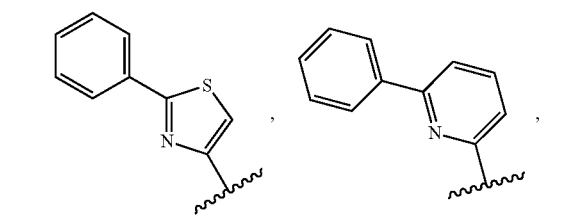

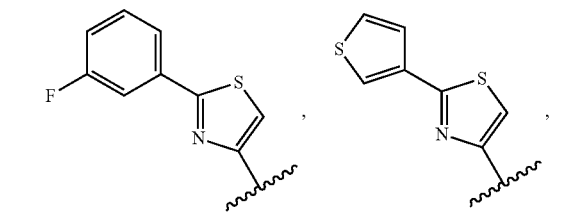

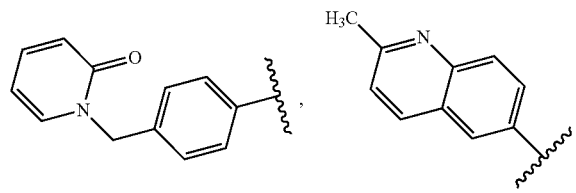

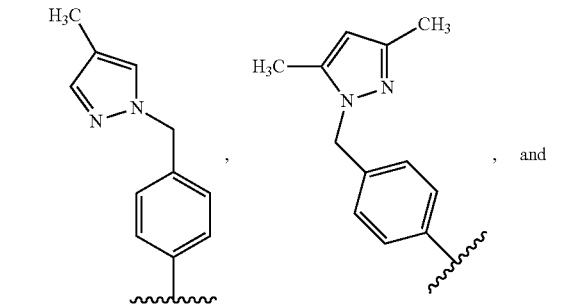

, and

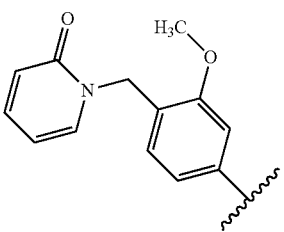

In an embodiment A is selected from:

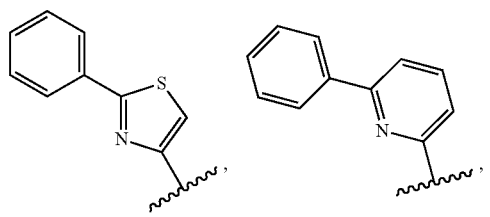

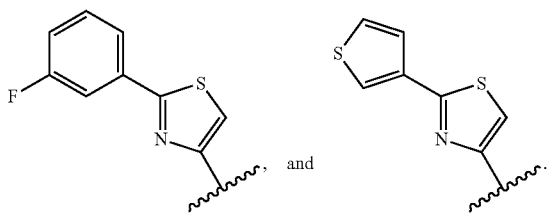

, and

In an embodiment, A is selected from:

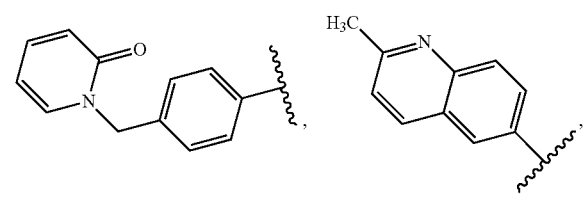

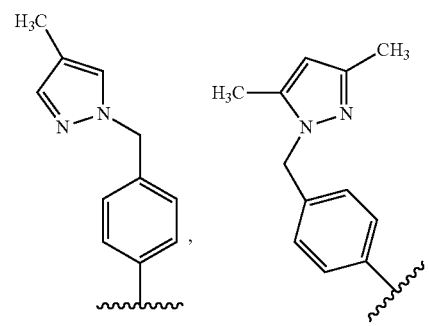

, and

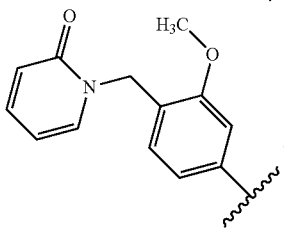

In an aspect, R5, R6 and R7 are absent or H; and A is selected from:

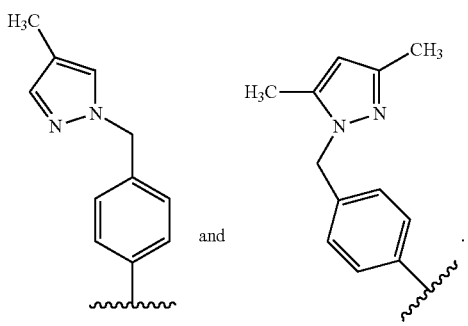 [SMILES: *c1ccc(Cn2cc(C)cn2)cc1 ; *c1ccc(Cn2nc(C)cc2C)cc1]

and

In a preferred aspect, A is:

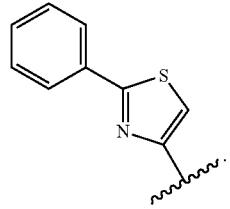 [SMILES: *c1csc(-c2ccccc2)n1]

In an aspect, the invention comprises a compound selected from:

2,5-Dimethyl-1-(2-phenyl-thiazol-4-ylmethyl)-1H-pyrrole-3-carboxylic acid 4-aminomethyl-benzylamide;
2,5-Dimethyl-1-(2-phenyl-thiazol-4-ylmethyl)-1H-pyrrole-3-carboxylic acid 4-aminomethyl-2-methyl-benzylamide;
2,5-Dimethyl-1-(2-phenyl-thiazol-4-ylmethyl)-1H-pyrrole-3-carboxylic acid 4-aminomethyl-2,6-dimethyl-benzylamide;
2,5-Dimethyl-1-(2-phenyl-thiazol-4-ylmethyl)-1H-pyrrole-3-carboxylic acid 4-(1-amino-cyclopropyl)-benzylamide;
2,5-Dimethyl-1-(6-phenyl-pyridin-2-ylmethyl)-1H-pyrrole-3-carboxylic acid 4-aminomethyl-benzylamide;
1-[2-(3-Fluoro-phenyl)-thiazol-4-ylmethyl]-2,5-dimethyl-1H-pyrrole-3-carboxylic acid 4-aminomethyl-benzylamide;
2,5-Dimethyl-1-(2-thiophen-3-yl-thiazol-4-ylmethyl)-1H-pyrrole-3-carboxylic acid 4-aminomethyl-benzylamide;
2,5-Dimethyl-1-(2-phenyl-thiazol-4-ylmethyl)-1H-pyrrole-3-carboxylic acid (6-aminomethyl-pyridin-3-ylmethyl)-amide;
2,5-Dimethyl-1-(2-phenyl-thiazol-4-ylmethyl)-1H-pyrrole-3-carboxylic acid 4-aminomethyl-3-fluoro-benzylamide;
2,5-Dimethyl-1-(2-phenyl-thiazol-4-ylmethyl)-1H-pyrrole-3-carboxylic acid 4-aminomethyl-2-fluoro-benzylamide;
2,5-Dimethyl-1-(2-phenyl-thiazol-4-ylmethyl)-1H-pyrrole-3-carboxylic acid 4-aminomethyl-2-chloro-benzylamide;
2,5-Dimethyl-1-(2-phenyl-thiazol-4-ylmethyl)-1H-pyrrole-3-carboxylic acid 4-aminomethyl-2-trifluoromethyl-benzylamide;
2,5-Dimethyl-1-(2-phenyl-thiazol-4-ylmethyl)-1H-pyrrole-3-carboxylic acid 4-aminomethyl-2-methoxy-benzylamide;
1-[4-(4-Methyl-pyrazol-1-ylmethyl)-benzyl]-1H-pyrazole-4-carboxylic acid 4-aminomethyl-benzylamide;
1-[4-(3,5-Dimethyl-pyrazol-1-ylmethyl)-benzyl]-1H-pyrazole-4-carboxylic acid 4-aminomethyl-benzylamide;
2,5-Dimethyl-1-[4-(2-oxo-2H-pyridin-1-ylmethyl)-benzyl]-1H-pyrrole-3-carboxylic acid 4-aminomethyl-benzylamide;
2,5-Dimethyl-1-[4-(2-oxo-2H-pyridin-1-ylmethyl)-benzyl]-1H-pyrrole-3-carboxylic acid 4-aminomethyl-2-methyl-benzylamide;
1-Ethyl-4-methyl-5-[4-(2-oxo-2H-pyridin-1-ylmethyl)-benzyl]-1H-pyrrole-2-carboxylic acid 4-aminomethyl-2-methyl-benzylamide;
2,5-Dimethyl-1-[4-(2-oxo-2H-pyridin-1-ylmethyl)-benzyl]-1H-pyrrole-3-carboxylic acid 4-aminomethyl-2,6-dimethyl-benzylamide;
1-Ethyl-4-methyl-5-[4-(2-oxo-2H-pyridin-1-ylmethyl)-benzyl]-1H-pyrrole-2-carboxylic acid 4-aminomethyl-2,6-dimethyl-benzylamide;
2,5-Dimethyl-1-[4-(4-methyl-pyrazol-1-ylmethyl)-benzyl]-1H-pyrrole-3-carboxylic acid 4-aminomethyl-benzylamide;
2,5-Dimethyl-1-[4-(4-methyl-pyrazol-1-ylmethyl)-benzyl]-1H-pyrrole-3-carboxylic acid 4-aminomethyl-2-methyl-benzylamide;
1-Ethyl-4-methyl-5-[4-(4-methyl-pyrazol-1-ylmethyl)-benzyl]-1H-pyrrole-2-carboxylic acid 4-aminomethyl-2-methyl-benzylamide;
2,5-Dimethyl-1-[4-(4-methyl-pyrazol-1-ylmethyl)-benzyl]-1H-pyrrole-3-carboxylic acid 4-aminomethyl-2,6-dimethyl-benzylamide;
1-Ethyl-4-methyl-5-[4-(4-methyl-pyrazol-1-ylmethyl)-benzyl]-1H-pyrrole-2-carboxylic acid 4-aminomethyl-2,6-dimethyl-benzylamide;
1-[4-(4-Methyl-pyrazol-1-ylmethyl)-benzyl]-1H-imidazole-4-carboxylic acid 4-aminomethyl-benzylamide;
1-[4-(4-Methyl-pyrazol-1-ylmethyl)-benzyl]-1H-pyrazole-4-carboxylic acid 4-aminomethyl-2-methyl-benzylamide;
1-[4-(4-Methyl-pyrazol-1-ylmethyl)-benzyl]-1H-imidazole-4-carboxylic acid 4-aminomethyl-2-methyl-benzylamide;
1-[4-(4-Methyl-pyrazol-1-ylmethyl)-benzyl]-1H-[1,2,3]triazole-4-carboxylic acid 4-aminomethyl-benzylamide;
1-[4-(4-Methyl-pyrazol-1-ylmethyl)-benzyl]-1H-[1,2,3]triazole-4-carboxylic acid 4-aminomethyl-2-methyl-benzylamide;
1-[4-(4-Methyl-pyrazol-1-ylmethyl)-benzyl]-1H-pyrazole-4-carboxylic acid 4-aminomethyl-2,6-dimethyl-benzylamide;
1-[4-(4-Methyl-pyrazol-1-ylmethyl)-benzyl]-1H-imidazole-4-carboxylic acid 4-aminomethyl-2,6-dimethyl-benzylamide;
1-[4-(4-Methyl-pyrazol-1-ylmethyl)-benzyl]-1H-[1,2,3]triazole-4-carboxylic acid 4-aminomethyl-2,6-dimethyl-benzylamide;
1-Ethyl-4-methyl-5-[4-(4-methyl-pyrazol-1-ylmethyl)-benzyl]-1H-pyrrole-2-carboxylic acid 4-aminomethyl-benzylamide;
1-Ethyl-4-methyl-5-[4-(2-oxo-2H-pyridin-1-ylmethyl)-benzyl]-1H-pyrrole-2-carboxylic acid 4-aminomethyl-benzylamide;
5-Methyl-1-[4-(4-methyl-pyrazol-1-ylmethyl)-benzyl]-1H-pyrazole-4-carboxylic acid 4-aminomethyl-2,6-dimethyl-benzylamide;
1-[4-(4-Methyl-pyrazol-1-ylmethyl)-benzyl]-3-trifluoromethyl-1H-pyrazole-4-carboxylic acid 4-aminomethyl-3-fluoro-benzylamide;
1-[4-(4-Methyl-pyrazol-1-ylmethyl)-benzyl]-3-trifluoromethyl-1H-pyrazole-4-carboxylic acid 4-aminomethyl-2,6-dimethyl-benzylamide;
1-[4-(4-Methyl-pyrazol-1-ylmethyl)-benzyl]-3-trifluoromethyl-1H-pyrazole-4-carboxylic acid 4-aminomethyl-3-fluoro-2-methyl-benzylamide;
3-Methyl-1-(2-methyl-quinolin-6-ylmethyl)-1H-pyrazole-4-carboxylic acid 4-aminomethyl-2,6-dimethyl-benzylamide;
5-Methyl-1-(2-methyl-quinolin-6-ylmethyl)-1H-pyrazole-4-carboxylic acid 4-aminomethyl-2,6-dimethyl-benzylamide;

1-(2-Methyl-quinolin-6-ylmethyl)-3-trifluoromethyl-1H-pyrazole-4-carboxylic acid 4-aminomethyl-2,6-dimethyl-benzylamide;

1-(2-Pyrrolidin-1-yl-pyridin-4-ylmethyl)-3-trifluoromethyl-1H-pyrazole-4-carboxylic acid 4-aminomethyl-2,6-dimethyl-benzylamide;

and pharmaceutically acceptable salts and solvates thereof.

Therapeutic Applications

As previously mentioned, the compounds of the present invention are potent and selective inhibitors of plasma kallikrein. They are therefore useful in the treatment of disease conditions for which over-activity of plasma kallikrein is a causative factor.

Accordingly, the present invention provides a compound of formula (I) for use in medicine.

The present invention also provides for the use of a compound of formula (I) in the manufacture of a medicament for the treatment or prevention of a disease or condition in which plasma kallikrein activity is implicated.

The present invention also provides a compound of formula (I) for use in the treatment or prevention of a disease or condition in which plasma kallikrein activity is implicated.

The present invention also provides a method of treatment of a disease or condition in which plasma kallikrein activity is implicated comprising administration to a subject in need thereof a therapeutically effective amount of a compound of formula (I).

In one aspect, the disease or condition in which plasma kallikrein activity is implicated is selected from diseases or conditions in which plasma kallikrein activity is implicated include impaired visual acuity, diabetic retinopathy, diabetic macular edema, hereditary angioedema, diabetes, pancreatitis, cerebral haemorrhage, nephropathy, cardiomyopathy, neuropathy, inflammatory bowel disease, arthritis, inflammation, septic shock, hypotension, cancer, adult respiratory distress syndrome, disseminated intravascular coagulation, cardiopulmonary bypass surgery and bleeding from post operative surgery.

In a preferred aspect, the disease or condition in which plasma kallikrein activity is implicated is retinal vascular permeability associated with diabetic retinopathy and diabetic macular edema.

Combination Therapy

The compounds of the present invention may be administered in combination with other therapeutic agents. Suitable combination therapies include a compound of formula (I) combined with one or more agents selected from agents that inhibit platelet-derived growth factor (PDGF), endothelial growth factor (VEGF), integrin alpha5beta1, steroids, other agents that inhibit plasma kallikrein and other inhibitors of inflammation. Specific examples of therapeutic agents that may be combined with the compounds of the present invention include those disclosed in EP2281885A and by S. Patel in *Retina*, 2009 June; 29(6 Suppl):S45-8.

When combination therapy is employed, the compounds of the present invention and said combination agents may exist in the same or different pharmaceutical compositions, and may be administered separately, sequentially or simultaneously.

In another aspect, the compounds of the present invention may be administered in combination with laser treatment of the retina. The combination of laser therapy with intravitreal injection of an inhibitor of VEGF for the treatment of diabetic macular edema is known (Elman M, Aiello L, Beck R, et al. "Randomized trial evaluating ranibizumab plus prompt or deferred laser or triamcinolone plus prompt laser for diabetic macular edema". Ophthalmology. 27 Apr. 2010).

Definitions

The term "alkyl" includes saturated hydrocarbon residues including:

linear groups up to 10 carbon atoms ($C_1$-$C_{10}$), or of up to 6 carbon atoms ($C_1$-$C_6$), or of up to 4 carbon atoms ($C_1$-$C_4$). Examples of such alkyl groups include, but are not limited to, $C_1$-methyl, $C_2$-ethyl, $C_3$-propyl and $C_4$-n-butyl.

branched groups of between 3 and 10 carbon atoms ($C_3$-$C_{10}$), or of up to 7 carbon atoms ($C_3$-$C_7$), or of up to 4 carbon atoms ($C_3$-$C_4$). Examples of such alkyl groups include, but are not limited to, $C_3$-iso-propyl, $C_4$-sec-butyl, $C_4$-iso-butyl, $C_4$-tert-butyl and $C_5$-neo-pentyl.

each optionally substituted as stated above.

The term "alkoxy" includes O-linked hydrocarbon residues including:

linear groups of between 1 and 6 carbon atoms ($C_1$-$C_6$), or of between 1 and 4 carbon atoms ($C_1$-$C_4$). Examples of such alkoxy groups include, but are not limited to, $C_1$-methoxy, $C_2$-ethoxy, $C_3$-n-propoxy and $C_4$-n-butoxy.

branched groups of between 3 and 6 carbon atoms ($C_3$-$C_6$) or of between 3 and 4 carbon atoms ($C_3$-$C_4$). Examples of such alkoxy groups include, but are not limited to, $C_3$-iso-propoxy, and $C_4$-sec-butoxy and tert-butoxy.

each optionally substituted as stated above.

Unless otherwise stated, halo is selected from Cl, F, Br and I.

Cycloalkyl is as defined above. Cycloalkyl may be substituted with a substituent selected from those stated above. Cycloalkyl groups may contain from 3 to 7 carbon atoms, or from 3 to 6 carbon atoms, or from 3 to 5 carbon atoms, or from 3 to 4 carbon atoms. Examples of suitable monocyclic cycloalkyl groups include cyclopropyl, cyclobutyl, cyclopentyl, cyclohexyl and cycloheptyl.

Aryl is as defined above. Typically, aryl will be optionally substituted with 1, 2 or 3 substituents. Optional substituents are selected from those stated above. Examples of suitable aryl groups include phenyl and naphthyl (each optionally substituted as stated above). Preferably aryl is selected from phenyl, substituted phenyl (substituted as stated above) and naphthyl.

Heteroaryl is as defined above. Examples of suitable heteroaryl groups include thienyl, furanyl, pyrrolyl, pyrazolyl, imidazoyl, oxazolyl, isoxazolyl, thiazolyl, isothiazolyl, triazolyl, oxadiazolyl, thiadiazolyl, tetrazolyl, pyridinyl, pyridazinyl, pyrimidinyl, pyrazinyl, indolyl, benzimidazolyl, benzotriazolyl, quinolinyl and isoquinolinyl (optionally substituted as stated above). Preferably heteroaryl is selected from pyridyl, benzothiazole, indole, N-methylindole, thiazole, substituted thiazole, thiophenyl, furyl, pyrazine, pyrazole, substituted pyrazole, quinolone and substituted quinolone; wherein substituents are as stated above.

The term "N-linked", such as in "N-linked morpholine", means that the morpholinyl group is joined to the remainder of the molecule via a ring nitrogen atom.

The term "O-linked", such as in "O-linked hydrocarbon residue", means that the hydrocarbon residue is joined to the remainder of the molecule via an oxygen atom.

In groups such as —COOR12, "—" denotes the point of attachment of the substituent group to the remainder of the molecule.

"Pharmaceutically acceptable salt" means a physiologically or toxicologically tolerable salt and includes, when appropriate, pharmaceutically acceptable base addition salts and pharmaceutically acceptable acid addition salts. For example (i) where a compound of the invention contains one or more acidic groups, for example carboxy groups, pharmaceutically acceptable base addition salts that can be formed include sodium, potassium, calcium, magnesium and ammonium salts, or salts with organic amines, such as, diethylamine, N-methyl-glucamine, diethanolamine or amino acids (e.g. lysine) and the like; (ii) where a compound of the invention contains a basic group, such as an amino group, pharmaceutically acceptable acid addition salts that can be formed include hydrochlorides, hydrobromides, sulfates, phosphates, acetates, citrates, lactates, tartrates, mesylates, succinates, oxalates, phosphates, esylates, tosylates, benzenesulfonates, naphthalenedisulphonates, maleates, adipates, fumarates, hippurates, camphorates, xinafoates, p-acetamidobenzoates, dihydroxybenzoates, hydroxynaphthoates, succinates, ascorbates, oleates, bisulfates and the like.

Hemisalts of acids and bases can also be formed, for example, hemisulfate and hemicalcium salts.

For a review of suitable salts, see "Handbook of Pharmaceutical Salts: Properties, Selection and Use" by Stahl and Wermuth (Wiley-VCH, Weinheim, Germany, 2002).

"Prodrug" refers to a compound which is convertible in vivo by metabolic means (e.g. by hydrolysis, reduction or oxidation) to a compound of the invention. Suitable groups for forming prodrugs are described in 'The Practice of Medicinal Chemistry, $2^{nd}$ Ed. pp 561-585 (2003) and in F. J. Leinweber, *Drug Metab. Res.,* 1987, 18, 379.

The compounds of the invention can exist in both unsolvated and solvated forms. The term 'solvate' is used herein to describe a molecular complex comprising the compound of the invention and a stoichiometric amount of one or more pharmaceutically acceptable solvent molecules, for example, ethanol. The term 'hydrate' is employed when the solvent is water.

Where compounds of the invention exist in one or more geometrical, optical, enantiomeric, diastereomeric and tautomeric forms, including but not limited to cis- and trans-forms, E- and Z-forms, R-, S- and meso-forms, keto-, and enol-forms. Unless otherwise stated a reference to a particular compound includes all such isomeric forms, including racemic and other mixtures thereof. Where appropriate such isomers can be separated from their mixtures by the application or adaptation of known methods (e.g. chromatographic techniques and recrystallisation techniques). Where appropriate such isomers can be prepared by the application or adaptation of known methods (e.g. asymmetric synthesis).

In the context of the present invention, references herein to "treatment" include references to curative, palliative and prophylactic treatment.

General Methods

The compounds of formula (I) should be assessed for their biopharmaceutical properties, such as solubility and solution stability (across pH), permeability, etc., in order to select the most appropriate dosage form and route of administration for treatment of the proposed indication. They may be administered alone or in combination with one or more other compounds of the invention or in combination with one or more other drugs (or as any combination thereof). Generally, they will be administered as a formulation in association with one or more pharmaceutically acceptable excipients. The term 'excipient' is used herein to describe any ingredient other than the compound(s) of the invention which may impart either a functional (i.e., drug release rate controlling) and/or a non-functional (i.e., processing aid or diluent) characteristic to the formulations. The choice of excipient will to a large extent depend on factors such as the particular mode of administration, the effect of the excipient on solubility and stability, and the nature of the dosage form.

Compounds of the invention intended for pharmaceutical use may be administered as a solid or liquid, such as a tablet, capsule or solution. Pharmaceutical compositions suitable for the delivery of compounds of the present invention and methods for their preparation will be readily apparent to those skilled in the art. Such compositions and methods for their preparation may be found, for example, in Remington's Pharmaceutical Sciences, 19th Edition (Mack Publishing Company, 1995).

Accordingly, the present invention provides a pharmaceutical composition comprising a compound of formula (I) and a pharmaceutically acceptable carrier, diluent or excipient.

For the treatment of conditions such as retinal vascular permeability associated with diabetic retinopathy and diabetic macular edema, the compounds of the invention may be administered in a form suitable for injection into the ocular region of a patient, in particular, in a form suitable for intra-vitreal injection. It is envisaged that formulations suitable for such use will take the form of sterile solutions of a compound of the invention in a suitable aqueous vehicle. The compositions may be administered to the patient under the supervision of the attending physician.

The compounds of the invention may also be administered directly into the blood stream, into subcutaneous tissue, into muscle, or into an internal organ. Suitable means for parenteral administration include intravenous, intraarterial, intraperitoneal, intrathecal, intraventricular, intraurethral, intrasternal, intracranial, intramuscular, intrasynovial and subcutaneous. Suitable devices for parenteral administration include needle (including microneedle) injectors, needle-free injectors and infusion techniques.

Parenteral formulations are typically aqueous or oily solutions. Where the solution is aqueous, excipients such as sugars (including but not restricted to glucose, manitol, sorbitol, etc.), salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

Parenteral formulations may include implants derived from degradable polymers such as polyesters (i.e., polylactic acid, polylactide, polylactide-co-glycolide, polycapro-lactone, polyhydroxybutyrate), polyorthoesters and polyanhydrides. These formulations may be administered via surgical incision into the subcutaneous tissue, muscular tissue or directly into specific organs.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by the use of appropriate formulation techniques, such as the incorporation of co-solvents and/or solubility-enhancing agents such as surfactants, micelle structures and cyclodextrins.

In one embodiment, the compounds of the invention may be administered orally. Oral administration may involve swallowing, so that the compound enters the gastrointestinal tract, and/or buccal, lingual, or sublingual administration by which the compound enters the blood stream directly from the mouth.

Formulations suitable for oral administration include solid plugs, solid microparticulates, semi-solid and liquid (including multiple phases or dispersed systems) such as tablets; soft or hard capsules containing multi- or nano-particulates, liquids, emulsions or powders; lozenges (including liquid-filled); chews; gels; fast dispersing dosage forms; films; ovules; sprays; and buccal/mucoadhesive patches.

Formulations suitable for oral administration may also be designed to deliver the compounds of the invention in an immediate release manner or in a rate-sustaining manner, wherein the release profile can be delayed, pulsed, controlled, sustained, or delayed and sustained or modified in such a manner which optimises the therapeutic efficacy of the said compounds. Means to deliver compounds in a rate-sustaining manner are known in the art and include slow release polymers that can be formulated with the said compounds to control their release.

Examples of rate-sustaining polymers include degradable and non-degradable polymers that can be used to release the said compounds by diffusion or a combination of diffusion and polymer erosion. Examples of rate-sustaining polymers include hydroxypropyl methylcellulose, hydroxypropyl cellulose, methyl cellulose, ethyl cellulose, sodium carboxymethyl cellulose, polyvinyl alcohol, polyvinyl pyrrolidone, xanthum gum, polymethacrylates, polyethylene oxide and polyethylene glycol.

Liquid (including multiple phases and dispersed systems) formulations include emulsions, solutions, syrups and elixirs. Such formulations may be presented as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Liang and Chen, Expert Opinion in Therapeutic Patents, 2001, 11 (6), 981-986.

The formulation of tablets is discussed in Pharmaceutical Dosage Forms: Tablets, Vol. 1, by H. Lieberman and L. Lachman (Marcel Dekker, New York, 1980).

For administration to human patients, the total daily dose of the compounds of the invention is typically in the range 0.01 mg and 1000 mg, or between 0.1 mg and 250 mg, or between 1 mg and 50 mg depending, of course, on the mode of administration.

The total dose may be administered in single or divided doses and may, at the physician's discretion, fall outside of the typical range given herein. These dosages are based on an average human subject having a weight of about 60 kg to 70 kg. The physician will readily be able to determine doses for subjects whose weight falls outside this range, such as infants and the elderly.

Synthetic Methods

The compounds of the present invention can be prepared according to the procedures of the following schemes and examples, using appropriate materials, and are further exemplified by the specific examples provided herein below. Moreover, by utilising the procedures described herein, one of ordinary skill in the art can readily prepare additional compounds that fall within the scope of the present invention claimed herein. The compounds illustrated in the examples are not, however, to be construed as forming the only genus that is considered as the invention. The examples further illustrate details for the preparation of the compounds of the present invention. Those skilled in the art will readily understand that known variations of the conditions and processes of the following preparative procedures can be used to prepare these compounds.

The compounds of the invention may be isolated in the form of their pharmaceutically acceptable salts, such as those described previously herein above.

It may be necessary to protect reactive functional groups (e.g. hydroxy, amino, thio or carboxy) in intermediates used in the preparation of compounds of the invention to avoid their unwanted participation in a reaction leading to the formation of the compounds. Conventional protecting groups, for example those described by T. W. Greene and P. G. M. Wuts in "Protective groups in organic chemistry" John Wiley and Sons, $4^{th}$ Edition, 2006, may be used. For example, a common amino protecting group suitable for use herein is tert-butoxy carbonyl (Boc), which is readily removed by treatment with an acid such as trifluoroacetic acid or hydrogen chloride in an organic solvent such as dichloromethane. Alternatively the amino protecting group may be a benzyloxycarbonyl (Z) group which can be removed by hydrogenation with a palladium catalyst under a hydrogen atmosphere or 9-fluorenylmethyloxycarbonyl (Fmoc) group which can be removed by solutions of secondary organic amines such as diethylamine or piperidine in an organic solvents. Carboxyl groups are typically protected as esters such as methyl, ethyl, benzyl or tert-butyl which can all be removed by hydrolysis in the presence of bases such as lithium or sodium hydroxide. Benzyl protecting groups can also be removed by hydrogenation with a palladium catalyst under a hydrogen atmosphere whilst tert-butyl groups can also be removed by trifluoroacetic acid. Alternatively a trichloroethyl ester protecting group is removed with zinc in acetic acid. A common hydroxy protecting group suitable for use herein is a methyl ether, deprotection conditions comprise refluxing in 48% aqueous HBr for 1-24 hours, or by stirring with borane tribromide in dichloromethane for 1-24 hours. Alternatively where a hydroxy group is protected as a benzyl ether, deprotection conditions comprise hydrogenation with a palladium catalyst under a hydrogen atmosphere.

The compounds according to general formula I can be prepared using conventional synthetic methods for example, but not limited to, the route outlined in Scheme 1. In a typical first step the amine 2 is coupled to an acid 1 using standard coupling condition such as hydroxybenzotriazole and carbodiimide such as water soluble carbodiimide in the presence of an organic base. Other standard coupling methods include the reaction of acids with amines in the presence of 2-(1H-benzotriazole-1-yl)-1,1,3,3-tetramethylaminium hexafluorophosphate or benzotriazole-1-yl-oxy-tris-pyrrolidino-phosphoium hexafluorophosphate or bromo-trispyrrolidino-phosphonium hexafluorophosphate in the presence of organic bases such as triethylamine, N,N-diisopropylethylamine or N-methylmorpholine. Alternatively the amide formation can take place via an acid chloride in the presence of an organic base. Such acid chlorides can be formed by methods well known in the literature, for example reaction of the acid with oxalyl chloride or thionyl chloride.

The route exemplified in Scheme 1 then proceeds in the third step involving reduction of a nitrile. Reduction of compound 3 to compound 5 may be achieved in a single step by reduction with a suitable borohydride in the presence of a suitable transition metal such as cobalt or nickel chloride in a suitable solvent such as methanol at room temperature, alternatively this may be achieved in a single step by direct reduction of the nitrile by hydrogenation in a suitable solvent such as methanol in the presence of a suitable catalyst such as palladium on charcoal in the presence of an acid such as hydrochloric acid to yield the amine 5. In the exemplified scheme the tert-butoxycarbonyl (Boc) protected amine 4 may be isolated (using, for example, the method as described in S. Caddick et al., *Tetrahedron Lett.*, 2000, 41, 3513) and subsequently deprotected by standard means described previously to give the amine 5.

Scheme 1

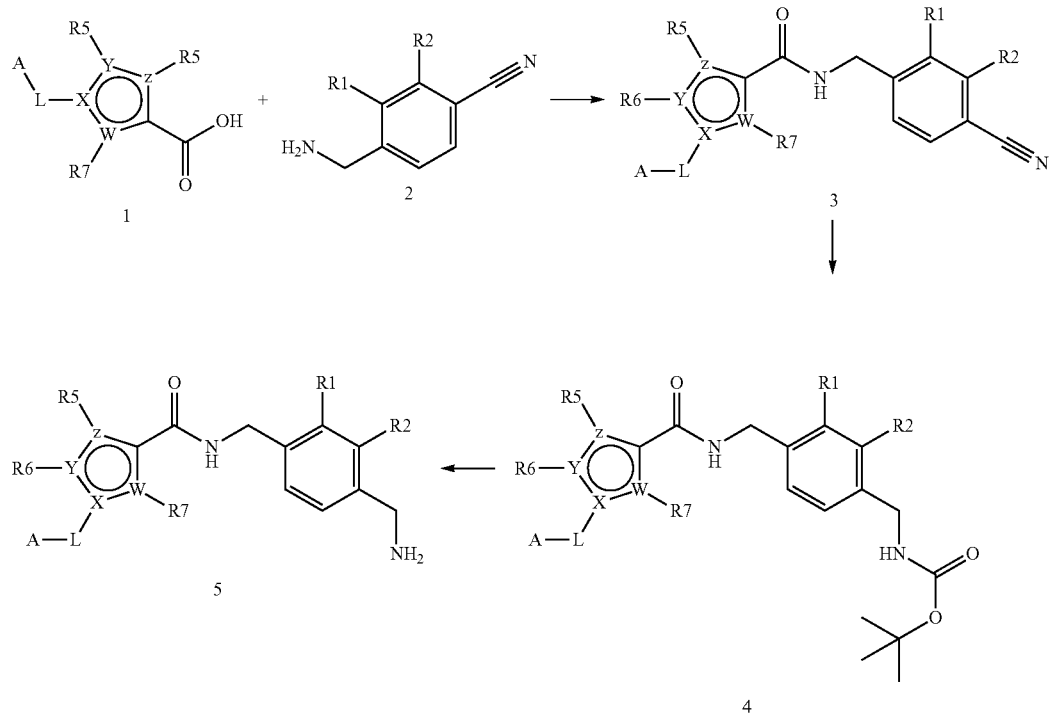

Alternatively compounds according to general formula I can be prepared using the route exemplified in Scheme 2. The acid 1 can be coupled to an amine 6 using suitable coupling methods as previously described to give Compound 7 in which the second amino group is amino-protected with a standard protecting group such as tert-butyloxycarbonyl (Boc), benzyloxycarbonyl (Z) or 9-fluorenylmethyloxycarbonyl (Fmoc). In a typical second step the protecting group is removed to give compound 5 using standard methods as previously described.

Scheme 2

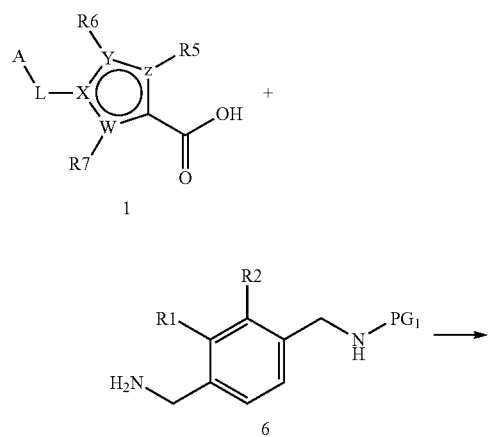

Alternatively compounds according to general formula I can be prepared using the route outlined in Scheme 3. The acid 8 can be coupled to an amine 6 using suitable coupling methods as previously described to give compound 9 in which the second amino group is amino-protected with a standard protecting group such as tert-butyloxycarbonyl (Boc), benzyloxycarbonyl (Z) or 9-fluorenylmethyloxycarbonyl (Fmoc). In a typical second step the nitrogen of the heterocyclic ring is alkylated with compound 10 to give compound 11. The alkylation can be carried out in the presence of a base such as potassium carbonate, cesium carbonate, sodium carbonate or sodium hydride in which case the leaving group is a halide or sulphonate. Alternatively the alkylation may be carried out using an alcohol under Mitsunobu conditions in the presence of triphenylphosphine. In a third step the protecting group is removed to give compound 12 using standard methods as previously described.

e.g. p-toluenesulphonic acid to yield compound 17 which in a typical third step is subsequently hydrolysed to the corresponding acid 18 using standard methods as described previously. In a typical fourth step the acid 18 can be coupled to an amine 6 using suitable coupling methods as previously described to give compound 19 in which the

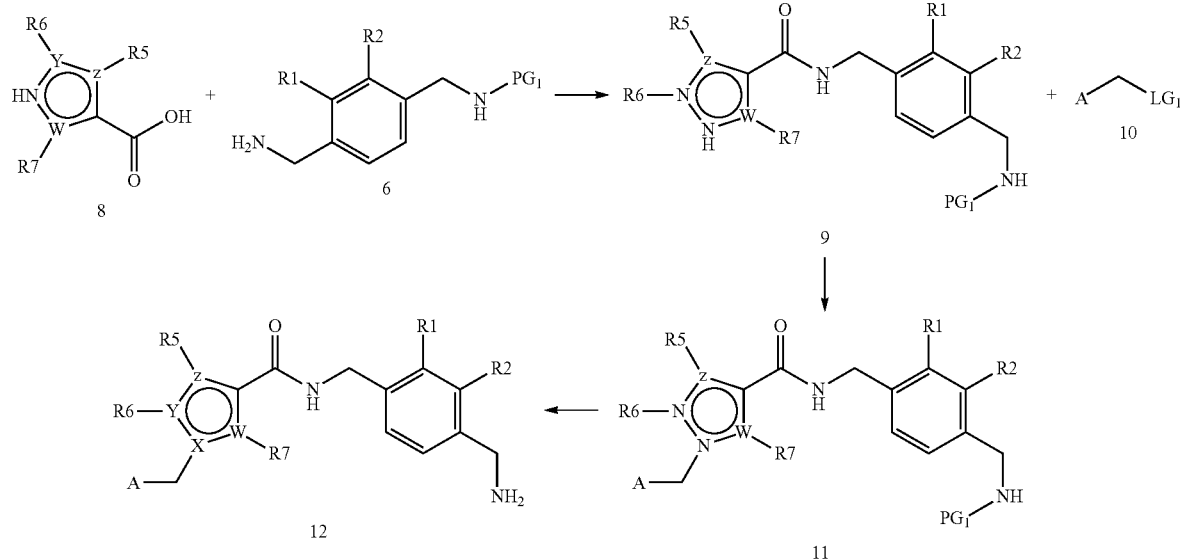

Scheme 3

Alternatively compounds according to general formula I can be prepared using the route outlined in Scheme 4. The pyrrole 17 can be formed in two steps the first of which involves reaction of the sodium salt of an alkyl ketoacetate 13 with a chloroketone 14 in the presence of a base such as potassium carbonate to give compound 15 which in a typical second step is reacted with the amine 16 in the presence of an acid such as but not limited to sulphonic acid derivatives second amino group is amino-protected with a standard protecting group such as tert-butyloxycarbonyl (Boc), benzyloxycarbonyl (Z) or 9-fluorenylmethyloxycarbonyl (Fmoc). In a typical final step the protecting group is removed to give compound 20 using standard methods as previously described.

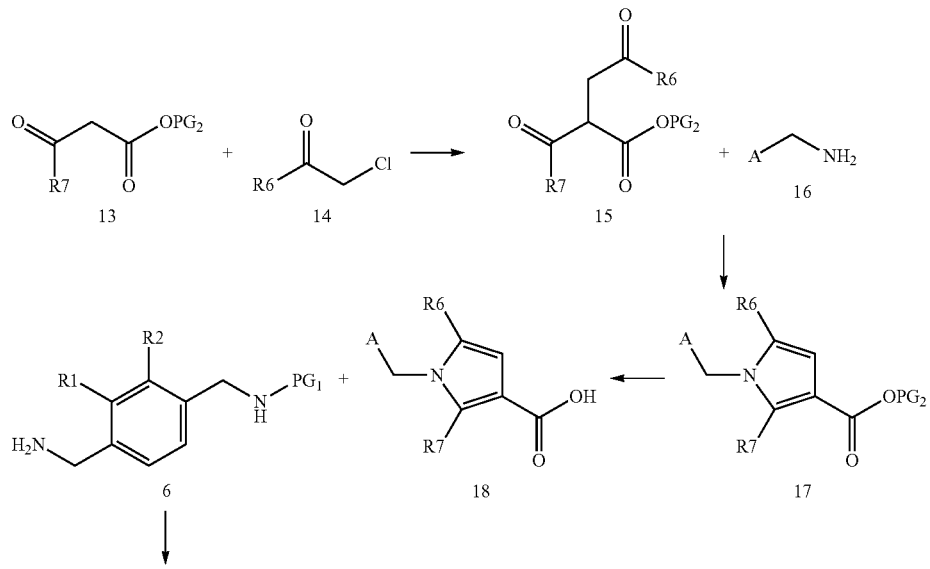

Scheme 4

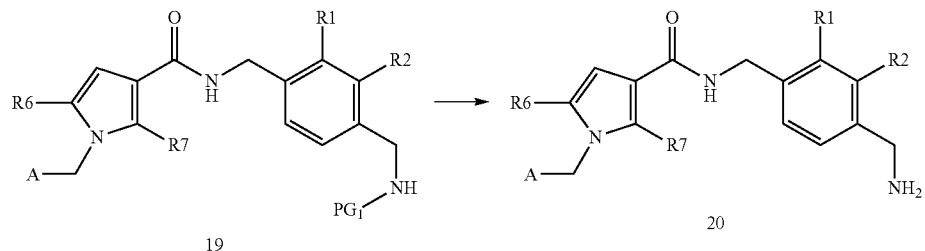

Alternatively compounds according to general formula I can be prepared using the route outlined in Scheme 5. The triazole 22 can be formed by reaction of an alkyl propiolate with the azide 21 under azide alkyne Huisgen cycloaddition conditions employing a catalyst such as copper salts with ascorbic acid derivatives. In a typical second step the ester is hydrolysed to the corresponding acid 23 using standard methods as described previously. In a typical third step the acid 23 can be coupled to an amine 6 using suitable coupling methods as previously described to give compound 24 in which the second amino group is amino-protected with a standard protecting group such as tert-butyloxycarbonyl (Boc), benzyloxycarbonyl (Z) or 9-fluorenylmethyloxycarbonyl (Fmoc). In a typical final step the protecting group is removed to give compound 25 using standard methods as previously described.

Alternatively compounds according to general formula I can be prepared using the route outlined in Scheme 6. The imidazole 26 can be formed by reaction of the acrylate derivative 26 with the amine 16 in the presence of organic bases such as N,N-diisopropylethylamine or triethylamine. In a typical second step the ester is hydrolysed to the corresponding acid 28 using standard methods as described previously. In a typical third step the acid 28 can be coupled to an amine 6 using suitable coupling methods as previously described to give compound 29 in which the second amino group is amino-protected with a standard protecting group such as tert-butyloxycarbonyl (Boc), benzyloxycarbonyl (Z) or 9-fluorenylmethyloxycarbonyl (Fmoc). In a typical final step the protecting group is removed to give compound 30 using standard methods as previously described.

Scheme 5

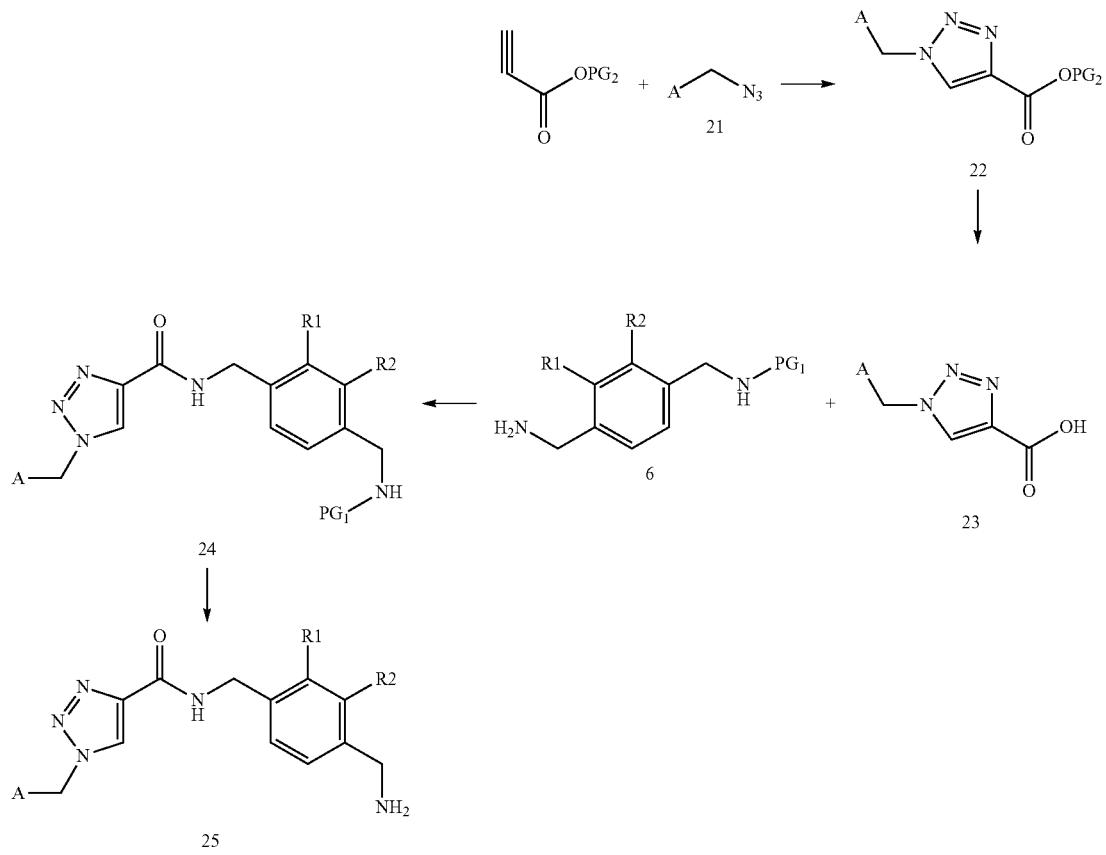

Scheme 6

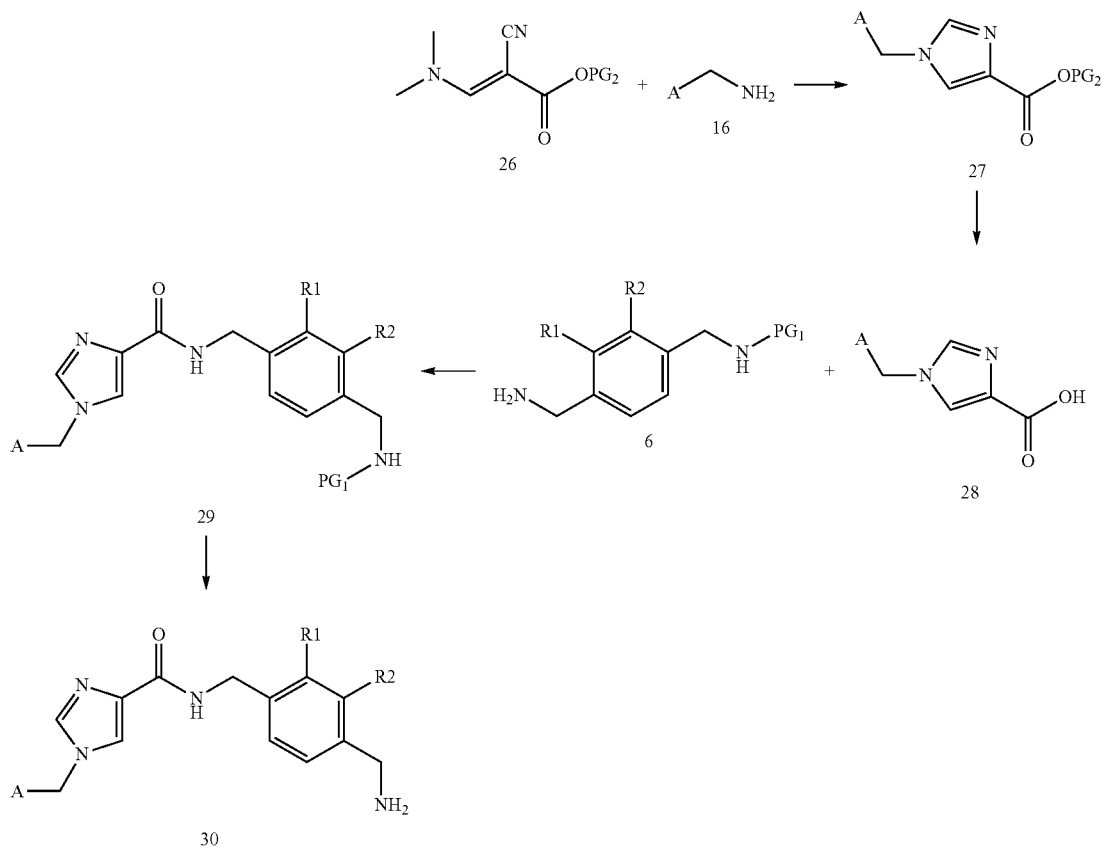

Alternatively compounds according to general formula I can be prepared using the route outlined in Scheme 7. In a typical first step the nitrogen of the heterocyclic ring is derivatised by reaction of compound 9 with the sulphonyl chloride 31 in the presence of organic bases such as N,N-diisopropylethylamine or triethylamine to give compound 32. In a typical final step the protecting group is removed to give compound 33 using standard methods as previously described.

Scheme 7

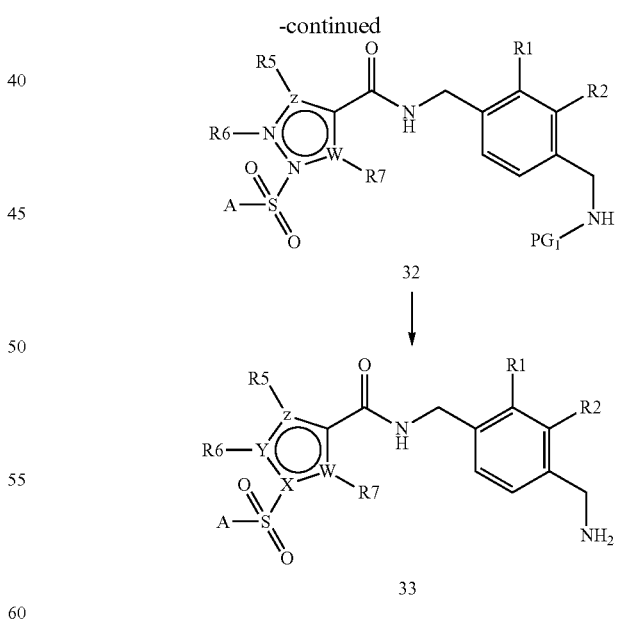

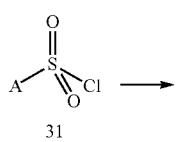

EXAMPLES

The invention is illustrated by the following non-limiting examples in which the following abbreviations and definitions are used:

| | |
|---|---|
| DMF | N,N-Dimethylformamide |
| EtOAc | Ethyl Acetate |
| hrs | Hours |
| HOBt | Hydroxybenzotriazole |
| LCMS | Liquid chromatography mass spectrometry |
| Me | Methyl |
| MeCN | Acetonitrile |
| MeOH | Methanol |
| Min | Minutes |
| MS | Mass spectrum |
| NMR | Nuclear magnetic resonance spectrum - NMR spectra were recorded at a frequency of 400 MHz unless otherwise indicated |
| Pet. Ether | Petroleum ether fraction boiling at 60-80° C. |
| THF | Tetrahydrofuran |
| TFA | Trifluoroacetic acid |

All reactions were carried out under an atmosphere of nitrogen unless specified otherwise.

$^1$H NMR spectra were recorded on a Bruker Avance III (400 MHz) spectrometer with reference to deuterium solvent and at room temperature.

Molecular ions were obtained using LCMS which was carried out using a Chromolith Speedrod RP-18e column, 50×4.6 mm, with a linear gradient 10% to 90% 0.1% HCO$_2$H/MeCN into 0.1% HCO$_2$H/H$_2$O over 11 min, flow rate 1.5 mL/min. Data was collected using a Thermofinnigan Surveyor MSQ mass spectrometer with electospray ionisation in conjunction with a Thermofinnigan Surveyor LC system.

Chemical names were generated using the Autonom software provided as part of the ISIS Draw package from MDL Information Systems.

Where products were purified by flash chromatography, 'silica' refers to silica gel for chromatography, 0.035 to 0.070 mm (220 to 440 mesh) (e.g. Merck silica gel 60), and an applied pressure of nitrogen up to 10 p.s.i accelerated column elution. Reverse phase preparative HPLC purifications were carried out using a Waters 2525 binary gradient pumping system at flow rates of typically 20 ml/min using a Waters 2996 photodiode array detector.

All solvents and commercial reagents were used as received.

Compound A

4-Bromo-2-fluoro-3-methyl-benzonitrile

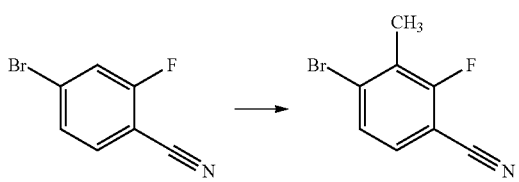

To a solution of diisopropylamine (4.2 mL, 30 mmol) in dry THF (5 ml) was added a solution of nBuLi in THF (2.5M, 11 mL, 27.5 mmol) dropwise at −78° C. Once addition was complete, the reaction was allowed to warm to 0° C. and stirred in an ice-salt bath for 40 mins. The resulting solution was added dropwise to a solution of 4-bromo-2-fluorobenzonitrile (5 g, 25 mmol) in dry THF (50 ml) at −78° C. and the mixture stirred for 2.5 hrs. The reaction mixture was then cooled to −78° C. and methyl iodide added in one portion and the mixture slowly allowed to warm to room temperature. The reaction was quenched with aqueous NH$_4$Cl and extracted with EtOAc (3×40 ml). The combined organics were washed with water (40 ml) and brine (40 ml). The organics were dried over MgSO$_4$, filtered and concentrated. The residue was purified by column chromatography eluting with 9:1 pet ether:ethyl acetate to afford 4-bromo-2-fluoro-3-methyl-benzonitrile as an off white solid (2.40 g, 45% yield).

Compound B

4-Bromo-2-fluoro-3,5-dimethyl-benzonitrile

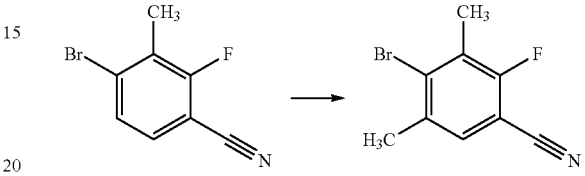

Following a similar procedure to that described for the preparation of Compound A, 4-bromo-2-fluoro-3-methyl-benzonitrile was converted to 4-bromo-2-fluoro-3,5-dimethyl-benzonitrile which was isolated as a lime green oil.

Example 1

2,5-Dimethyl-1-(2-phenyl-thiazol-4-ylmethyl)-1H-pyrrole-3-carboxylic acid 4-aminomethyl-benzylamide

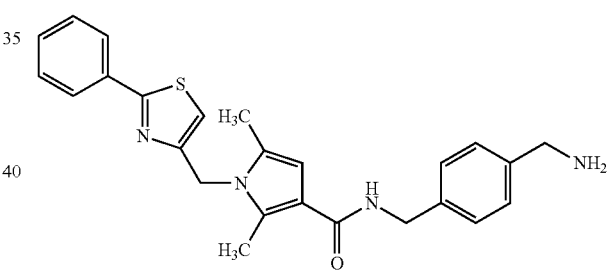

A. 2-Acetyl-4-oxo-pentanoic acid ethyl ester

Ethylacetoacetate sodium salt (17.10 g, 112 mmol) was suspended in acetone (500 mls) Potassium carbonate (15.54 g, 112 mmol) and potassium iodide (3.73 g, 22.48 mmol) were added and the resulting solution was refluxed. Chloroacetone (11.41 g, 124 mmol) was added dropwise over a period of 5 mins). Once the addition was complete the mixture was heated under reflux for a further 2 hours. The reaction mixture was allowed to cool to room temperature and the solid material was filtered off and washed with acetone. The resultant filtrate was evaporated and purified by flash chromatography (silica), eluant 75% Pet. Ether (60-80° C.), 25% EtOAc, fractions combined and evaporated in vacuo to give a yellow oil identified as 2-acetyl-4-oxo-pentanoic acid ethyl ester (10.1 g, 54.2 mmol, 48%).

B. 1-[2-phenyl)-thiazol-4-ylmethyl]-2,5-dimethyl-1H-pyrrole-3-carboxylic acid ethyl ester 2-Acetyl-4-oxo-pentanoic acid ethyl ester (1.8 g, 9.66 mmol) was dissolved in toluene (35 mls), 2-phenyl-thiazoyl- 4-methylamine (2.02 g, 10.62 mmol) and p-toluenesulphonic acid (183 mg, 0.966 mmol) were added. The reaction mixture was heated at reflux for 4 hours after which time it was diluted with ethyl acetate and washed with NaHCO$_3$ (1×30 mls), water (1×30 mls), brine (1×30 mls), dried (Na$_2$SO$_4$) and evaporated in vacuo. The residue was purified by flash chromatography (silica), eluant 85% Pet. Ether (60-80° C.), 15% EtOAc, fractions combined and evaporated in vacuo to give a colourless oil identified as 1-[2-phenyl)-thiazol-4-ylmethyl]-2,5-dimethyl-1H-pyrrole-3-carboxylic acid ethyl ester (1.26 g, 3.69 mmol, 38%).

[M+H]+=341.27

C. 2,5-Dimethyl-1-(2-phenyl-thiazol-4-ylmethyl)-1H-pyrrole-3-carboxylic acid 1-[2-Phenyl)-thiazol-4-ylmethyl]-2,5-dimethyl-1H-pyrrole-3-carboxylic acid ethyl ester (1.07 g, 3.14 mmol) was dissolved in ethanol (50 mls). Sodium hydroxide (629 mg, 15.72 mmol) in water (5 mls) was added. The reaction mixture was heated at 90° C. for 3 days after which time the solvent was removed in vacuo. The residue was diluted with water and acidified to pH1 with 1M HCl and extracted with ethyl acetate (3×50 mls). The combined extracts were washed with water (1×30 mls), brine (1×30 mls), dried (Na$_2$SO$_4$) and evaporated in vacuo to give an off white solid identified as 2,5-dimethyl-1-(2-phenyl-thiazol-4-ylmethyl)-1H-pyrrole-3-carboxylic acid (980 mg, 3.14 mmol, 100%).

[M+H]+=313.23

D. [4-({[2,5-Dimethyl-1-(2-phenyl-thiazol-4-ylmethyl)-1H-pyrrole-3-carbonyl]-amino}-methyl)-benzyl]-carbamic acid tert-butyl ester 2,5-Dimethyl-1-(2-phenyl-thiazol-4-ylmethyl)-1H-pyrrole-3-carboxylic acid (1.60 g, 5.12 mmol) was dissolved in CH$_2$Cl$_2$ (100 mls) and DMF (5 mls). This solution was cooled to 0° C. 1-(N-Boc-aminomethyl)-4-(aminomethyl)benzene (1.21 g, 5.12 mmol) was added followed by HOBt (830 mg, 6.14 mmol) and triethylamine (2.59 g, 25.6 mmol). Water soluble carbodiimide (1.37 g, 4.33 mmol) was then added. After 18 hrs at 0° C. to room temperature reaction mixture was diluted with chloroform (200 mls) and washed with NaHCO$_3$ (1×50 mls), water (1×50 mls), brine (1×50 mls), dried (Na$_2$SO$_4$) and evaporated in vacuo. The residue was purified by flash chromatography (silica), eluant 50% Pet. Ether (60-80° C.), 50% EtOAc, fractions combined and evaporated in vacuo to give a white solid identified as [4-({[2,5-dimethyl-1-(2-phenyl-thiazol-4-ylmethyl)-1H-pyrrole-3-carbonyl]-amino}-methyl)-benzyl]-carbamic acid tert-butyl ester (2.30 g, 4.33 mmol, 85%).

[M+H]+=531.29.

E. 2,5-Dimethyl-1-(2-phenyl-thiazol-4-ylmethyl)-1H-pyrrole-3-carboxylic acid 4-aminomethyl-benzylamide

[4-({[2,5-Dimethyl-1-(2-phenyl-thiazol-4-ylmethyl)-1H-pyrrole-3-carbonyl]-amino}-methyl)-benzyl]-carbamic acid tert-butyl ester (2.30 g, 4.33 mmol) was dissolved in methanol (40 mls) to which 4M HCl in dioxan (10 mls) was added. After three hours at room temperature the solvent was removed in vacuo and the residue was azeotroped from toluene. The free base was liberated with a mixture of dichloromethane, MeOH and NH$_3$ then evaporated. The residue was purified by flash chromatography (silica), eluant dichlromethane:MeOH:NH$_3$ (100:10:1). The residue was triturated with EtOAc/Pet Ether 60-80° C. to give an off white solid identified as 2,5-dimethyl-1-(2-phenyl-thiazol-4-ylmethyl)-1H-pyrrole-3-carboxylic acid 4-aminomethyl-benzylamide (1.2 g, 2.79 mmol, 64%).

[M+H]+=431.20

$^1$H NMR: (d6-DMSO, δ: 2.26 (3H, s), 2.56 (3H, s), 3.33 (2H, br s), 3.68 (2H, s), 4.33 (2H, d, J=6.1 Hz), 5.17 (2H, s), 6.29 (1H, s), 7.19-7.26 (5H, m), 7.48 (3H, m), 7.90-7.92 (2H, m), 8.05 (1H, t, J=6.1 Hz).

Example 2

2,5-Dimethyl-1-(2-phenyl-thiazol-4-ylmethyl)-1H-pyrrole-3-carboxylic acid 4-aminomethyl-2-methyl-benzylamide

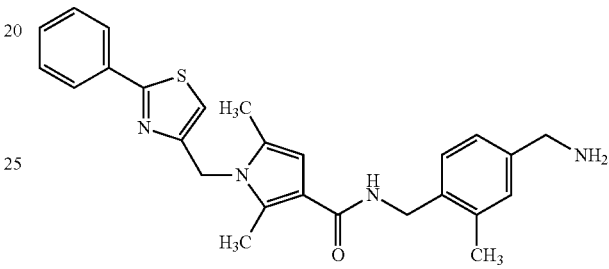

A. (4-Cyano-2-methyl-benzyl)-carbamic acid benzyl ester

4-Aminomethyl-3-methylbenzonitrile (1.0 g, 5.48 mmol) was dissolved in dichloromethane (50 mls) and the solution was cooled to 0° C. N,N-Diisopropylethylamine (1.56 g, 12.05 mmol) was added followed by benzyl chloroformate 1.12 g, 6.57 mmol) was added. After 3 days at 0° C. to room temperature the reaction mixture was diluted with chloroform, this solution was washed with sat NaHCO$_3$ (1×30 mls), water (1×30 mls), brine (1×30 mls), dried (Na$_2$SO$_4$) and evaporated in vacuo to give a brown oil identified as (4-cyano-2-methyl-benzyl)-carbamic acid benzyl ester (1.50 g, 5.35 mmol, 98%).

[M+H]+=281.25

B. [4-(tert-Butoxycarbonylamino-methyl)-2-methyl-benzyl]-carbamic acid benzyl ester (4-Cyano-2-methyl-benzyl)-carbamic acid benzyl ester (1.5 g, 5.35 mmol) was dissolved in methanol (75 mls). This solution was cooled to 0° C. Nickel (II) chloride hexahydrate (127 mg, 0.54 mmol) and di-tertbutyl dicarbonate (2.34 g, 10.70 mmol) were added followed by sodium borohydride (1.42 g, 37.56 mmol) portionwise. The reaction mixture was stirred at 0° C. to room temp for 3 days. The MeOH was removed by evaporation. The residue was dissolved in CHCl$_3$ (70 mls), washed with sat NaHCO$_3$ (1×30 mls), water (1×30 mls), brine (1×30 mls), dried (Na$_2$SO$_4$) and evaporated in vacuo to give a yellow oil. Purified by flash chromatography, (silica), eluant 40% Pet. Ether (60-80° C.), 60% EtOAc to give white solid identified as [4-(tert-butoxycarbonylamino-methyl)-2-methyl-benzyl]-carbamic acid benzyl ester (1.11 g, 2.38 mmol, 54%).

[M+H]+=285.32.

C. (4-Aminomethyl-3-methyl-benzyl)-carbamic acid tert-butyl ester

[4-(tert-Butoxycarbonylamino-methyl)-2-methyl-benzyl]-carbamic acid benzyl ester (130 mg, 0.34 mmol) was dissolved in methanol (40 mls). This solution was hydrogenated over 10% Pd/C (40 mg) at atmospheric pressure and room temperature for one hour after which time the catalyst was filtered off and washed with methanol (30 mls), the combined filtrates were evaporated in vacuo to give a white solid identified as (4-aminomethyl-3-methyl-benzyl)-carbamic acid tert-butyl ester (80 mg, 0.32 mmol, 95%).

D. [4-({[2,5-Dimethyl-1-(2-phenyl-thiazol-4-ylmethyl)-1H-pyrrole-3-carbonyl]-amino}-methyl)-3-methyl-benzyl]-carbamic acid tert-butyl ester 2,5-Dimethyl-1-(2-phenyl-thiazol-4-ylmethyl)-1H-pyrrole-3-carboxylic acid (100 mg, 0.32 mmol) was dissolved in CH$_2$Cl$_2$ (20 mls). This solution was cooled to 0° C. (4-Aminomethyl-3-methyl-benzyl)-carbamic acid tert-butyl ester (80 mg, 0.32 mmol) was added followed by HOBt (52 mg, 0.38 mmol) and triethylamine (162 mg, 1.60 mmol). Water soluble carbodiimide (86 mg, 0.45 mmol) was then added. After 18 hrs at 0° C. to room temperature reaction mixture was diluted with chloroform (200 mls) and washed with NaHCO$_3$ (1×50 mls), water (1×50 mls), brine (1×50 mls), dried (Na$_2$SO$_4$) and evaporated in vacuo. The residue was purified by flash chromatography (silica), eluant 50% Pet. Ether (60-80° C.), 50% EtOAc, fractions combined and evaporated in vacuo to give a white solid identified as [4-({[2,5-dimethyl-1-(2-phenyl-thiazol-4-ylmethyl)-1H-pyrrole-3-carbonyl]-amino}-methyl)-3-methyl-benzyl]-carbamic acid tert-butyl ester (105 mg, 0.19 mmol, 60%).

[M+H]$^+$=567.14.

E. 2,5-Dimethyl-1-(2-phenyl-thiazol-4-ylmethyl)-1H-pyrrole-3-carboxylic acid 4-aminomethyl-2-methyl-benzylamide

[4-({[2,5-Dimethyl-1-(2-phenyl-thiazol-4-ylmethyl)-1H-pyrrole-3-carbonyl]-amino}-methyl)-3-methyl-benzyl]-carbamic acid tert-butyl ester (105 mg, 0.93 mmol) was dissolved in methanol (20 mls) to which 4M HCl in dioxan (5 mls) was added. After three hours at room temperature the solvent was removed in vacuo and the residue was azeotroped from toluene. The free base was liberated with a mixture of dichloromethane, MeOH and NH$_3$ then evaporated. The residue was purified by flash chromatography (silica), eluant dichlromethane:MeOH:NH$_3$ (100:10:1). The residue freeze dried from acetonitrile and water to give an off white solid identified as 2,5-dimethyl-1-(2-phenyl-thiazol-4-ylmethyl)-1H-pyrrole-3-carboxylic acid 4-aminomethyl-2-methyl-benzylamide (58 mg, 0.13 mmol, 68%).

[M+H]+=445.17

$^1$H NMR: (d6-DMSO, δ: 2.26 (3H, s), 2.27 (3H, s), 2.55 (3H, s), 3.32 (2H, br s), 3.65 (2H, s), 4.30 (2H, s), 5.16 (2H, s), 6.31 (1H, s), 7.08-7.13 (3H, m), 7.27 (1H, s), 7.48-7.54 (3H, m), 7.87-7.92 (3H, m).

Example 3

2,5-Dimethyl-1-(2-phenyl-thiazol-4-ylmethyl)-1H-pyrrole-3-carboxylic acid 4-aminomethyl-2,6-dimethyl-benzylamide

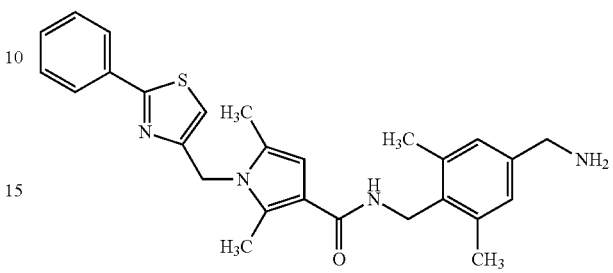

A. (4-Bromo-2,6-dimethyl-benzyl)-carbamic acid tert-butyl ester

4-Bromo-2,6-dimethylbenzonitrile (2.5 g, 11.9 mmol) was dissolved in methanol (150 mls). This solution was cooled to 0° C. Nickel (II) chloride hexahydrate (238 mg, 1.19 mmol) and di-tertbutyl dicarbonate (5.19 g, 23.80 mmol) were added followed by sodium borohydride (3.15 g, 83.30 mmol) portionwise. The reaction mixture was stirred at 0° C. to room temp for 3 days. The MeOH was removed by evaporation. The residue was dissolved in CHCl$_3$ (70 mls), washed with sat NaHCO$_3$ (1×30 mls), water (1×30 mls), brine (1×30 mls), dried (Na$_2$SO$_4$) and evaporated in vacuo to give a colourless oil identified as (4-bromo-2,6-dimethyl-benzyl)-carbamic acid tert-butyl ester (3.0 g, 9.55 mmol, 80%).

B. (4-Cyano-2,6-dimethyl-benzyl)-carbamic acid tert-butyl ester

To a degassed solution of (4-bromo-2,6-dimethyl-benzyl)-carbamic acid tert-butyl ester (3.0 g, 9.55 mmol) in N,N-dimethylacetamide (30 mls) was added zinc powder (75 mg, 1.15 mmol), zinc acetate (210 mg, 1.15 mmol), 1,1'-bis(diphenylphosphino) ferrocene (635 mg, 1.15 mmol), zinc cyanide (560 mg, 4.77 mmol), and tris(dibenzylideneacetone) dipalladium(0) (524 mg, 0.57 mmol). The reaction was heated at 120° C. for 4 hrs. After which the reaction mixture was cooled to room temperature and extra 1,1'-bis (diphenylphosphino) ferrocine (423 mg, 0.77 mmol) and tris(dibenzylideneacetone) dipalladium(0) (350 mg, 0.38 mmol) were added and the reaction was heated at 120° C. for a further 28 hrs. The reaction mixture was cooled to RT filtered through celite and washed with ethyl acetate (250 mls). The filtrate washed with sat NaHCO$_3$ (1×30 mls), water (1×30 mls), brine (1×30 mls), dried (Na$_2$SO$_4$) and evaporated in vacuo. The residue was purified by flash chromatography, (silica), eluant 80% Pet. Ether (60-80° C.), 20% EtOAc to give an off white solid identified as (4-cyano-2,6-dimethyl-benzyl)-carbamic acid tert-butyl ester (630 mg, 2.42 mmol, 25%).

[M+H]$^+$=261.06.

C. 4-Aminomethyl-3,5-dimethyl-benzonitrile Hydrochloride (4-Cyano-2,6-dimethyl-benzyl)-carbamic acid tert-butyl ester (630 mg, 2.42 mmol) was dissolved in 4M HCl in dioxan (10 mls). After one hour at room temperature the solvent was removed in vacuo to give a pale brown solid identified as 4-aminomethyl-3,5-dimethyl-benzonitrile hydrochloride (470 mg, 2.39 mmol, 99%).

D. (4-Cyano-2,6-dimethyl-benzyl)-carbamic acid benzyl ester

4-Aminomethyl-3,5-dimethyl-benzonitrile hydrochloride (470 mg, 2.39 mmol) was dissolved in dichloromethane (50 mls) and the solution was cooled to 0° C. N,N-Diisopropylethylamine (679 mg, 5.26 mmol) was added followed by benzyl chloroformate (489 mg, 2.87 mmol) was added. After one hour at 0° C. to room temperature the reaction mixture was diluted with chloroform, this solution was washed with sat NaHCO$_3$ (1×30 mls), water (1×30 mls), brine (1×30 mls), dried (Na$_2$SO$_4$) and evaporated in vacuo to give a brown oil identified as (4-cyano-2,6-dimethyl-benzyl)-carbamic acid benzyl ester (700 mg, 2.38 mmol, 99%).
[M+H]$^+$=295.04

E. [4-(tert-Butoxycarbonylamino-methyl)-2,6-dimethyl-benzyl]-carbamic acid benzyl ester (4-Cyano-2,6-dimethyl-benzyl)-carbamic acid benzyl ester (700 mg, 2.38 mmol) was dissolved in methanol (75 mls). This solution was cooled to 0° C. Nickel (II) chloride hexahydrate (57 mg, 0.24 mmol) and di-tertbutyl dicarbonate (1.04 g, 4.76 mmol) were added followed by sodium borohydride (630 mg, 16.65 mmol) portionwise. The reaction mixture was stirred at 0° C. to room temp for 3 days. The MeOH was removed by evaporation. The residue was dissolved in CHCl$_3$ (70 ml), washed with sat NaHCO$_3$ (1×30 mls), water (1×30 mls), brine (1×30 mls), dried (Na$_2$SO$_4$) and evaporated in vacuo. The residue was purified by flash chromatography, (silica), eluant 65% Pet. Ether (60-80° C.), 35% EtOAc to give an off white solid identified as [4-(tert-butoxycarbonylamino-methyl)-2,6-dimethyl-benzyl]-carbamic acid benzyl ester (600 mg, 1.51 mmol, 63%).
[M+H]$^+$=421.05 (M+Na).

F. (4-Aminomethyl-3,5-dimethyl-benzyl)-carbamic acid tert-butyl ester

[4-(tert-Butoxycarbonylamino-methyl)-2,6-dimethyl-benzyl]-carbamic acid benzyl ester (600 mg, 1.51 mmol) was dissolved in methanol (60 mls). This solution was hydrogenated over 10% Pd/C (100 mg) at atmospheric pressure and room temperature for one hour after which time the catalyst was filtered off and washed with methanol (30 mls), the combined filtrates were evaporated in vacuo to give a white solid identified as (4-aminomethyl-3,5-dimethyl-benzyl)-carbamic acid tert-butyl ester (350 mg, 1.32 mmol, 88%).
[M+H]$^+$=287.07 (M+Na).

G. [4-({[2,5-Dimethyl-1-(2-phenyl-thiazol-4-ylmethyl)-1H-pyrrole-3-carbonyl]-amino}-methyl)-3,5-dimethyl-benzyl]-carbamic acid tert-butyl ester 2,5-Dimethyl-1-(2-phenyl-thiazol-4-ylmethyl)-1H-pyrrole-3-carboxylic acid (118 mg, 0.38 mmol) was dissolved in CH$_2$Cl$_2$ (20 mls). This solution was cooled to 0° C. (4-(4-Aminomethyl-3,5-dimethyl-benzyl)-carbamic acid tert-butyl ester (100 mg, 0.38 mmol) was added followed by HOBt (61 mg, 0.45 mmol) and triethylamine (191 mg, 1.89 mmol). Water soluble carbodiimide (102 mg, 0.53 mmol) was then added. After 18 hrs at 0° C. to room temperature reaction mixture was diluted with chloroform (200 mls) and washed with NaHCO$_3$ (1×50 mls), water (1×50 mls), brine (1×50 mls), dried (Na$_2$SO$_4$) and evaporated in vacuo. The residue was purified by flash chromatography (silica), eluant 50% Pet. Ether (60-80° C.), 50% EtOAc, fractions combined and evaporated in vacuo to give a white solid identified as [4-({[2,5-dimethyl-1-(2-phenyl-thiazol-4-ylmethyl)-1H-pyrrole-3-carbonyl]-amino}-methyl)-3,5-dimethyl-benzyl]-carbamic acid tert-butyl ester (110 mg, 0.20 mmol, 52%).
[M+H]$^+$=567.14.

H. 2,5-Dimethyl-1-(2-phenyl-thiazol-4-ylmethyl)-1H-pyrrole-3-carboxylic acid 4-aminomethyl-2,6-dimethyl-benzylamide

[4-({[2,5-Dimethyl-1-(2-phenyl-thiazol-4-ylmethyl)-1H-pyrrole-3-carbonyl]-amino}-methyl)-3,5-dimethyl-benzyl]-carbamic acid tert-butyl ester (110 mg, 0.20 mmol) was dissolved in methanol (20 mls) to which 4M HCl in dioxan (5 mls) was added. After three hours at room temperature the solvent was removed in vacuo and the residue was azeotroped from toluene. The free base was liberated with a mixture of dichloromethane, MeOH and NH$_3$ then evaporated. The residue was purified by flash chromatography (silica), eluant dichloromethane:MeOH:NH$_3$ (100:10:1). The residue freeze dried from acetonitrile and water to give an off white solid identified as 2,5-dimethyl-1-(2-phenyl-thiazol-4-ylmethyl)-1H-pyrrole-3-carboxylic acid 4-aminomethyl-2,6-dimethyl-benzylamide (77 mg, 0.17 mmol, 85%).
[M+H]$^+$=459.09
$^1$H NMR: (d6-DMSO), δ: 2.22 (3H, s), 2.34 (6H, s), 2.54 (3H, s), 3.74 (2H, s), 4.34 (2H, d, J=5.0 Hz), 5.15 (2H, s), 5.44 (2H, br s), 6.24 (1H, s), 7.00 (2H, s), 7.25 (1H, s), 7.45 (1H, t, J=5.1 Hz), 7.49-7.51 (3H, m), 7.88-7.91 (2H, m).

Example 4

2,5-Dimethyl-1-(2-phenyl-thiazol-4-ylmethyl)-1H-pyrrole-3-carboxylic acid 4-(1-amino-cyclopropyl)-benzylamide

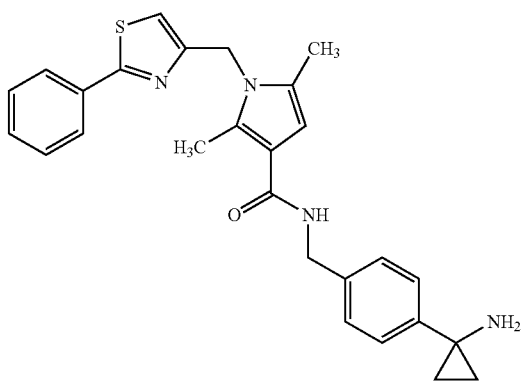 [SMILES: Cc1cc(C(=O)NCc2ccc(C3(N)CC3)cc2)c(C)n1Cc1csc(-c2ccccc2)n1]

A. 4-(1-Amino-cyclopropyl)-benzonitrile

In oven dried glassware under an atmosphere of nitrogen a solution of 1,4-dicyanobenzene (2.50 g, 20 mmol) in anhydrous dichloromethane (80 mls) was cooled to −70° C.

Titanium isopropoxide (6.1 g, 21.46 mmol) was added followed by dropwise addition of 3M solution of ethyl magnesium bromide in diethyl ether (14.37 mls, 43 mmol). The reaction was stirred at −70° C. for 10 min and then allowed to warm to room temperature). After 1 hour boron trifluoride etherate (5.54 g, 39.02 mmol) was added and the reaction stirred at room temperature for 18 hours. The reaction was quenched with NH$_4$Cl and then the pH adjusted to 9-10 with 1M NaOH. The layers were separated and the aqueous extracted dichloromethane (5×20 mls) then with ethyl acetate (3×20 mls). Organic layers were combined and dried over Na$_2$SO$_4$, filtered and concentrated. The residue was purified by flash chromatography (silica), eluant dichloromethane/MeOH/NH$_4$OH (99:1:1, 98:2:1, 97:3:1, 95:5:1) giving a yellow oil identified as 4-(1-amino-cyclopropyl)-benzonitrile (1.61 g, 10 mmol, 52%).

$^1$H NMR: (CDCl$_3$), δ: 1.07-1.10 (2H, m), 1.21-1.24 (2H, m), 1.86 (2H, br, s), 7.39 (2H, dt, J=8.4, 1.9 Hz), 7.61 (2H, dt, J=8.4, 1.9 Hz).

B. [1-(4-Cyano-phenyl)-cyclopropyl]-carbamic acid benzyl ester 4-(1-Amino-cyclopropyl)-benzonitrile (1.61 g, 10.18 mmol) was dissolved in dichloromethane (250 mls) and the solution was cooled to 0° C. N,N-Diisopropylethylamine (2.89 g, 22.39 mmol) was added followed by benzyl chloroformate 2.08 g, 12.21 mmol) was added. After 18 hours at 0° C. to room temperature the reaction mixture was diluted with chloroform, this solution was washed with sat NaHCO$_3$ (1×30 mls), water (1×30 mls), brine (1×30 mls), dried (Na$_2$SO$_4$) and evaporated in vacuo. The residue was purified by flash chromatography (silica), eluant 90% Pet. Ether (60-80° C.), 10% EtOAc, fractions combined and evaporated in vacuo to give a to give a yellow oil identified as [1-(4-cyano-phenyl)-cyclopropyl]-carbamic acid benzyl ester (1.33 g, 4.55 mmol, 45%).

[M+H]$^+$=293.04

$^1$H NMR: (CDCl$_3$), δ: 1.24 (6H, t, J=7.2 Hz), 3.02 (4H, q, J=7.2 Hz), 4.70 (2H, s), 7.34-7.37 (5H, m), 7.77 (2H, d, J=8.4 Hz), 8.04 (2H, d, J=8.6 Hz).

C. {1-[4-(tert-Butoxycarbonylamino-methyl)-phenyl]-cyclopropyl}-carbamic acid benzyl ester

[1-(4-Cyano-phenyl)-cyclopropyl]-carbamic acid benzyl ester (1.33 g, 4.55 mmol) was dissolved in methanol (100 mls). This solution was cooled to 0° C. Nickel (II) chloride hexahydrate (108 mg, 0.46 mmol) and di-tertbutyl dicarbonate (1.99 g, 9.10 mmol) were added followed by sodium borohydride (1.21 g, 31.85 mmol) portionwise. The reaction mixture was stirred at 0° C. to room temp for 18 hours. The MeOH was removed by evaporation. The residue was dissolved in CHCl$_3$ (70 mls), washed with sat NaHCO$_3$ (1×30 mls), water (1×30 mls), brine (1×30 mls), dried (Na$_2$SO$_4$) and evaporated in vacuo to give a yellow oil. Purified by flash chromatography, (silica), eluant 30% Pet. Ether (60-80° C.), 70% EtOAc to give white solid identified as {1-[4-(tert-butoxycarbonylamino-methyl)-phenyl]-cyclopropyl}-carbamic acid benzyl ester (1.06 g, 2.67 mmol, 59%).

[M+H]$^+$=419.2 (M+Na).

D. [1-(4-Aminomethyl-phenyl)-cyclopropyl]-carbamic acid benzyl ester Hydrochloride {1-[4-(tert-butoxycarbonylamino-methyl)-phenyl]-cyclopropyl}-carbamic acid benzyl ester (90 mg, 0.23 mmol) was dissolved in 4M HCl in dioxan (10 mls). After 3 hours at room temperature the solvent was removed in vacuo to give a yellow solid identified as [1-(4-aminomethyl-phenyl)-cyclopropyl]-carbamic acid benzyl ester hydrochloride (84 mg, 0.23 mmol, 100%).

[M+H]$^+$=318.97 (M+Na).

E. {1-[4-({[2,5-Dimethyl-1-(2-phenyl-thiazol-4-ylmethyl)-1H-pyrrole-3-carbonyl]-amino}-methyl)-phenyl]-cyclopropyl}-carbamic acid benzyl ester 2,5-Dimethyl-1-(2-phenyl-thiazol-4-ylmethyl)-1H-pyrrole-3-carboxylic acid (78 mg, 0.25 mmol) was dissolved in CH$_2$Cl$_2$ (20 mls). This solution was cooled to 0° C. [1-(4-Aminomethyl-phenyl)-cyclopropyl]-carbamic acid benzyl ester hydrochloride (84 mg, 0.23 mmol) was added followed by HOBt (37 mg, 0.27 mmol) and triethylamine (115 mg, 1.14 mmol). Water soluble carbodiimide (61 mg, 0.32 mmol) was then added. After 18 hrs at 0° C. to room temperature reaction mixture was diluted with chloroform (100 mls) and washed with NaHCO$_3$ (1×20 mls), water (1×20 mls), brine (1×20 mls), dried (Na$_2$SO$_4$) and evaporated in vacuo. The residue was purified by flash chromatography (silica), eluant 50% Pet. Ether (60-80° C.), 50% EtOAc, fractions combined and evaporated in vacuo to give a white solid identified as {1-[4-({[2,5-dimethyl-1-(2-phenyl-thiazol-4-ylmethyl)-1H-pyrrole-3-carbonyl]-amino}-methyl)-phenyl]-cyclopropyl}-carbamic acid benzyl ester (66 mg, 0.11 mmol, 49%).

[M+H]$^+$=613.02 (M+Na).

F. 2,5-Dimethyl-1-(2-phenyl-thiazol-4-ylmethyl)-1H-pyrrole-3-carboxylic acid 4-(1-amino-cyclopropyl)-benzylamide {1-[4-({[2,5-Dimethyl-1-(2-phenyl-thiazol-4-ylmethyl)-1H-pyrrole-3-carbonyl]-amino}-methyl)-phenyl]-cyclopropyl}-carbamic acid benzyl ester (70 mg, 0.12 mmol) was dissolved in methanol (40 mls). This solution was hydrogenated over 10% Pd/C (10 mg) at atmospheric pressure and room temperature for 5 hours after which time the catalyst was filtered off and washed with methanol (30 mls), the combined filtrates were evaporated in vacuo and freeze dried from acetonitrile and water to give a white solid identified as 2,5-dimethyl-1-(2-phenyl-thiazol-4-ylmethyl)-1H-pyrrole-3-carboxylic acid 4-(1-amino-cyclopropyl)-benzylamide (21 mg, 0.046 mmol, 38%).

[M+H]$^+$=480.16.

$^1$H NMR: (d6-DMSO) δ: 0.75 (2H, t, J=7.4 Hz), 1.45-1.57 (2H, m), 2.25 (3H, s), 2.55 (3H, s), 3.63 (1H, t, J=6.7 Hz), 4.32 (2H, d, J=6.1 Hz), 5.16 (2H, s), 6.29 (2H, s), 7.18 (2H, d, J=8.0 Hz), 7.23 (2H, d, J=8.0 Hz), 7.25 (1H, s), 7.49 (2H, d, J=1.8 Hz), 7.50-7.51 (1H, m), 7.89 (1H, d, J=1.7 Hz), 7.91 (1H, d, J=2.6 Hz), 8.03 (1H, t, J=6.1 Hz).

Reference Example 5

1-[4-(2-Oxo-2H-pyridin-1-ylmethyl)-benzyl]-1H-pyrazole-4-carboxylic acid 4-aminomethyl-benzyl-amide

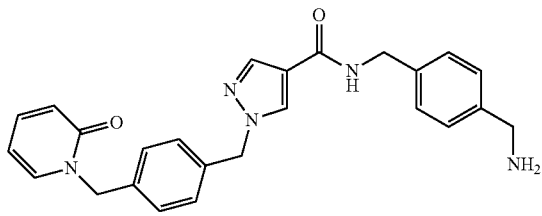 [SMILES: NCc1ccc(CNC(=O)c2cnn(Cc3ccc(Cn4ccccc4=O)cc3)c2)cc1]

A. 1-(4-Chloromethyl-benzyl)-1H-pyrazole-4-carboxylic acid ethyl ester

Polymer-supported triphenylphosphine (3.0 mmol/g, 3 equiv, 1.0 g) was swollen in THF/dichloromethane (1:1, 100 mls) under a nitrogen atmosphere. Ethyl 1H-pyrazole-4-carboxylate (500 mg, 3.57 mmol) and 4-(chloromethyl) benzyl alcohol (671 mg, 4.28 mmol) were added followed by a solution of diisopropyl azodicarboxylate (1.08 g, 5.35 mmol) in THF/dichloromethane (1:1, 10 mls) over a period of 30 mins. The reaction mixture was stirred at room temperature for 18 hours, the mixture was filtered through celite and the resin was washed with 3 cycles of dichloromethane/methanol (15 mls). The combined filtrates were evaporated in vacuo and triturated with ethanol to give a white solid identified as 1-(4-chloromethyl-benzyl)-1H-pyrazole-4-carboxylic acid ethyl ester (741 mg, 2.66 mmol, 75%).

[M+H]$^+$=279.05

B. 1-[4-(2-Oxo-2H-pyridin-1-ylmethyl)-benzyl]-1H-pyrazole-4-carboxylic acid ethyl ester 1-(4-Chloromethyl-benzyl)-1H-pyrazole-4-carboxylic acid ethyl ester (300 mg, 1.076 mmol) was dissolved in acetone (50 mls) 2-hydroxypyridine (123 mg, 0.001 mmol) and potassium carbonate (446 mg, 0.003 mmol) were added and the reaction mixture was stirred at 50° C. for 3 hours after which time the solvent was removed in vacuo and the residue taken up in EtOAc (100 mls), this solution was washed with water (1×30 mls), brine (1×30 mls), dried (Na$_2$SO$_4$) and evaporated in vacuo. The residue was purified by flash chromatography (silica), eluant 3% MeOH, 97% CHCl$_3$, fractions combined and evaporated in vacuo to give a colourless oil identified as 1-[4-(2-oxo-2H-pyridin-1-ylmethyl)-benzyl]-1H-pyrazole-4-carboxylic acid ethyl ester (310 mg, 0.92, 85%).

[M+H]$^+$=337.78, 350.84 (M+Na).

C. 1-[4-(2-Oxo-2H-pyridin-1-ylmethyl)-benzyl]-1H-pyrazole-4-carboxylic acid 1-[4-(2-Oxo-2H-pyridin-1-ylmethyl)-benzyl]-1H-pyrazole-4-carboxylic acid ethyl ester (310 mg, 0.92 mmol) was dissolved in THF (50 mls) and water (5 mls) lithium hydroxide (110 mg, 4.6 mmol) was added. The reaction mixture was stirred at 50° C. for 18 hours after which time the solvent was concentrated in vacuo and the residue taken up in EtOAc (50 mls), the aqueous layer was separated, acidified with 1M HCl to pH2 and extracted CHCl$_3$ (3×50 mls) the combined extracts were washed with water (1×30 mls), brine (1×30 mls), dried (Na$_2$SO$_4$) and evaporated in vacuo. The residue was purified by flash chromatography (silica), eluant 3% MeOH, 97% CHCl$_3$, fractions combined and evaporated in vacuo to give a colourless oil identified as 1-[4-(2-oxo-2H-pyridin-1-ylmethyl)-benzyl]-1H-pyrazole-4-carboxylic acid (140 mg, 0.453 mmol, 49%).

[M+H]$^+$=309.93

D. {4-[({1-[4-(2-Oxo-2H-pyridin-1-ylmethyl)-benzyl]-1H-pyrazole-4-carbonyl}-amino)-methyl]-benzyl}-carbamic acid tert-butyl ester 1-[4-(2-Oxo-2H-pyridin-1-ylmethyl)-benzyl]-1H-pyrazole-4-carboxylic acid (130 mg, 0.42 mmol) was dissolved in CH$_2$Cl$_2$ (50 mls) and DMF (2.5 mls). This solution was cooled to 0° C. tert-Butyl 4-(Aminomethyl)benzylcarbamate (119 mg, 0.50 mmol) was added followed by HOBt (62 mg, 0.46 mmol) and triethylamine (128 mg, 1.27 mmol). Water soluble carbodiimide (97 mg, 0.50 mmol) was then added. After 18 hours at 0° C. to room temperature reaction mixture was diluted with chloroform (400 mls) washed with 0.3M KHSO$_4$ (1×30 mls), NaHCO$_3$ (1×30 mls), water (1×30 mls), brine (1×30 mls), dried (Na$_2$SO$_4$) and evaporated in vacuo. The residue was purified by flash chromatography (silica), eluant 6% MeOH, 94% CHCl$_3$, fractions combined and evaporated in vacuo to give a white solid identified as {4-[({1-[4-(2-oxo-2H-pyridin-1-ylmethyl)-benzyl]-1H-pyrazole-4-carbonyl}-amino)-methyl]-benzyl}-carbamic acid tert-butyl ester (156 mg, 0.296 mmol, 70%).

[M+H]$^+$=550.45

E. 1-[4-(2-Oxo-2H-pyridin-1-ylmethyl)-benzyl]-1H-pyrazole-4-carboxylic acid 4-aminomethyl-benzyl-amide Hydrochloride {4-[({1-[4-(2-Oxo-2H-pyridin-1-ylmethyl)-benzyl]-1H-pyrazole-4-carbonyl}-amino)-methyl]-benzyl}-carbamic acid tert-butyl ester (52 mg, 0.10 mmol) was dissolved in 4M HCl in dioxan (25 mls). After one hour at room temperature the solvent was removed in vacuo. The residue was slurried with acetone and the solid was filtered off to give a white solid identified as 1-[4-(2-oxo-2H-pyridin-1-ylmethyl)-benzyl]-1H-pyrazole-4-carboxylic acid 4-aminomethyl-benzylamide hydrochloride (89 mg, 0.19 mmol, 47%).

[M+H]$^+$=428.32

$^1$H NMR: (d6-DMSO), δ: 3.97 (2H, q, J=5.72 Hz), 4.38 (2H, dq, J=6.06 Hz), 5.08 (2H, s), 5.31 (2H, s), 6.23 (1H, q, J=6.34 Hz), 6.40 (1H, d, J=5.72 Hz), 7.22-7.32 (6H, m), 7.41-7.44 (2H, m), 7.77 (1H, d, J=6.62 Hz), 7.91 (1H, s), 8.27 (1H, s), 8.39 (3H, s, br), 8.71-8.74 (1H, m).

Reference Example 6

1-[4-(2-Oxo-2H-pyridin-1-ylmethyl)-benzyl]-1H-[1,2,3]triazole-4-carboxylic acid 4-aminomethyl-benzylamide

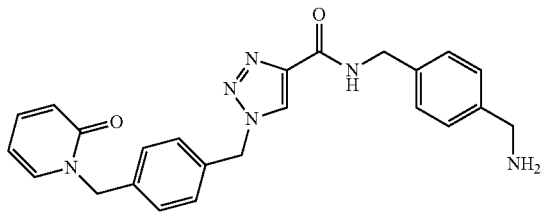 [SMILES: NCc1ccc(CNC(=O)c2cn(Cc3ccc(Cn4ccccc4=O)cc3)nn2)cc1]

A. 1-(4-Hydroxymethyl-benzyl)-1H-pyridin-2-one 4-(Chloromethyl)benzylalcohol (1.0 g, 6.38 mmol) was dissolved in acetone (50 mls) 2-hydroxypyridine (729 mg, 7.66 mmol) and potassium carbonate (2.65 g, 19.20 mmol) were added and the reaction mixture was stirred at 50° C. for 3 hours after which time the solvent was removed in vacuo and the residue taken up in chloroform (100 mls), this solution was washed with water (1×30 mls), brine (1×30 mls), dried ($Na_2SO_4$) and evaporated in vacuo. The residue was purified by flash chromatography (silica), eluant 3% MeOH, 97% $CHCl_3$, fractions combined and evaporated in vacuo to give a white solid identified as 1-(4-hydroxymethyl-benzyl)-1H-pyridin-2-one (1.10 g, 5.11, 80%)

$[M+H]^+$=238.09 (M+Na)

B. 1-(4-Azidomethyl-benzyl)-1H-pyridin-2-one 1-(4-Hydroxymethyl-benzyl)-1H-pyridin-2-one (570 mg, 2.65 mmol) and DBU (806 mg, 5.30 mmol) were dissolved in DMF (20 mls). Diphenylphosphoryl azide (1.09 g, 3.97 mmol) was added and the reaction mixture was stirred at room temperature for 3 hours after which time the reaction mixture was diluted with EtOAc (100 mls), this solution was washed with water (1×30 mls), brine (1×30 mls), dried ($Na_2SO_4$) and evaporated in vacuo. The residue was purified by flash chromatography (silica), eluant 3% MeOH, 97% $CHCl_3$, fractions combined and evaporated in vacuo to give a white foamy solid identified as 1-(4-azidomethyl-benzyl)-1H-pyridin-2-one (430 mg, 1.79 mmol, 68%).

$[M+H]^+$=360.90 (M+Na).

C. 1-[4-(2-Oxo-2H-pyridin-1-ylmethyl)-benzyl]-1H-[1,2,3]triazole-4-carboxylic acid ethyl ester 1-(4-Azidomethyl-benzyl)-1H-pyridin-2-one (340 mg, 1.41 mmol), ethyl propiolate (139 mg, 1.41 mmol), (+)-sodium L-ascorbate (280 mg, 1.41 mmol) and copper (II) sulphate pentahydrate (71 mg, 0.28 mmol) were dissolved in tert-butanol (20 mls) and water (5 mls). The reaction mixture was stirred at room temperature for 18 hours after which time the reaction mixture was diluted with chloroform (100 mls), this solution was washed with water (1×30 mls), brine (1×30 mls), dried ($Na_2SO_4$) and evaporated in vacuo. The residue was triturated with ethyl acetate and pet ether 60-80 to give a white solid identified as 1-[4-(2-oxo-2H-pyridin-1-ylmethyl)-benzyl]-1H-[1,2,3]triazole-4-carboxylic acid ethyl ester (110 mg, 0.33 mmol, 23%).

$[M+H]^+$=486.18

D. 1-[4-(2-Oxo-2H-pyridin-1-ylmethyl)-benzyl]-1H-[1,2,3]triazole-4-carboxylic acid 1-[4-(2-Oxo-2H-pyridin-1-ylmethyl)-benzyl]-1H-[1,2,3]triazole-4-carboxylic acid ethyl ester (110 mg, 0.32 mmol) was dissolved in THF (50 mls) and water (5 mls), lithium hydroxide (39 mg, 1.62 mmol) was added. The reaction mixture was stirred at 50° C. for 18 hours after which time the solvent was concentrated in vacuo and the residue taken up in EtOAc (50 mls), the aqueous layer was separated, acidified with 1M HCl to pH2 and extracted $CHCl_3$ (3×50 mls) the combined extracts were washed with water (1×30 mls), brine (1×30 mls), dried ($Na_2SO_4$) and evaporated in vacuo. The residue was purified by flash chromatography (silica), eluant 3% MeOH, 97% $CHCl_3$, fractions combined and evaporated in vacuo to give a colourless oil identified as 1-[4-(2-oxo-2H-pyridin-1-ylmethyl)-benzyl]-1H-[1,2,3]triazole-4-carboxylic acid (80 mg, 0.26 mmol, 79%).

E. {4-[({1-[4-(2-Oxo-2H-pyridin-1-ylmethyl)-benzyl]-1H-[1,2,3]triazole-4-carbonyl}-amino)-methyl]-benzyl}-carbamic acid tert-butyl ester 1-[4-(2-Oxo-2H-pyridin-1-ylmethyl)-benzyl]-1H-[1,2,3]triazole-4-carboxylic acid (80 mg, 0.26 mmol) was dissolved in $CH_2Cl_2$ (50 mls) and DMF (2.5 mls). This solution was cooled to 0° C. tert-Butyl 4-(aminomethyl)benzylcarbamate (73 mg, 0.31 mmol) was added followed by HOBt (38 mg, 0.28 mmol) and triethylamine (78 mg, 0.77 mmol). Water soluble carbodiimide (59 mg, 0.31 mmol) was then added. After 18 hours at 0° C. to room temperature reaction mixture was diluted with chloroform (400 mls) washed with 0.3M $KHSO_4$ (1×30 mls), $NaHCO_3$ (1×30 mls), water (1×30 mls), brine (1×30 mls), dried ($Na_2SO_4$) and evaporated in vacuo giving a yellow oil. The residue was purified by flash chromatography (silica), eluant 6% MeOH, 94% $CHCl_3$, fractions combined and evaporated in vacuo to give a white solid identified as {4-[({1-[4-(2-oxo-2H-pyridin-1-ylmethyl)-benzyl]-1H-[1,2,3]triazole-4-carbonyl}-amino)-methyl]-benzyl}-carbamic acid tert-butyl ester (85 mg, 0.166 mmol, 62%).

$[M+H]^+$=550.45

F. 1-[4-(2-Oxo-2H-pyridin-1-ylmethyl)-benzyl]-1H-[1,2,3]triazole-4-carboxylic acid 4-aminomethyl-benzylamide Hydrochloride {4-[({1-[4-(2-Oxo-2H-pyridin-1-ylmethyl)-benzyl]-1H-[1,2,3]triazole-4-carbonyl}-amino)-methyl]-benzyl}-carbamic acid tert-butyl ester (85 mg, 0.16 mmol) was dissolved in 4M HCl in dioxan (25 mls). After one hour at room temperature the solvent was removed in vacuo. The residue was slurried with acetone and the solid was filtered off to give a white solid identified 1-[4-(2-oxo-2H-pyridin-1-ylmethyl)-benzyl]-1H-[1,2,3]triazole-4-carboxylic acid 4-aminomethyl-benzylamide hydrochloride (76 mg, 0.18 mmol, 60%).

$[M+H]^+$=429.10

$^1$H NMR: (d6-DMSO), δ: 4.00 (2H, q, J=5.72 Hz), 4.43 (2H, q, J=6.25 Hz), 5.08 (2H, s), 5.31 (2H, s), 6.23 (1H, q, J=6.52 Hz), 6.40 (1H, d, J=8.92 Hz), 7.27-7.48 (7H, m), 7.77 (1H, q, J=8.82 Hz), 7.91 (1H, s), 8.21 (3H, s, br), 8.64 (1H, s), 9.12 (1H, t, J=5.83 Hz).

Reference Example 7

1-(2-Methyl-quinolin-6-ylmethyl)-1H-pyrazole-4-carboxylic acid 4-aminomethyl-benzylamide

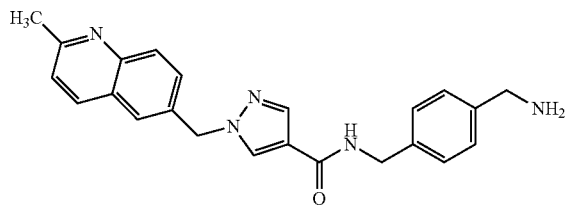 [SMILES: Cc1ccc2cc(Cn3cc(C(=O)NCc4ccc(CN)cc4)cn3)ccc2n1]

A. (4-{[(1H-Pyrazole-4-carbonyl)-amino]-methyl}-benzyl)-carbamic acid tert-butyl ester 4-Pyrazolecarboxylic acid (400 mg, 3.57 mmol) was dissolved in CH$_2$Cl$_2$ (50 mls) and DMF (2.5 mls). This solution was cooled to 0° C. tert-Butyl 4-(aminomethyl) benzylcarbamate (1.01 g, 4.28 mmol) was added followed by HOBt (530 mg, 3.93 mmol) and triethylamine (1.08 g, 10.71 mmol). Water soluble carbodiimide (821 mg, 4.28 mmol) was then added. After 18 hours at 0° C. to room temperature reaction mixture was diluted with chloroform (400 mls) washed with 0.3M KHSO$_4$ (1×30 mls), NaHCO$_3$ (1×30 mls), water (1×30 mls), brine (1×30 mls), dried (Na$_2$SO$_4$) and evaporated in vacuo giving a yellow oil. The residue was purified by flash chromatography (silica), eluant 7% MeOH, 93% CHCl$_3$, fractions combined and evaporated in vacuo to give a white solid identified as (4-{[(1H-pyrazole-4-carbonyl)-amino]-methyl}-benzyl)-carbamic acid tert-butyl ester (1.10 g, 3.33 mmol, 93%).

[M+H]$^+$=352.95 (M+Na)

B. (2-Methyl-quinolin-6-yl)-methanol

2-Methyl-quinoline-6-carboxylic acid (1.0 g, 5.34 mmol) was dissolved in THF (100 mls), this solution was cooled to −20° C., to this solution was added triethylamine (1.62 g, 16.03 mmol) and isobutyl chloroformate (875 mg, 6.41 mmol). The reaction mixture was stirred at −20° C. for 20 mins and then poured into a solution of sodium borohydride (1.0 g, 26.71 mmol) in water (10 mls) at 0° C. The reaction mixture was stirred at 0° C. to room temperature for 18 hours and diluted with EtOAc (200 mls) 0.3M KHSO$_4$ (1×50 mls), water (1×50 mls), brine (1×50 mls), dried (Na$_2$SO$_4$) and evaporated in vacuo to give a white solid. The solid were triturated with EtOAc/Pet Ether 60-80° C. to give a white solid identified as (2-methyl-quinolin-6-yl)-methanol (890 mg, 5.14 mmol, 96%).

[M+H]$^+$=174.24

C. 6-Bromomethyl-2-methyl-quinoline (2-Methyl-quinolin-6-yl)-methanol (150 mg, 0.87 mmol) was dissolved in dichloromethane (50 mls). To this solution was added phosphorous tribromide (215 mg, 2.13 mmol) The reaction mixture was stirred at room temperature for 18 hours and diluted with CHCl$_3$ (100 mls) the filtrate was washed with sat. NaHCO$_3$ (1×30 mls), water (1×30 mls), brine (1×30 mls), dried (Na$_2$SO$_4$) and evaporated in vacuo to give a white solid which was identified as 6-bromomethyl-2-methyl-quinoline (180 mg, 0.76 mmol, 88%).

[M+H]$^+$=235.96

D. [4-({[1-(2-Methyl-quinolin-6-ylmethyl)-1H-pyrazole-4-carbonyl]-amino}-methyl)-benzyl]-carbamic acid tert-butyl ester 6-Bromomethyl-2-methyl-quinoline (180 mg, 0.76 mmol) was dissolved in DMF (10 mls). (4-{[(1H-Pyrazole-4-carbonyl)-amino]-methyl}-benzyl)-carbamic acid tert-butyl ester (302 mg, 0.915 mmol) and cesium carbonate (745 mg, 2.29 mmol) were added and the reaction mixture was stirred at 50° C. for 18 hours after which time the reaction mixture was diluted with EtOAc (100 mls), this solution was washed with water (1×30 mls), brine (1×30 mls), dried (Na$_2$SO$_4$) and evaporated in vacuo. The residue was purified by flash chromatography (silica), eluant 3% MeOH, 97% CHCl$_3$, fractions combined and evaporated in vacuo to give a white foamy solid identified as [4-({[1-(2-methyl-quinolin-6-ylmethyl)-1H-pyrazole-4-carbonyl]-amino}-methyl)-benzyl]-carbamic acid tert-butyl ester (145 mg, 0.30 mmol, 39%).

[M+H]$^+$=486.18

E. 1-(2-Methyl-quinolin-6-ylmethyl)-1H-pyrazole-4-carboxylic acid 4-aminomethyl-benzylamide Hydrochloride

[4-({[1-(2-Methyl-quinolin-6-ylmethyl)-1H-pyrazole-4-carbonyl]-amino}-methyl)-benzyl]-carbamic acid tert-butyl ester (145 mg, 0.30 mmol) was dissolved in 4M HCl in dioxan (25 mls). After one hour at room temperature the solvent was removed in vacuo. The residue was slurried with acetone and the solid was filtered off to give a white solid identified as 1-(2-methyl-quinolin-6-ylmethyl)-1H-pyrazole-4-carboxylic acid 4-aminomethyl-benzylamide hydrochloride (76 mg, 0.18 mmol, 60%).

[M+H]$^+$=385.94

$^1$H NMR: (d6-DMSO), δ: 2.97 (3H, s), 3.98 (2H, q, J=5.53 Hz), 4.40 (2H, d, J=6.00 Hz), 5.66 (2H, s), 7.32 (2H, d, J=8.02 Hz), 7.42 (2H, d, J=8.30 Hz), 7.94-7.99 (1H, m), 8.00 (1H, s), 8.10 (1H, s), 8.37-8.43 (5H, m), 8.82 (1H, t, J=6.09 Hz), 9.00 (1H, d, J=8.60 Hz).

The compounds in the following tables were synthesised as described for Examples 1 to 4 and reference examples 5-7.

TABLE 1

| Example No | A | Free Base MW | [M + H]$^+$ |
|---|---|---|---|
| 8 | (3-pyridyl-thiophene) | 430.6 | 431.29 |

TABLE 1-continued

[Structure: 1-(A-CH2)-2,5-dimethyl-N-(4-(aminomethyl)benzyl)-1H-pyrrole-3-carboxamide]

| Example No | A | Free Base MW | [M + H]+ |
|---|---|---|---|
| 9 | 2-phenyl-thiophen-4-yl | 429.6 | 430.1 |
| 10 | 2-phenyl-thiophen-4-yl (isomer) | 429.6 | 430.16 |
| 11 | 3-phenyl-isoxazol-5-yl | 414.5 | 437.2 (M + Na) |
| 12 | benzothiazol-2-yl | 404.5 | 405.19 |
| 13 | 3-(pyridin-3-yl)-thiophen-5-yl | 430.6 | 431.17 |
| 14 | 2-(pyridin-4-yl)-thiophen-5-yl | 430.6 | 431.36 |
| 15 | 6-morpholinopyridin-2-yl | 433.5 | 434.24 |
| 16 | 6-phenylpyridin-2-yl | 424.5 | 425.35 |
| 17 | 6-(pyridin-3-yl)pyridin-2-yl | 425.5 | 426.23 |
| 18 | 2-phenyloxazol-4-yl | 414.5 | 415.24 |
| 19 | 2-phenyl-5-methyloxazol-4-yl | 428.5 | 429.42 |

TABLE 2

| Example No. | G6 | Free Base MW | [M + H]+ |
|---|---|---|---|
| 20 | H | 353.5 | 353.87 |
| 21 | pyridin-3-yl | 430.6 | 431.16 |
| 22 | phenyl | 429.6 | 430.15 |
| 23 | 2-methylthiazol-4-yl | 450.6 | 451.16 |

TABLE 3

| Example No | G7 | R6 | R7 | Free Base MW | [M + H]+ |
|---|---|---|---|---|---|
| 24 | phenyl | phenyl | CH3 | 492.6 | 493.19 |
| 25 | phenyl |  | CH3 | H | 416.5 | 416.83 |
| 26 | thiophen-2-yl | CH3 | CH3 | 436.6 | 437.14 |

TABLE 3-continued
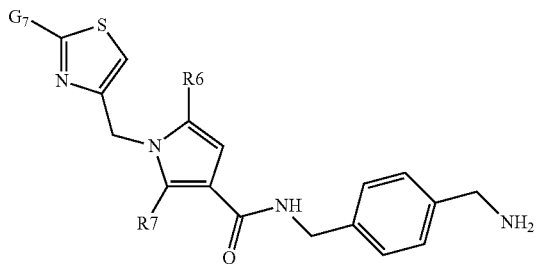
| Example No | G7 | R6 | R7 | Free Base MW | [M + H]+ |
|---|---|---|---|---|---|
| 27 | 3-Cl-phenyl | CH3 | CH3 | 465.0 | 465.13 |
| 28 | 4-Cl-phenyl | CH3 | CH3 | 465.0 | 465.14 |
| 29 | 3-F-phenyl | CH3 | CH3 | 448.6 | 449.16 |
| 30 | 3-CH3-phenyl | CH3 | CH3 | 444.6 | 445.32 |
| 31 | pyridin-3-yl | CH3 | CH3 | 431.6 | 454.18 (M + Na) |
| 32 | pyridin-4-yl | CH3 | CH3 | 431.6 | 432.38 |
| 33 | 3-OCH3-phenyl | CH3 | CH3 | 460.6 | 461.36 |

TABLE 3-continued
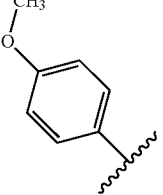
| Example No | G7 | R6 | R7 | Free Base MW | [M + H]+ |
|---|---|---|---|---|---|
| 34 | 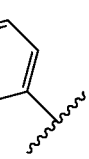 | CH3 | CH3 | 460.6 | 461.37 |
| 35 | 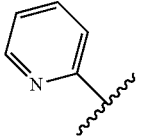 [SMILES: *c1ccccn1] | CH3 | CH3 | 444.6 | 445.37 |
| 36 | 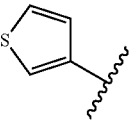 | CH3 | CH3 | 431.6 | 432.39 |
| 37 | 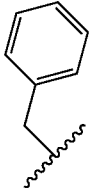 [SMILES: *Cc1ccccc1] | CH3 | CH3 | 436.6 | 437.32 |
| 38 | 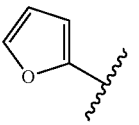 [SMILES: *c1ccco1] | CH3 | CH3 | 444.6 | 445.36 |
| 39 | 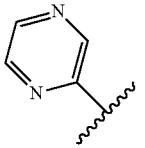 [SMILES: *c1cnccn1] | CH3 | CH3 | 420.5 | 421.19 |
| 40 |  | CH3 | CH3 | 432.5 | 433.21 |

TABLE 3-continued
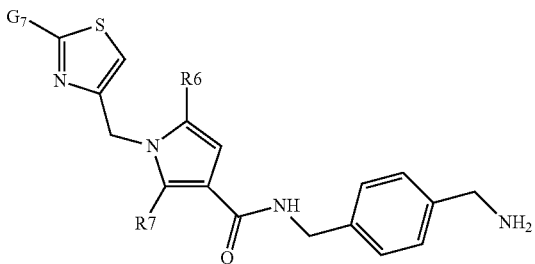
| Example No | G7 | R6 | R7 | Free Base MW | [M + H]+ |
|---|---|---|---|---|---|
| 41 | H3C-CH2-O-C6H4- | CH3 | CH3 | 474.6 | 475.26 |
TABLE 4
| Example No | B | R8 | R9 | G8 | Free Base MW | [M + H]+ |
|---|---|---|---|---|---|---|
| 42 | 4-(aminomethyl)phenyl | (R)-CH3 | H | H | 444.6 | 445.15 |
| 43 | 6-(aminomethyl)pyridin-3-yl | H | H | H | 431.6 | 432.22 |
| 44 | 6-(aminomethyl)pyridin-3-yl | H | H | F | 449.5 | 450.18 |

TABLE 4-continued

| Example No | B | R8 | R9 | G8 | Free Base MW | [M + H]⁺ |
|---|---|---|---|---|---|---|
| 45 | 2-fluoro-4-(aminomethyl)phenyl | H | H | H | 448.6 | 449.14 |
| 46 | 2-methyl-4-(aminomethyl)phenyl | H | H | H | 444.6 | 445.18 |
| 47 | 3-fluoro-4-(aminomethyl)phenyl | H | H | H | 448.6 | 449.07 |
| 48 | 4-(1-aminoethyl)phenyl | H | H | H | 444.593 | 467.15 (M + Na) |
| 49 | 3-chloro-4-(aminomethyl)phenyl | H | H | H | 465.01 | 465.00 |
| 50 | 2-trifluoromethyl-4-(aminomethyl)phenyl | H | H | H | 498.564 | 499.04 |

TABLE 4-continued
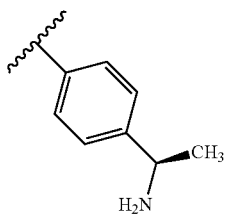 [SMILES: *c1ccc([C@@H](C)N)cc1]
| Example No | B | R8 | R9 | G8 | Free Base MW | [M + H]⁺ |
|---|---|---|---|---|---|---|
| 51 | 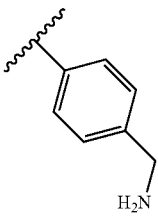 [SMILES: *c1ccc(CN)cc1] | H | H | H | 444.593 | 467.03 (M + Na) |
| 52 | 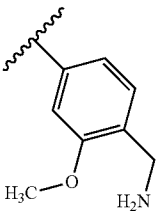 [SMILES: *c1ccc(CN)c(OC)c1] | —CH₂—CH₂— (so as to form spiro-cyclo-propyl) | | H | 456.604 | |
| 53 | 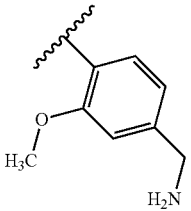 [SMILES: *c1ccc(CN)cc1OC] | H | H | H | 460.592 | 483.21 (M + Na) |
| 54 | 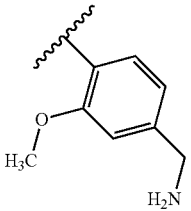 [SMILES: *c1ccc(CN)cc1OC] | H | H | H | 460.592 | 483.29 (M + Na) |
TABLE 5
| Example No | G9 | G10 | R3 | R7 | Free Base MW | [M + H]⁺ |
|---|---|---|---|---|---|---|
| 55 | H | H | H | H | 347.5 | 348.24 |
| 56 | H | H | Cl | H | 381.9 | 382.15 |

TABLE 5-continued
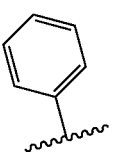 [SMILES: *c1ccccc1]
| Example No | G9 | G10 | R3 | R7 | Free Base MW | [M + H]+ |
|---|---|---|---|---|---|---|
| 57 | H | H | H | 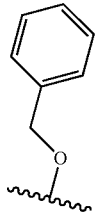 [SMILES: *OCc1ccccc1] | 409.5 | 410.24 |
| 58 | CH$_3$CH$_2$O | H | H | CH$_3$ | 391.5 | 392.21 |
| 59 | H | CH$_3$CH$_2$O | H | CH$_3$ | 391.5 | 392.21 |
| 60 | H | 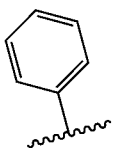 [SMILES: *c1ccccc1] | H | CH$_3$ | 453.6 | 454.2 |
| 61 | H | CH$_3$O | H | CH$_3$ | 377.5 | 378.71 |
| 62 | H$_2$NCO | H | H | CH$_3$ | 390.5 | 391.15 |
| 63 | H | H$_2$NCO | H | CH$_3$ | 390.5 | 391.13 |
| 64 | NC | H | H | CH$_3$ | 372.5 | 373.14 |
| 65 | H | NC | H | CH$_3$ | 372.5 | 373.13 |
| 66 | H$_2$NCH$_2$ | H | H | CH$_3$ | 376.5 | 377.18 |
| 67 | H | H$_2$NCH$_2$ | H | CH$_3$ | 376.5 | 377.19 |
| 68 | H | H$_3$CCONHCH$_2$ | H | CH$_3$ | 418.5 | 419.16 |
| 69 | 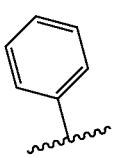 [SMILES: *c1ccccc1] | H | H | CH$_3$ | 423.5 | 424.28 |
| 70 | H | 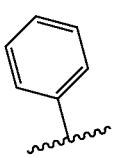 [SMILES: *c1ccccc1] | H | CH$_3$ | 423.5 | 424.33 |

TABLE 5-continued
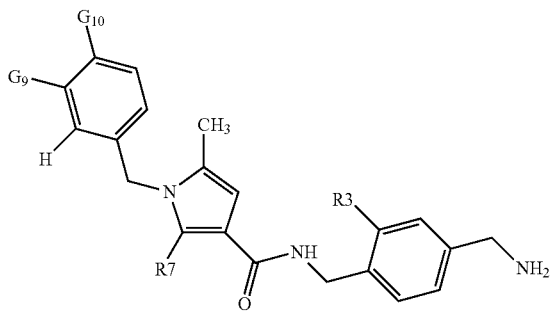
| Example No | G9 | G10 | R3 | R7 | Free Base MW | [M + H]+ |
|---|---|---|---|---|---|---|
| 71 | (3-pyridyl) | H | H | CH₃ | 424.5 | 425.41 |
| 72 | (4-pyridyl) | H | H | CH₃ | 424.5 | 425.36 |
| 73 | (morpholinyl) | H | H | CH₃ | 432.6 | 433.24 |
| 74 | (piperidinyl) | H | H | CH₃ | 430.6 | 431.28 |
TABLE 6
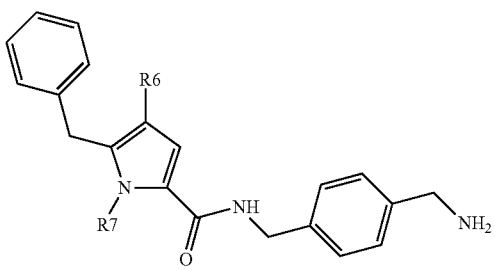
| Example No | R7 | R6 | Free Base MW | [M + H]+ |
|---|---|---|---|---|
| 75 | CH₃ | CH₃ | 347.5 | 348.2 |
| 76 | H | CH₃ | 333.4 | 334.17 |
TABLE 6-continued
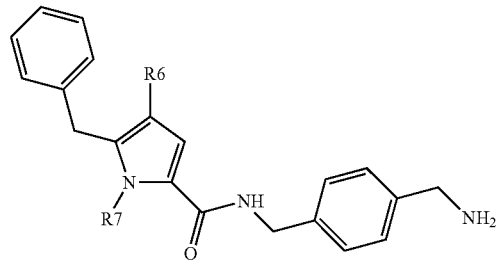
| Example No | R7 | R6 | Free Base MW | [M + H]+ |
|---|---|---|---|---|
| 77 | CH₃CH₂CH₂ | CH₃ | 361.5 | 362.19 |
| 78 | CH₃CH₂ | CH₃ | 375.5 | 376.21 |

TABLE 7
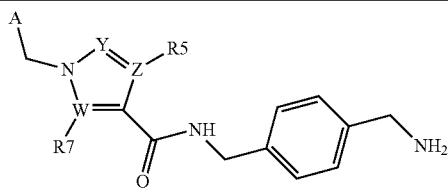
| Example No | A | R7 | R5 | W | Z | Y | Free Base MW | [M + H]+ |
|---|---|---|---|---|---|---|---|---|
| 79 | 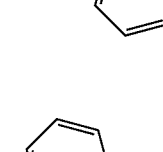 | H | H | C | C | N | 405.5 | |
| 80 | 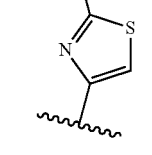 | CH3 | H | C | C | N | 417.5 | 418.16 |
| 81 | 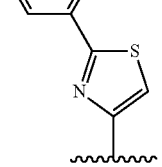 | H | CH3 | C | C | N | 417.5 | 418.14 |
| 82 | 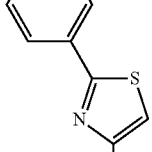 | CF3 | H | C | C | N | 471.5 | 494.06 (M + Na) |
| 83 | 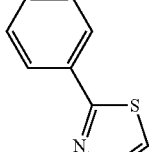 | H | CF3 | C | C | N | 471.5 | 494.04 (M + Na) |
| 84 | 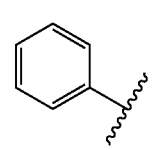 [SMILES: *c1ccccc1] | H | 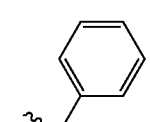 | C | C | N | 396.5 | 397.21 |

TABLE 7-continued

| Example No | A | R7 | R5 | W | Z | Y | Free Base MW | [M + H]+ |
|---|---|---|---|---|---|---|---|---|
| 85 | 4-methylpyrazol-1-ylmethyl-phenyl | H | H | C | C | N | 414.5 | 437.32 (M + Na) |
| 86 | 3,5-dimethylpyrazol-1-ylmethyl-phenyl | H | H | C | C | N | 428.5 | 429.31 |
| 87 | 4-(piperidine-1-carbonyl)phenyl | H | H | C | C | N | 431.53 | 432.24 |
| 88 | 4-phenoxyphenyl | absent | absent | N | N | CH | 413.48 | 455.06 (M + MeCN) |

TABLE 8
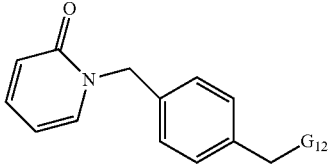
| Example No | G12 | Free Base MW | [M + H]+ |
|---|---|---|---|
| 89 | 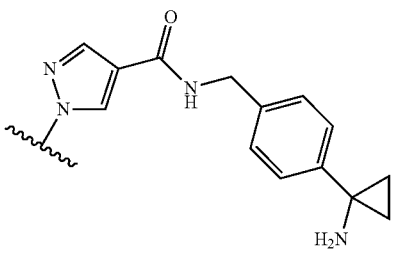 [SMILES: *n1cc(C(=O)NCc2ccc(C3(N)CC3)cc2)cn1] | 453.5 | 454.3 |
| 90 | 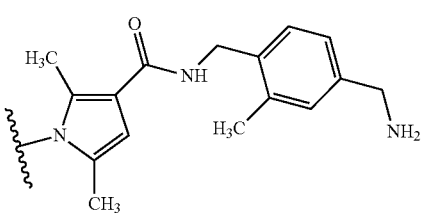 [SMILES: *n1c(C)cc(C(=O)NCc2ccc(CN)cc2C)c1C] | 454.6 | 455.3 |
| 91 | 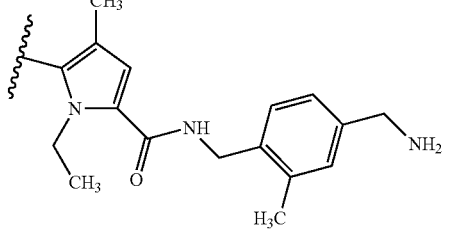 | 468.6 | 469.3 |
| 92 | 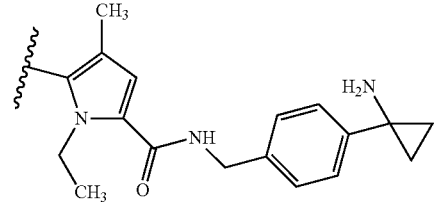 [SMILES: *c1c(C)cc(C(=O)NCc2ccc(C3(N)CC3)cc2)n1CC] | 482.6 | 483.2 |
| 93 | 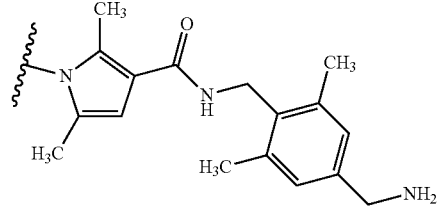 [SMILES: *n1c(C)cc(C(=O)NCc2c(C)cc(CN)cc2C)c1C] | 494.6 | 495.2 |
| 94 | | 482.6 | 483.3 |

TABLE 8-continued
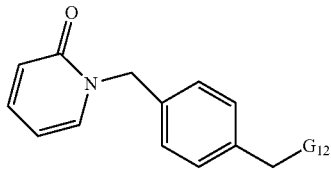
| Example No | G12 | Free Base MW | [M + H]+ |
|---|---|---|---|
| 95 | 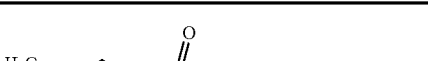 | 496.6 | 497.4 |
TABLE 9
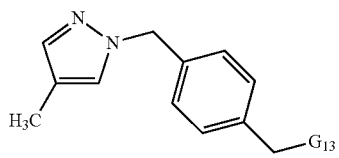
| Example No | G13 | Free Base MW | [M + H]+ |
|---|---|---|---|
| 96 | ![structure] | 441.6 | 442.3 |
| 97 | ![structure] | 455.6 | 456.3 |
| 98 | ![structure] | 467.6 | 468.3 |

TABLE 9-continued

| Example No | G13 | Free Base MW | [M + H]⁺ |
|---|---|---|---|
| 99 | | 469.6 | 470.2 |
| 100 | | 481.6 | 482.3 |
| 101 | | 469.6 | 470.3 |
| 102 | | 483.7 | 484.3 |
| 103 | | 440.54 | 441.2 |

TABLE 9-continued
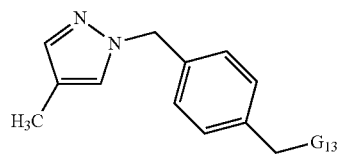
| Example No | G13 | Free Base MW | [M + H]+ |
|---|---|---|---|
| 104 | 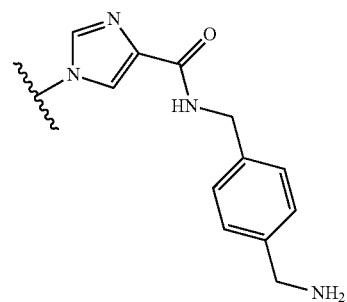 [SMILES: *n1cnc(C(=O)NCc2ccc(CN)cc2)c1] | 414.50 | 415.3 |
| 105 | 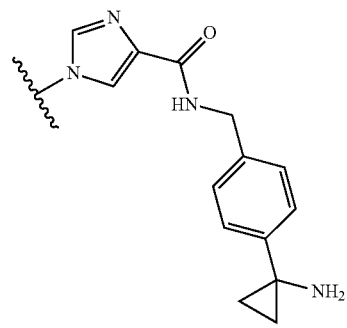 [SMILES: *n1cnc(C(=O)NCc2ccc(C3(N)CC3)cc2)c1] | 440.54 | 441.3 |
| 106 | 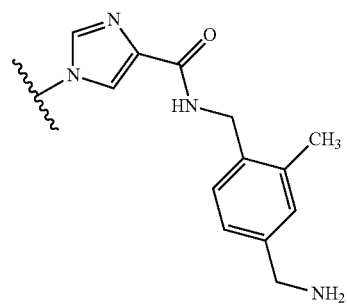 [SMILES: *n1cnc(C(=O)NCc2ccc(CN)cc2C)c1] | 428.53 | 429.3 |
| 107 | 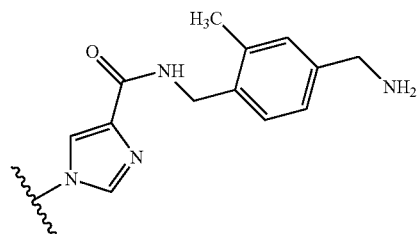 [SMILES: *n1cnc(C(=O)NCc2ccc(CN)cc2C)c1] | 428.53 | 429.3 |

TABLE 9-continued
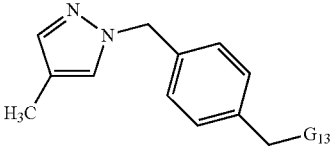
| Example No | G13 | Free Base MW | [M + H]+ |
|---|---|---|---|
| 108 | 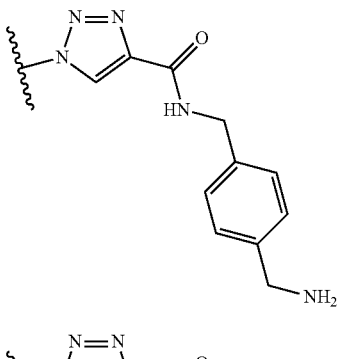 | 415.49 | 416.3 |
| 109 | 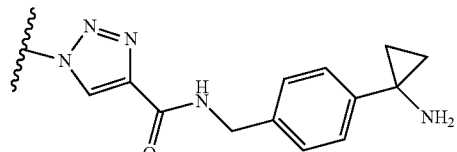 | 429.52 | 430.3 |
| 110 | 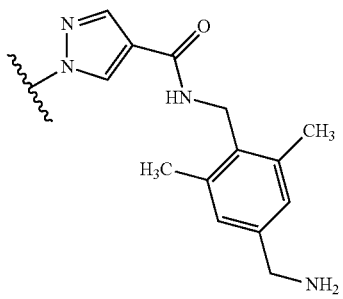 [SMILES: *n1cc(C(=O)NCc2c(C)cc(CN)cc2C)cn1] | 441.53 | 442.2 |
| 111 | 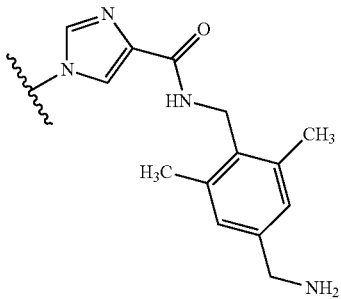 [SMILES: *n1cnc(C(=O)NCc2c(C)cc(CN)cc2C)c1] | 442.56 | 443.3 |
| 112 | | 442.56 | 443.3 |

TABLE 9-continued

[Structure: 4-methyl-pyrazole-N-CH2-phenyl-CH2-G13]

| Example No | G13 | Free Base MW | [M + H]+ |
|---|---|---|---|
| 113 | [triazole-C(=O)-NH-CH2-(2,6-dimethyl-4-aminomethyl)phenyl] | 443.54 | 444.3 |
| 114 | [3-methyl-pyrazole-C(=O)-NH-CH2-(2,6-dimethyl-4-aminomethyl)phenyl] | 456.58 | 457.05 |
| 115 | [5-methyl-pyrazole-C(=O)-NH-CH2-(2,6-dimethyl-4-aminomethyl)phenyl] | 456.58 | 457.05 |
| 116 | [3,5-dimethyl-pyrazole-C(=O)-NH-CH2-(2,6-dimethyl-4-aminomethyl)phenyl] | 470.61 | 471.07 |

TABLE 9-continued

| Example No | G13 | Free Base MW | [M + H]+ |
|---|---|---|---|
| 117 | (structure) | 500.49 | 500.96 |
| 118 | (structure) | 510.55 | 511.00 |
| 119 | (structure) | 514.52 | 514.98 |
| 120 | (structure) | 528.54 | 528.90 |

TABLE 10
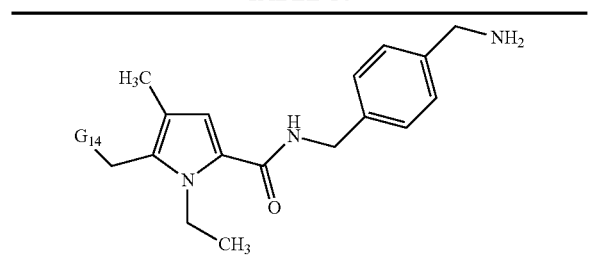
| Example No | G14 | Free Base MW | [M + H]+ |
|---|---|---|---|
| 121 | (4-methylpyrazol-1-ylmethyl)phenyl | 455.6 | 456.2 |
| 122 | (2-oxopyridin-1-ylmethyl)phenyl | 468.6 | 469.2 |
TABLE 10-continued
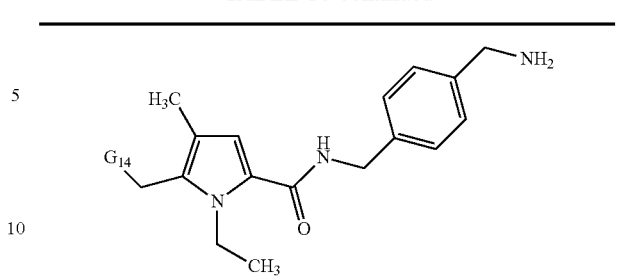
| Example No | G14 | Free Base MW | [M + H]+ |
|---|---|---|---|
| 123 | 2-phenylthiazol-4-yl | 444.6 | 445 |
TABLE 11
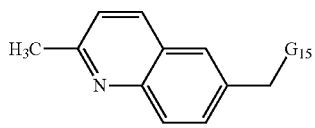
| Example No | G15 | Free Base MW | [M + H]+ |
|---|---|---|---|
| 124 | (3-methylpyrazol-1-yl) amide with 2,6-dimethyl-4-(aminomethyl)benzyl | 427.55 | 428.00 |
| 125 | (5-methylpyrazol-1-yl) amide with 2,6-dimethyl-4-(aminomethyl)benzyl | 427.55 | 428.01 |

TABLE 11-continued

[Structure: H3C-quinoline-CH2-G15 with 2-methyl group]

| Example No | G15 | Free Base MW | [M + H]+ |
|---|---|---|---|
| 126 | [pyrazole with CF3 at 3-position, amide to 2,6-dimethyl-4-(aminomethyl)phenyl] | 481.53 | 481.88 |
| 127 | [pyrazole with CF3 at 5-position, amide to 2,6-dimethyl-4-(aminomethyl)phenyl] | 481.53 | 481.89 |
| 128 | [2,5-dimethylpyrrole-3-carboxamide to 2,6-dimethyl-4-(aminomethyl)phenyl] | 440.58 | 441.07 |

TABLE 12

[Structure: pyrazole-4-carboxamide with R5 at 3-position, R7 at 5-position, G16-CH2 on N1, amide to 2,6-dimethyl-4-(aminomethyl)phenyl]

| Example No | G16 | R5 | R7 | Free Base MW | [M + H]+ |
|---|---|---|---|---|---|
| 129 | 2-(pyrrolidin-1-yl)pyridin-4-yl | CF3 | H | 486.54 | 487.03 |
| 130 | 6-(pyrrolidin-1-yl)pyridin-3-yl | CF3 | H | 486.54 | |
| 131 | 2-(pyrrolidin-1-yl)pyridin-4-yl | H | CH3 | 432.57 | 432.99 |
| 132 | 6-(pyrrolidin-1-yl)pyridin-3-yl | CH3 | H | 432.57 | |

TABLE 12-continued

| Example No | G16 | R5 | R7 | Free Base MW | [M + H]+ |
|---|---|---|---|---|---|
| 133 | (pyridin-4-yl with 2-pyrrolidinyl) | CH₃ | H | 432.57 | 432.99 |

TABLE 13

| Example No | Name |
|---|---|
| 8 | 2,5-Dimethyl-1-(5-pyridin-3-yl-thiophen-3-ylmethyl)-1H-pyrrole-3-carboxylic acid 4-aminomethyl-benzylamide |
| 9 | 2,5-Dimethyl-1-(4-phenyl-thiophen-2-ylmethyl)-1H-pyrrole-3-carboxylic acid 4-aminomethyl-benzylamide |
| 10 | 2,5-Dimethyl-1-(5-phenyl-thiophen-3-ylmethyl)-1H-pyrrole-3-carboxylic acid 4-aminomethyl-benzylamide |
| 11 | 2,5-Dimethyl-1-(3-phenyl-isoxazol-5-ylmethyl)-1H-pyrrole-3-carboxylic acid 4-aminomethyl-benzylamide |
| 12 | 1-Benzothiazol-2-ylmethyl-2,5-dimethyl-1H-pyrrole-3-carboxylic acid 4-aminomethyl-benzylamide |
| 13 | 2,5-Dimethyl-1-(4-pyridin-3-yl-thiophen-2-ylmethyl)-1H-pyrrole-3-carboxylic acid 4-aminomethyl-benzylamide |
| 14 | 2,5-Dimethyl-1-(4-pyridin-4-yl-thiophen-2-ylmethyl)-1H-pyrrole-3-carboxylic acid 4-aminomethyl-benzylamide |
| 15 | 2,5-Dimethyl-1-(6-morpholin-4-yl-pyridin-2-ylmethyl)-1H-pyrrole-3-carboxylic acid 4-aminomethyl-benzylamide |
| 16 | 2,5-Dimethyl-1-(6-phenyl-pyridin-2-ylmethyl)-1H-pyrrole-3-carboxylic acid 4-aminomethyl-benzylamide |
| 17 | 1-[2,3']Bipyridinyl-6-ylmethyl-2,5-dimethyl-1H-pyrrole-3-carboxylic acid 4-aminomethyl-benzylamide |
| 18 | 2,5-Methyl-1-(2-phenyl-oxazol-4-ylmethyl)-1H-pyrrole-3-carboxylic acid 4-aminomethyl-benzylamide |
| 19 | 2,5-Dimethyl-1-(5-methyl-2-phenyl-oxazol-4-ylmethyl)-1H-pyrrole-3-carboxylic acid 4-aminomethyl-benzylamide |
| 20 | 2,5-Dimethyl-1-thiophen-2-ylmethyl-1H-pyrrole-3-carboxylic acid 4-amidomethyl-benzylamide |
| 21 | 2,5-Dimethyl-1-(5-pyridin-4-yl-thiophen-2-ylmethyl)-1H-pyrrole-3-carboxylic acid 4-aminomethyl-benzylamide |
| 22 | 2,5-Dimethyl-1-(5-phenyl-thiophen-2-ylmethyl)-1H-pyrrole-3-carboxylic acid 4-aminomethyl-benzylamide |
| 23 | 2,5-Dimethyl-1-[5-(2-methyl-thiazol-4-yl)-thiophen-2-ylmethyl]-1H-pyrrole-3-carboxylic acid 4-aminomethyl-benzylamide |
| 24 | 5-Methyl-2-phenyl-1-(2-phenyl-thiazol-4-ylmethyl)-1H-pyrrole-3-carboxylic acid 4-aminomethyl-benzylamide |
| 25 | 2-Methyl-1-(2-phenyl-thiazol-4-ylmethyl)-1H-pyrrole-3-carboxylic acid 4-aminomethyl-benzylamide |
| 26 | 2,5-Dimethyl-1-[2-(2-thienyl)-thiazol-4-ylmethyl]-1H-pyrrole-3-carboxylic acid 4-aminomethyl-benzylamide |
| 27 | 2,5-Dimethyl-1-[2-(3-chlorophenyl)-thiazol-4-ylmethyl]-1H-pyrrole-3-carboxylic acid 4-aminomethyl-benzylamide |
| 28 | 2,5-Dimethyl-1-[2-(4-chlorophenyl)-thiazol-4-ylmethyl]-1H-pyrrole-3-carboxylic acid 4-aminomethyl-benzylamide |
| 29 | 1-[2-(3-Fluoro-phenyl)-thiazol-4-ylmethyl]-2,5-dimethyl-1H-pyrrole-3-carboxylic acid 4-aminomethyl-benzylamide |
| 30 | 2,5-Dimethyl-1-(2-m-tolyl-thiazol-4-ylmethyl)-1H-pyrrole-3-carboxylic acid 4-aminomethyl-benzylamide |

TABLE 13-continued

| Example No | Name |
|---|---|
| 31 | 2,5-Dimethyl-1-(2-pyridin-3-yl-thiazol-4-ylmethyl)-1H-pyrrole-3-carboxylic acid 4-aminomethyl-benzylamide |
| 32 | 2,5-Dimethyl-1-(2-pyridin-4-yl-thiazol-4-ylmethyl)-1H-pyrrole-3-carboxylic acid 4-aminomethyl-benzylamide |
| 33 | 2,5-Dimethyl-1-(3-methoxyphenyl-thiazol-4-ylmethyl)-1H-pyrrole-3-carboxylic acid 4-aminomethyl-benzylamide |
| 34 | 2,5-Dimethyl-1-(4-methoxyphenyl-thiazol-4-ylmethyl)-1H-pyrrole-3-carboxylic acid 4-aminomethyl-benzylamide |
| 35 | 2,5-Dimethyl-1-(2-p-tolyl-thiazol-4-ylmethyl)-1H-pyrrole-3-carboxylic acid 4-aminomethyl-benzylamide |
| 36 | 2,5-Dimethyl-1-(2-pyridin-2-yl-thiazol-4-ylmethyl)-1H-pyrrole-3-carboxylic acid 4-aminomethyl-benzylamide |
| 37 | 2,5-Dimethyl-1-(2-thiophen-3-yl-thiazol-4-ylmethyl)-1H-pyrrole-3-carboxylic acid 4-aminomethyl-benzylamide |
| 38 | 1-(2-Benzyl-thiazol-4-ylmethyl)-2,5-dimethyl-1H-pyrrole-3-carboxylic acid 4-aminomethyl-benzylamide |
| 39 | 2,5-Dimethyl-1-(2-furan-3-yl-thiazol-4-ylmethyl)-1H-pyrrole-3-carboxylic acid 4-aminomethyl-benzylamide |
| 40 | 2,5-Dimethyl-1-(2-pyrazin-2-yl-thiazol-4-ylmethyl)-1H-pyrrole-3-carboxylic acid 4-aminomethyl-benzylamide |
| 41 | 1-[2-(4-Ethoxy-phenyl)-thiazol-4-ylmethyl]-2,5-dimethyl-1H-pyrrole-3-carboxylic acid 4-aminomethyl-benzylamide |
| 42 | 2,5-Dimethyl-1-(2-phenyl-thiazol-4-ylmethyl)-1H-pyrrole-3-carboxylic acid [(R)-1-(4-aminomethyl-phenyl)-ethyl]-amide |
| 43 | 2,5-Dimethyl-1-(2-phenyl-thiazol-4-ylmethyl)-1H-pyrrole-3-carboxylic acid (6-aminomethyl-pyridin-3-ylmethyl)-amide |
| 44 | 1-[2-(3-Fluoro-phenyl)-thiazol-4-ylmethyl]-2,5-dimethyl-1H-pyrrole-3-carboxylic acid (6-aminomethyl-pyridin-3-ylmethyl)-amide |
| 45 | 2,5-Dimethyl-1-(2-phenyl-thiazol-4-ylmethyl)-1H-pyrrole-3-carboxylic acid 4-aminomethyl-3-fluoro-benzylamide |
| 46 | 2,5-Dimethyl-1-(2-phenyl-thiazol-4-ylmethyl)-1H-pyrrole-3-carboxylic acid 4-aminomethyl-3-methyl-benzylamide |
| 47 | 2,5-Dimethyl-1-(2-phenyl-thiazol-4-ylmethyl)-1H-pyrrole-3-carboxylic acid 4-aminomethyl-2-fluoro-benzylamide |
| 48 | 2,5-Dimethyl-1-(2-phenyl-thiazol-4-ylmethyl)-1H-pyrrole-3-carboxylic acid 4-((R)-1-amino-ethyl)-benzylamide |
| 49 | 2,5-Dimethyl-1-(2-phenyl-thiazol-4-ylmethyl)-1H-pyrrole-3-carboxylic acid 4-aminomethyl-2-chloro-benzylamide |
| 50 | 2,5-Dimethyl-1-(2-phenyl-thiazol-4-ylmethyl)-1H-pyrrole-3-carboxylic acid 4-aminomethyl-2-trifluoromethyl-benzylamide |
| 51 | 2,5-Dimethyl-1-(2-phenyl-thiazol-4-ylmethyl)-1H-pyrrole-3-carboxylic acid-4-((S)-1-amino-ethyl)-benzylamide |
| 52 | 2,5-Dimethyl-1-(2-phenyl-thiazol-4-ylmethyl)-1H-pyrrole-3-carboxylic acid [1-(4-aminomethyl-phenyl)-cyclopropyl]-amide |
| 53 | 2,5-Dimethyl-1-(2-phenyl-thiazol-4-ylmethyl)-1H-pyrrole-3-carboxylic acid 4-aminomethyl-3-methoxy-benzylamide |
| 54 | 2,5-Dimethyl-1-(2-phenyl-thiazol-4-ylmethyl)-1H-pyrrole-3-carboxylic acid 4-aminomethyl-2-methoxy-benzylamide |
| 55 | 1-Benzyl-2,5-dimethyl-1H-pyrrole-3-carboxylic acid 4-aminomethyl-benzylamide |
| 56 | 1-Benzyl-2,5-dimethyl-1H-pyrrole-3-carboxylic acid 4-aminomethyl-2-chloro-benzylamide |
| 57 | 1-Benzyl-5-methyl-2-phenyl-1H-pyrrole-3-carboxylic acid 4-aminomethyl-benzylamide |
| 58 | 1-(3-Ethoxy-benzyl)-2,5-dimethyl-1H-pyrrole-3-carboxylic acid 4-aminomethyl-benzylamide |
| 59 | 1-(4-Ethoxy-benzyl)-2,5-dimethyl-1H-pyrrole-3-carboxylic acid 4-aminomethyl-benzylamide |
| 60 | 1-(4-Benzyloxy-benzyl)-2,5-dimethyl-1H-pyrrole-3-carboxylic acid 4-aminomethyl-benzylamide |
| 61 | 1-(4-Methoxy-benzyl)-2,5-dimethyl-1H-pyrrole-3-carboxylic acid 4-aminomethyl-benzylamide |
| 62 | 1-(3-Carbamoyl-benzyl)-2,5-dimethyl-1H-pyrrole-3-carboxylic acid 4-aminomethyl-benzylamide |
| 63 | 1-(4-Carbamoyl-benzyl)-2,5-dimethyl-1H-pyrrole-3-carboxylic acid 4-aminomethyl-benzylamide |
| 64 | 1-(3-Cyano-benzyl)-2,5-dimethyl-1H-pyrrole-3-carboxylic acid 4-aminomethyl-benzylamide |
| 65 | 1-(4-Cyano-benzyl)-2,5-dimethyl-1H-pyrrole-3-carboxylic acid 4-aminomethyl-benzylamide |
| 66 | 1-(3-Aminomethyl-benzyl)-2,5-dimethyl-1H-pyrrole-3-carboxylic acid 4-aminomethyl-benzylamide |
| 67 | 1-(4-Aminomethyl-benzyl)-2,5-dimethyl-1H-pyrrole-3-carboxylic acid 4-aminomethyl-benzylamide |
| 68 | 1-[4-(Acetylamino-methyl)-benzyl]-2,5-dimethyl-1H-pyrrole-3-carboxylic acid 4-aminomethyl-benzylamide |

TABLE 13-continued

| Example No | Name |
|---|---|
| 69 | 1-Biphenyl-3-ylmethyl-2,5-dimethyl-1H-pyrrole-3-carboxylic acid 4-aminomethyl-benzylamide |
| 70 | 1-Biphenyl-4-ylmethyl-2,5-dimethyl-1H-pyrrole-3-carboxylic acid 4-aminomethyl-benzylamide |
| 71 | 2,5-Dimethyl-1-(3-pyridin-3-yl-benzyl)-1H-pyrrole-3-carboxylic acid 4-aminomethyl-benzylamide |
| 72 | 2,5-Dimethyl-1-(3-pyridin-4-yl-benzyl)-1H-pyrrole-3-carboxylic acid 4-aminomethyl-benzylamide |
| 73 | 2,5-Dimethyl-1-(3-morpholin-4-yl-benzyl)-1H-pyrrole-3-carboxylic acid 4-aminomethyl-benzylamide |
| 74 | 2,5-Dimethyl-1-(3-piperidin-1-yl-benzyl)-1H-pyrrole-3-carboxylic acid 4-aminomethyl-benzylamide |
| 75 | 5-Benzyl-1,4-dimethyl-1H-pyrrole-2-carboxylic acid 4-aminomethyl-benzylamide |
| 76 | 5-Benzyl-4-methyl-1H-pyrrole-2-carboxylic acid 4-aminomethyl-benzylamide |
| 77 | 5-Benzyl-1-ethyl-4-methyl-1H-pyrrole-2-carboxylic acid 4-aminomethyl-benzylamide |
| 78 | 5-Benzyl-4-methyl-1-propyl-1H-pyrrole-2-carboxylic acid 4-aminomethyl-benzylamide |
| 79 | 1-(4-Isopropylcarbamoyl-benzyl)-1H-pyrazole-4-carboxylic acid 4-aminomethyl-benzylamide |
| 80 | 5-Methyl-1-(2-phenyl-thiazol-4-ylmethyl)-1H-pyrazole-4-carboxylic acid 4-aminomethyl-benzylamide |
| 81 | 3-Methyl-1-(2-phenyl-thiazol-4-ylmethyl)-1H-pyrazole-4-carboxylic acid 4-aminomethyl-benzylamide |
| 82 | 1-(2-Phenyl-thiazol-4-ylmethyl)-5-trifluoromethyl-1H-pyrazole-4-carboxylic acid 4-aminomethyl-benzylamide |
| 83 | 1-(2-Phenyl-thiazol-4-ylmethyl)-3-trifluoromethyl-1H-pyrazole-4-carboxylic acid 4-aminomethyl-benzylamide |
| 84 | 1-Benzyl-3-phenyl-1H-pyrazole-4-carboxylic acid 4-aminomethyl-benzylamide |
| 85 | 1-[4-(4-Methyl-pyrazol-1-ylmethyl)-benzyl]-1H-pyrazole-4-carboxylic acid 4-aminomethyl-benzylamide |
| 86 | 1-[4-(3,5-Dimethyl-pyrazol-1-ylmethyl)-benzyl]-1H-pyrazole-4-carboxylic acid 4-aminomethyl-benzylamide |
| 87 | 1-[4-(Piperidine-1-carbonyl)-benzyl]-1H-pyrazole-4-carboxylic acid 4-aminomethyl-benzylamide |
| 88 | 1-(4-Phenoxy-benzyl)-1H-[1,2,4]triazole-3-carboxylic acid 4-aminomethyl-benzylamide |
| 89 | 1-[4-(2-Oxo-2H-pyridin-1-ylmethyl)-benzyl]-1H-pyrazole-4-carboxylic acid 4-(1-amino-cyclopropyl)-benzylamide |
| 90 | 2,5-Dimethyl-1-[4-(2-oxo-2H-pyridin-1-ylmethyl)-benzyl]-1H-pyrrole-3-carboxylic acid 4-aminomethyl-benzylamide |
| 91 | 2,5-Dimethyl-1-[4-(2-oxo-2H-pyridin-1-ylmethyl)-benzyl]-1H-pyrrole-3-carboxylic acid 4-aminomethyl-2-methyl-benzylamide |
| 92 | 1-Ethyl-4-methyl-5-[4-(2-oxo-2H-pyridin-1-ylmethyl)-benzyl]-1H-pyrrole-2-carboxylic acid 4-aminomethyl-2-methyl-benzylamide |
| 93 | 1-Ethyl-4-methyl-5-[4-(2-oxo-2H-pyridin-1-ylmethyl)-benzyl]-1H-pyrrole-2-carboxylic acid 4-(1-amino-cyclopropyl)-benzylamide |
| 94 | 2,5-Dimethyl-1-[4-(2-oxo-2H-pyridin-1-ylmethyl)-benzyl]-1H-pyrrole-3-carboxylic acid 4-aminomethyl-2,6-dimethyl-benzylamide |
| 95 | 1-Ethyl-4-methyl-5-[4-(2-oxo-2H-pyridin-1-ylmethyl)-benzyl]-1H-pyrrole-2-carboxylic acid 4-aminomethyl-2,6-dimethyl-benzylamide |
| 96 | 2,5-Dimethyl-1-[4-(4-methyl-pyrazol-1-ylmethyl)-benzyl]-1H-pyrrole-3-carboxylic acid 4-aminomethyl-benzylamide |
| 97 | 2,5-Dimethyl-1-[4-(4-methyl-pyrazol-1-ylmethyl)-benzyl]-1H-pyrrole-3-carboxylic acid 4-aminomethyl-2-methyl-benzylamide |
| 98 | 2,5-Dimethyl-1-[4-(4-methyl-pyrazol-1-ylmethyl)-benzyl]-1H-pyrrole-3-carboxylic acid 4-(1-amino-cyclopropyl)-benzylamide |
| 99 | 1-Ethyl-4-methyl-5-[4-(4-methyl-pyrazol-1-ylmethyl)-benzyl]-1H-pyrrole-2-carboxylic acid 4-aminomethyl-2-methyl-benzylamide |
| 100 | 1-Ethyl-4-methyl-5-[4-(4-methyl-pyrazol-1-ylmethyl)-benzyl]-1H-pyrrole-2-carboxylic acid 4-(1-amino-cyclopropyl)-benzylamide |
| 101 | 2,5-Dimethyl-1-[4-(4-methyl-pyrazol-1-ylmethyl)-benzyl]-1H-pyrrole-3-carboxylic acid 4-aminomethyl-2,6-dimethyl-benzylamide |
| 102 | 1-Ethyl-4-methyl-5-[4-(4-methyl-pyrazol-1-ylmethyl)-benzyl]-1H-pyrrole-2-carboxylic acid 4-aminomethyl-2,6-dimethyl-benzylamide |
| 103 | 1-[4-(4-Methyl-pyrazol-1-ylmethyl)-benzyl]-1H-pyrazole-4-carboxylic acid 4-(1-amino-cyclopropyl)-benzylamide |
| 104 | 1-[4-(4-Methyl-pyrazol-1-ylmethyl)-benzyl]-1H-imidazole-4-carboxylic acid 4-aminomethyl-benzylamide |

TABLE 13-continued

| Example No | Name |
|---|---|
| 105 | 1-[4-(4-Methyl-pyrazol-1-ylmethyl)-benzyl]-1H-imidazole-4-carboxylic acid 4-(1-amino-cyclopropyl)-benzylamide |
| 106 | 1-[4-(4-Methyl-pyrazol-1-ylmethyl)-benzyl]-1H-pyrazole-4-carboxylic acid 4-aminomethyl-2-methyl-benzylamide |
| 107 | 1-[4-(4-Methyl-pyrazol-1-ylmethyl)-benzyl]-1H-imidazole-4-carboxylic acid 4-aminomethyl-2-methyl-benzylamide |
| 108 | 1-[4-(4-Methyl-pyrazol-1-ylmethyl)-benzyl]-1H-[1,2,3]triazole-4-carboxylic acid 4-aminomethyl-benzylamide |
| 109 | 1-[4-(4-Methyl-pyrazol-1-ylmethyl)-benzyl]-1H-[1,2,3]triazole-4-carboxylic acid 4-aminomethyl-2-methyl-benzylamide |
| 110 | 1-[4-(4-Methyl-pyrazol-1-ylmethyl)-benzyl]-1H-[1,2,3]triazole-4-carboxylic acid 4-(1-amino-cyclopropyl)-benzylamide |
| 111 | 1-[4-(4-Methyl-pyrazol-1-ylmethyl)-benzyl]-1H-pyrazole-4-carboxylic acid 4-aminomethyl-2,6-dimethyl-benzylamide |
| 112 | 1-[4-(4-Methyl-pyrazol-1-ylmethyl)-benzyl]-1H-imidazole-4-carboxylic acid 4-aminomethyl-2,6-dimethyl-benzylamide |
| 113 | 1-[4-(4-Methyl-pyrazol-1-ylmethyl)-benzyl]-1H-[1,2,3]triazole-4-carboxylic acid 4-aminomethyl-2,6-dimethyl-benzylamide |
| 114 | 3-Methyl-1-[4-(4-methyl-pyrazol-1-ylmethyl)-benzyl]-1H-pyrazole-4-carboxylic acid 4-aminomethyl-2,6-dimethyl-benzylamide |
| 115 | 5-Methyl-1-[4-(4-methyl-pyrazol-1-ylmethyl)-benzyl]-1H-pyrazole-4-carboxylic acid 4-aminomethyl-2,6-dimethyl-benzylamide |
| 116 | 3,5-Dimethyl-1-[4-(4-methyl-pyrazol-1-ylmethyl)-benzyl]-1H-pyrazole-4-carboxylic acid 4-aminomethyl-2,6-dimethyl-benzylamide |
| 117 | 1-[4-(4-Methyl-pyrazol-1-ylmethyl)-benzyl]-3-trifluoromethyl-1H-pyrazole-4-carboxylic acid 4-aminomethyl-3-fluoro-benzylamide |
| 118 | 1-[4-(4-Methyl-pyrazol-1-ylmethyl)-benzyl]-3-trifluoromethyl-1H-pyrazole-4-carboxylic acid 4-aminomethyl-2,6-dimethyl-benzylamide |
| 119 | 1-[4-(4-Methyl-pyrazol-1-ylmethyl)-benzyl]-3-trifluoromethyl-1H-pyrazole-4-carboxylic acid 4-aminomethyl-3-fluoro-2-methyl-benzylamide |
| 120 | 1-[4-(4-Methyl-pyrazol-1-ylmethyl)-benzyl]-3-trifluoromethyl-1H-pyrazole-4-carboxylic acid 4-aminomethyl-3-fluoro-2,6-dimethyl-benzylamide |
| 121 | 1-Ethyl-4-methyl-5-[4-(4-methyl-pyrazol-1-ylmethyl)-benzyl]-1H-pyrrole-2-carboxylic acid 4-aminomethyl-benzylamide |
| 122 | 1-Ethyl-4-methyl-5-[4-(2-oxo-2H-pyridin-1-ylmethyl)-benzyl]-1H-pyrrole-2-carboxylic acid 4-aminomethyl-benzylamide |
| 123 | 1-Ethyl-4-methyl-5-(2-phenyl-thiazol-4-ylmethyl)-1H-pyrrole-2-carboxylic acid 4-aminomethyl-benzylamide |
| 124 | 3-Methyl-1-(2-methyl-quinolin-6-ylmethyl)-1H-pyrazole-4-carboxylic acid 4-aminomethyl-2,6-dimethyl-benzylamide |
| 125 | 5-Methyl-1-(2-methyl-quinolin-6-ylmethyl)-1H-pyrazole-4-carboxylic acid 4-aminomethyl-2,6-dimethyl-benzylamide |
| 126 | 1-(2-Methyl-quinolin-6-ylmethyl)-3-trifluoromethyl-1H-pyrazole-4-carboxylic acid 4-aminomethyl-2,6-dimethyl-benzylamide |
| 127 | 1-(2-Methyl-quinolin-6-ylmethyl)-5-trifluoromethyl-1H-pyrazole-4-carboxylic acid 4-aminomethyl-2,6-dimethyl-benzylamide |
| 128 | 2,5-Dimethyl-1-(2-methyl-quinolin-6-ylmethyl)-1H-pyrrole-3-carboxylic acid 4-aminomethyl-2,6-dimethyl-benzylamide |
| 129 | 1-(2-Pyrrolidin-1-yl-pyridin-4-ylmethyl)-3-trifluoromethyl-1H-pyrazole-4-carboxylic acid 4-aminomethyl-2,6-dimethyl-benzylamide |
| 130 | 1-(6-Pyrrolidin-1-yl-pyridin-3-ylmethyl)-3-trifluoromethyl-1H-pyrazole-4-carboxylic acid 4-aminomethyl-2,6-dimethyl-benzylamide |
| 131 | 5-Methyl-1-(2-pyrrolidin-1-yl-pyridin-4-ylmethyl)-1H-pyrazole-4-carboxylic acid 4-aminomethyl-2,6-dimethyl-benzylamide |
| 132 | 3-Methyl-1-(6-pyrrolidin-1-yl-pyridin-3-ylmethyl)-1H-pyrazole-4-carboxylic acid 4-aminomethyl-2,6-dimethyl-benzylamide |
| 133 | 3-Methyl-1-(2-pyrrolidin-1-yl-pyridin-4-ylmethyl)-1H-pyrazole-4-carboxylic acid 4-aminomethyl-2,6-dimethyl-benzylamide |

TABLE 14

NMR data of examples

| Example No | Solvent | Chemical Shift (ppm) |
|---|---|---|
| 8 | d6-DMSO | 2.16 (3H, s), 2.46 (3H, s), 3.20-3.38 (2H, s, br), 3.66 (2H, s), 4.32 (2H, d, J = 6.0 Hz), 5.03 (2H, s), |

TABLE 14-continued

NMR data of examples

| Example No | Solvent | Chemical Shift (ppm) |
|---|---|---|
| | | 6.30 (1H, s), 7.00 (1H, d, J = 0.8 Hz), 7.15-7.25 (4H, m), 7.38 (1H, d, J = 1.3 Hz), 7.40-7.43 (1H, m), 7.98-8.01 (1H, m), 8.04 (1H, t, J = 6.1 Hz), 8.49 (1H, dd, J = 4.8, 1.5 Hz), 8.84 (1H, d, J = 2.4 Hz). |
| 9 | CD$_3$OD | 2.24 (3H, s), 2.54 (3H, s), 3.77 (2H, s), 4.48 (2H, s), 5.27 (2H, s), 6.23 (1H, d, J = 0.7 Hz), 7.13 (1H, d, J = 1.2 Hz), 7.24-7.37 (7H, m), 7.48 (1H, d, J = 1.5 Hz), 7.57 (2H, d, J = 1.2 Hz). |
| 10 | CD$_3$OD | 2.19 (3H, s), 2.48 (3H, s), 3.80 (2H, s), 4.48 (2H, s), 5.07 (2H, s), 6.24 (1H, d, J = 0.7 Hz), 6.70 (1H, d, J = 0.9 Hz), 7.11 (1H, d, J = 1.2 Hz), 7.25-7.37 (7H, m), 7.56 (2H, d, J = 7.5 Hz). |
| 11 | CD$_3$OD | 2.28 (3H, s), 2.55 (3H, s), 4.08 (2H, s), 4.50 (2H, d, J = 4.9 Hz), 5.29 (2H, s), 6.24 (1H, d, J = 0.6 Hz), 6.57 (1H, s), 7.39 (2H, d, J = 8.7 Hz), 7.42 (2H, d, J = 8.9 Hz), 7.44-7.50 (3H, m), 7.77-7.80 (2H, m). |
| 12 | CD$_3$OD | 2.23 (3H, s), 2.52 (3H, s), 3.78 (2H, s), 4.48 (2H, s), 5.50 (2H, s), 6.29 (1H, d, J = 0.7 Hz), 7.29 (2H, d, J = 8.4 Hz), 7.32 (2H, d, J = 8.5 Hz), 7.41 (1H, ddd, J = 8.0, 8.0, 1.0 Hz), 7.51 (1H, ddd, J = 8.2, 8.2, 1.0 Hz), 7.92 (1H, d, J = 8.0 Hz), 7.96 (1H, d, J = 8.2 Hz). |
| 13 | d6-DMSO | 2.48-2.50 (6H, m) 3.89 (2H, s) 4.34 (2H, d, J = 8.0 Hz) 5.26 (2H, d, J = 8.0 Hz) 6.29 (1H, s) 7.17-7.43 (8H, m) 7.91 (1H, d, J = 4.0 Hz) 8.48 (1H, dd, J = 8.0, 4.0 Hz) 8.90 (1H, s) |
| 14 | CD$_3$OD | 2.16 (3H, s) 2.43 (3H, s) 3.72 (2H, s) 4.36 (2H, s) 5.21 (2H, s) 6.19 (1H, s) 7.16-7.33 (5H, m) 7.48-7.59 (2H, m) 7.76-7.79 (1H, m) 8.39-8.44 (2H, m) |
| 15 | d6-DMSO | 2.12 (3H, s), 2.40 (3H, s), 2.62-2.85 (2H, s, br), 3.21-3.37 (2H, br), 3.41 (4H, t, J = 5.0 Hz), 3.65-3.69 (4H, m), 4.32 (2H, d, J = 6.0 Hz), 4.93 (2H, s), 5.99 (1H, d, J = 7.3 Hz), 6.29 (1H, d, J = 0.6 Hz), 6.70 (1H, d, J = 8.5 Hz), 7.20 (2H, d, J = 8.0 Hz), 7.25 (2H, d, J = 8.0 Hz), 7.48 (1H, dd, J = 7.5, 8.5 Hz), 8.02 (1H, t, J = 6.0 Hz) |
| 16 | d6-DMSO | 2.17 (3H, s), 2.46 (3H, s), 3.28-3.48 (2H, s, br), 3.73 (2H, s), 4.33 (2H, d, J = 6.0 Hz), 5.21 (2H, d), 6.34 (1H, d, J = 0.5 Hz), 6.67-6.72 (1H, m), 7.23 (2H, d, J = 8.1 Hz), 7.27 (2H, d, J = 9.2 Hz), 7.41-7.52 (3H, m), 7.82-7.89 (2H, m), 8.06-8.08 (2H, m), 8.14 (1H, t, J = 6.0 Hz) |
| 17 | d6-DMSO | 2.17 (3H, s), 2.46 (3H, s), 3.28-3.45 (2H, s, br), 3.68 (2H, s), 4.33 (2H, d, J = 6.1 Hz), 5.24 (2H, s), 6.34 (1H, d, J = 0.6 Hz), 6.79 (1H, d, J = 7.5 Hz), 7.21 (2H, d, J = 8.1 Hz), 7.25 (2H, d, J = 8.1 Hz), 7.51-7.54 (1H, m), 7.89 (1H, t, J = 7.7 Hz), 7.97 (1H, d, J = 7.5 Hz), 8.11 (1H, t, J = 6.1 Hz), 8.39 (1H, dt, J = 1.9, 7.9 Hz), 8.64 (1H, dd, J = 1.6, 5.0 Hz), 9.23-9.26 (1H, m) |
| 18 | CD$_3$OD | 2.26 (3H, s), 2.56 (3H, s), 3.73 (2H, s), 4.41 (2H, s), 4.91 (2H, s), 6.20 (1H, s), 7.24-7.30 (4H, m), 7.42-7.45 (3H, m), 7.51 (1H, s), 7.93-7.97 (2H, m). |
| 19 | d6-DMSO | 2.25 (3H, s), 2.26 (3H, s), 2.55 (3H, s), 3.97 (2H, dt, J = 11.4, 5.6 Hz), 4.33 (2H, d, J = 5.9 Hz), 4.94 (2H, s), 6.26 (1H, s), 7.30 (2H, d, J = 8.1 Hz), 7.39 (2H, d, J = 8.1 Hz), 7.48-7.51 (3H, m), 7.86-7.89 (2H, m), 8.11 (1H, t, J = 6.0 Hz), 8.20-8.45 (2H, s, br) |
| 20 | CD$_3$OD | 7.52-7.42 (4H, m), 7.36 (1H, dd, J = 5.0, 1.0 Hz), 7.00 (1H, dd, J = 5.0, 3.0 Hz), 6.85 (1H, dd, J = 3.0, 1.0 Hz), 6.27 (1H, s), 5.31 (2H, d, J = 0.6 Hz), 4.57 (2H, s), 4.14 (2H, s), 2.55 (3H, s), 2.28 (3H, s). |
| 21 | CD$_3$OD | 2.22 (3H, s), 2.52 (3H, s), 3.76 (2H, s), 4.46 (2H, s), 5.23 (2H, s), 6.24 (1H, d, J = 0.7 Hz), 6.80 (1H, d, J = 3.7 Hz), 7.24-7.31 (5H, m), 7.36-7.40 (1H, m), 7.92 (1H, dd, J = 8.0, 1.6 Hz), 8.38 (1H, dd, J = 5.0, 1.5 Hz), 8.68 (1H, dd, J = 1.6, 0.7 Hz). |
| 22 | CD$_3$OD | 2.23 (3H, s), 2.52 (3H, s), 3.78 (2H, s), 4.47 (2H, s), 5.20 (2H, s), 6.22 (1H, s), 6.73 (1H, d, J = 3.6 Hz), 7.18 (1H, d, J = 3.8 Hz), 7.21-7.36 (7H, m), 7.57 (2H, d, J = 7.3 Hz). |
| 23 | CD$_3$OD | 2.23 (3H, s), 2.52 (3H, s), 2.66 (3H, s), 3.94 (2H, s), 4.48 (2H, s), 5.22 (2H, s), 6.23 (1H, d, J = 0.8 Hz), 6.75 (1H, d, J = 3.8 Hz), 7.27 (1H, d, J = 3.6 Hz), 7.33 (2H, d, J = 8.6 Hz), 7.36 (2H, d, J = 8.6 Hz), 7.40 (1H, s). |
| 24 | CD$_3$OD | 2.28 (3H, s), 3.80 (2H, s), 4.32 (2H, s), 5.03 (2H, d, J = 0.7 Hz), 6.41 (1H, d, J = 0.7 Hz), 6.69 (1H, s), 7.08 (2H, d, J = 8.0 Hz), 7.23 (2H, d, J = 8.1 Hz), 7.32-7.36 (5H, m), 7.41-7.43 (3H, m), 7.84-7.86 (2H, m). |

TABLE 14-continued

NMR data of examples

| Example No | Solvent | Chemical Shift (ppm) |
|---|---|---|
| 25 | d6-DMSO | 2.53(3H, s), 3.28(2H, br s), 3.66(2H, s), 4.33(2H, d, J = 6.1 Hz), 5.21(2H, s), 6.53(1H, d, J = 3.1 Hz), 6.79(1H, d, J = 3.1 Hz), 7.15-7.24(4H, m), 7.30(1H, s), 7.47-7.51 (3H, m), 7.88-7.93(2H, m), 8.13(1H, t, J = 6.1 Hz). |
| 26 | CD$_3$OD | 2.25 (3H, s), 2.52 (3H, s), 4.06 (2H, s), 4.50 (2H, s), 5.16 (2H, d, J = 0.7 Hz), 6.24 (1H, s), 6.73 (1H, s), 7.11 (1H, d, J = 5.0, 3.6 Hz), 7.38 (2H, d, J = 8.6 Hz), 7.41 (2H, d, J = 8.6 Hz), 7.55 (1H, dd, J = 5.0, 1.0 Hz), 7.41 (1H, dd, J = 3.5, 1.0 Hz). |
| 27 | CD$_3$OD | 2.27 (3H, s), 2.54 (3H, s), 4.05 (2H, s), 4.50 (2H, s), 5.22 (2H, d, J = 0.7 Hz), 6.24 (1H, d, J = 0.7 Hz), 6.84 (1H, s), 7.38 (2H, d, J = 8.5 Hz), 7.41 (2H, d, J = 8.5 Hz), 7.45-7.47 (2H, m), 7.82-7.85 (1H, m), 7.95 (1H, dd, J = 2.2, 1.4 Hz). |
| 28 | CD$_3$OD | 2.25 (3H, s), 2.54 (3H, s), 3.79 (2H, s), 4.47 (2H, s), 5.20 (2H, s), 6.23 (1H, d, J = 0.7 Hz), 6.88 (1H, s), 7.28 (2H, d, J = 8.4 Hz), 7.41 (2H, d, J = 8.4 Hz), 7.47 (2H, d, J = 8.6 Hz), 7.91 (2H, d, J = 8.6 Hz). |
| 29 | d6-DMSO | 2.24(3H, s), 2.53(3H, s), 3.10-3.43 (2H, s, br), 3.66(2H, s), 4.31(2H, d, J = 6.0 Hz), 5.16(2H, s), 6.28(1H, s), 7.15-7.24(4H, m), 7.30(1H, s), 7.33-7.35(1H, m), 7.52-7.57(1H, m), 7.66-7.69(1H, m), 7.73-7.75(1H, m), 8.02(1H, t, J = 6.1 Hz). |
| 30 | d6-DMSO | 2.24(3H, s), 2.37(3H, s), 2.54(3H, s), 2.80-3.38 (2H, br s), 3.66(2H, s), 4.32(2H, d, J = 6.0 Hz), 5.15(2H, s), 6.29(1H, s), 7.15-7.24(5H, m), 7.29(1H, d, J = 7.6 Hz), 7.37(1H, t, J = 7.6 Hz), 7.69(2H, d, J = 9.2 Hz), 8.03(1H, t, J = 6.1 Hz). |
| 31 | d6-DMSO | 2.26 (3H, s), 2.54 (3H, s), 2.80 (2H, s), 4.33 (2H, d, J = 6.0 Hz), 5.19 (2H, s), 5.20-5.55 (2H, s, br), 6.29 (1H, s), 7.24 (2H, d, J = 8.0 Hz), 7.30 (2H, d, J = 8.1 Hz), 7.36 (1H, s), 7.54 (1H, ddd, J = 8.0, 4.9, 0.6 Hz), 8.08 (1H, t, J = 6.1 Hz), 8.26 (1H, dt, J = 8.2, 1.8 Hz), 8.67 (1H, dd, J = 4.8, 1.6 Hz), 9.09 (1H, d, J = 1.8 Hz). |
| 32 | CD$_3$OD | 2.25 (3H, s), 2.55 (3H, s), 3.77 (2H, s), 4.47 (2H, s), 5.21 (2H, s), 6.24 (1H, s), 7.09 (1H, s), 7.26-7.32 (4H, m), 7.87 (2H, dd, J = 4.8, 1.4 Hz), 8.60 (2H, dd, J = 4.7, 1.5 Hz). |
| 33 | CD$_3$OD | 2.25 (3H, s), 2.54 (3H, s), 3.20-3.45 (2H, br s), 3.66 (2H, s), 3.82 (3H, s), 4.32 (2H, d, J = 6.1 Hz), 5.16 (2H, s), 6.29 (1H, s), 7.05-7.08 (1H, m), 7.18-7.25 (5H, m), 7.38-7.48 (3H, m), 8.04 (1H, t, J = 6.1 Hz). |
| 34 | d6-DMSO | 2.25 (3H, s), 2.54 (3H, s), 3.20-3.40 (2H, br s), 3.71 (2H, s), 3.81 (3H, s), 4.32 (2H, d, J = 6.0 Hz), 5.13 (2H, s), 6.28 (1H, s), 7.05 (2H, dt, J = 8.9, 2.9 Hz), 7.14 (1H, s), 7.20 (2H, d, J = 8.2 Hz), 7.25 (2H, d, J = 8.1 Hz), 7.84 (2H, dt, J = 8.9, 2.9 Hz), 8.04 (1H, t, J = 6.1 Hz). |
| 35 | d6-DMSO | 2.08(2H, br s), 2.24(3H, s), 2.34(3H, s), 2.54(3H, s), 3.65(2H, s), 4.31(2H, d, J = 6.1 Hz), 5.14(2H, s), 6.28(1H, s), 7.17-7.24(5H, m), 7.30(2H, d, J = 8.1 Hz), 7.78(2H, d, J = 8.1 Hz), 8.02(1H, t, J = 6.0 Hz). |
| 36 | CD$_3$OD | 2.24 (3H, s), 2.55 (3H, s), 3.78 (2H, s), 4.47 (2H, s), 5.18 (2H, s), 6.23 (1H, d, J = 0.7 Hz), 6.95 (1H, s), 7.27 (2H, d, J = 8.2 Hz), 7.31 (2H, d, J = 8.2 Hz), 7.37-7.40 (1H, m), 7.86 (1H, dt, J = 7.8, 6.1 Hz), 8.10 (1H, d, J = 8.0 Hz), 8.51-8.53 (1H, m). |
| 37 | CD$_3$OD | 2.26 (3H, s), 2.56 (3H, s), 3.88 (2H, s), 4.52 (2H, s), 5.21 (2H, s), 6.28 (1H, s), 6.73 (1H, s), 7.34 (2H, d, J = 8.3 Hz), 7.37 (2H, d, J = 8.3 Hz), 7.54-7.59 (2H, m), 7.99 (1H, dd, J = 2.8, 1.4 Hz). |
| 38 | d6-DMSO | 2.18 (3H, s), 2.48 (3H, s), 3.22-3.36 (2H, br s), 3.68 (2H, s), 4.28 (2H, s), 4.31 (2H, d, J = 6.1 Hz), 5.10 (2H, s), 6.25 (1H, d, J = 0.6 Hz), 6.98 (1H, s), 7.18-7.28 (5H, m), 7.31-7.35 (4H, m), 8.02 (1H, t, J = 6.1 Hz) |
| 39 | d6-DMSO | 2.22 (3H, s), 2.51 (3H, s), 3.78 (2H, s), 4.33 (2H, d, J = 6.0 Hz), 4.72-5.10 (2H, br s), 5.12 (2H, s), 6.29 (1H, s), 6.89 (1H, dd, J = 1.1, 0.9 Hz), 7.05 (1H, s), 7.24 (2H, d, J = 8.1 Hz), 7.30 (2H, d, J = 8.1 Hz), 7.82 (1H, dd, J = 1.8, 1.6 Hz), 8.07 (1H, t, J = 6.1 Hz), 8.36 (1H, dd, J = 1.2, 1.0 Hz). |
| 40 | d6-DMSO | 2.26 (3H, s), 2.54 (3H, s), 3.96 (2H, s), 4.35 (2H, d, J = 6.1 Hz), 5.22 (2H, s), 6.32 (1H, s), 7.30 (2H, d, J = 8.1 Hz), 7.41 (2H, d, J = 8.1 Hz), 7.46 (1H, s), 7.46-7.70 (2H, br s), 8.17 (1H, t, J = 6.1 Hz), 8.71 (1H, d, J = 1.8 |

TABLE 14-continued

NMR data of examples

| Example No | Solvent | Chemical Shift (ppm) |
|---|---|---|
| | | Hz), 8.74 (1H, dd, J = 14.3, 1.5 Hz), 9.24(1H, d, J = 1.4 Hz). |
| 41 | d6-DMSO | 1.34 (3H, t, J = 7.0 Hz), 2.25 (3H, s), 2.54 (3H, s), 3.26-3.46 (2H, br), 3.69 (2H, s), 4.08 (2H, q, J = 7.0 Hz), 4.32 (2H, d, J = 6.0 Hz), 5.12 (2H, s), 6.28 (1H, s), 7.02 (2H, d, J = 8.8 Hz), 7.15 (1H, s), 7.20 (2H, d, J = 7.9 Hz), 7.24 (2H, d, J = 7.9 Hz), 7.82 (2H, d, J = 8.8 Hz), 8.03 (1H, t, J = 6.0 Hz) |
| 42 | d6-DMSO | 1.38 (3H, d, J = 7.0 Hz), 2.26 (3H, s), 2.33 (3H, t, J = 2.0 Hz), 2.67 (1H, t, J = 1.7 Hz), 3.28 (2H, d, J = 10.5 Hz), 3.37 (1H, s), 3.65 (2H, s), 5.15 (2H, s), 6.39 (1H, s), 7.22-7.28 (5H, m), 7.49 (2H, d, J = 1.8 Hz), 7.50 (1H, d, J = 2.6 Hz), 7.88 (1H, d, J = 1.7 Hz), 7.90 (1H, d, J = 3.0 Hz) |
| 43 | d6-DMSO | 2.25(3H, s), 2.53(3H, s), 3.32(2H, s, br), 3.82(2H, s), 4.33(2H, d, J = 6.0 Hz), 5.15(2H, s), 6.26(1H, s), 7.25(1H, s), 7.35(1H, d, J = 8.0 Hz), 7.47-7.52(3H, m), 7.63(1H, dd, J = 8.0, 2.1 Hz), 7.88-7.92(2H, m), 8.12 (1H, t, J = 6.1 Hz), 8.41(1H, s). |
| 44 | d6-DMSO | 2.10(2H, br s), 2.24(3H, s), 2.53(3H, s), 3.74(2H, s), 4.37(2H, d, J = 6.4 Hz), 5.16(2H, s), 6.26(1H, s), 7.30(1H, s), 7.34(2H, d, J = 7.7 Hz), 7.52-7.57(1H, m), 7.62(1H, dd, J = 8.0, 2.2 Hz), 7.65-7.75(2H, m), 8.10(1H, t, J = 6.0 Hz), 8.38(1H, d, J = 1.8 Hz). |
| 45 | CD$_3$OD | 2.23(3H, s), 2.54(3H, s), 3.81(2H, s), 4.46(2H, s), 5.17(2H, s), 6.25(1H, d, J = 0.8 Hz), 6.79(1H, s), 7.06(1H, dd, J = 11.1, 1.2 Hz), 7.12(1H, dd, J = 7.9, 1.3 Hz), 7.32(1H, t, J = 7.8 Hz), 7.42-7.45(3H, m), 7.89-7.91(2H, m). |
| 46 | d6-DMSO | 2.27(3H, s), 2.31(3H, s), 2.55(3H, s), 3.99(2H, q, J = 5.7 Hz), 4.31(2H, d, J = 6.0 Hz), 5.16(2H, s), 6.28(1H, s), 7.14-7.15(2H, m), 7.26-7.29(2H, m), 7.49-7.53(3H, m), 7.89-7.91(2H, m), 8.03(2H, s, s, br), 8.09(1H, t, J = 6.0 Hz). |
| 47 | d6-DMSO | 2.27(3H, s), 2.54(3H, s) 3.33(2H, S), 3.89(2H, s), 4.37(2H, d, J = 5.9 Hz), 5.17(2H, s), 6.31(1H, s), 7.17(1H, d, J = 7.9 Hz), 7.23-7.32(3H, m), 7.49-7.52(3H, s), 7.88-7.91(2H, m), 8.09(1H, t, J = 5.6 Hz). |
| 48 | d6-DMSO | 1.46 (3H, d, J = 6.8 Hz), 2.27 (3H, s, br), 2.32-2.33 (2H, m), 2.66-2.68 (1H, m), 4.35 (3H, d, J = 6.1 Hz), 5.16 (2H, s), 6.28 (1H, s), 7.29 (1H, s), 7.32 (2H, d, J = 8.1 Hz), 7.37 (2H, d, J = 8.1 Hz), 7.50 (3H, dd, J = 5.2 Hz, 1.9 Hz), 7.89-7.91 (2H,. m), 8.12 (3H, s, s, br) |
| 49 | d6-DMSO | 2.28(3H, s), 2.55(3H, s), 2.77(2H, br s), 3.69(2H, s), 4.38(2H, d, J = 6.0 Hz), 5.18(2H, s), 6.34(1H, d, J = 0.6 Hz), 7.21(2H, s), 7.30(1H, s), 7.41(1H, s), 7.49-7.55(3H, m), 7.90-7.92(2H, m), 8.07(1H, t, J = 6.0 Hz). |
| 50 | d6-DMSO | 2.29(3H, s), 2.56(3H, s), 3.07(2H, br s), 3.78(2H, s), 4.51(2H, d, J = 5.6 Hz), 5.18(2H, s), 6.35(1H, s), 7.32(1H, s), 7.39(1H, d, J = 8.0 Hz), 7.49-7.55(4H, m), 7.69(1H, s), 7.90-7.92(2H, m), 8.13(1H, t, J = 5.8 Hz). |
| 51 | d6-DMSO | 1.46 (3H, d, J = 6.8 Hz), 2.27 (3H, br.s), 2.32-2.33 (1H, m), 2.59-2.60 (1H, m), 2.66-2.68 (1H, m), 4.35 (3H, d, J = 6.1 Hz), 5.17 (2H, s), 6.28 (1H, s), 7.29 (1H, s), 7.32 (2H, d, J = 8.3 Hz), 7.38 (2H, d, J = 8.3 Hz), 7.50 (3H, dd, J = 5.1 Hz, 1.9 Hz), 7.89-7.92 (2H . m), 8.12 (3H, s, br) |
| 52 | d6-DMSO | 0.85 (2H, t, J = 7.2 Hz), 1.66-1.81 (2H, m), 2.26 (3H, s), 3.28 (1H, d, J = 11.0 Hz), 3.65 (2H, s), 4.79 (1H, q, J = 8.8 Hz), 5.14 (2H, s), 6.40 (1H, s), 7.21-7.27 (5H, m), 7.48 (2H, d, J = 1.8 Hz), 7.50 (1H, d, J = 2.3 Hz), 7.66 (1H, d, J = 8.4 Hz), 7.88 (1H, d, J = 1.6 Hz), 7.90 (1H, d, J = 2.8 Hz) (3H, s, obscured by DMSO) |
| 53 | d6-DMSO | 2.26 (3H, s), 2.55 (3H, s), 3.75-3.80 (2H, s, brs), 3.78 (3H, s), 4.33-4.35 (2H, d, J = 6.0 Hz), 5.16 (2H, s), 6.29 (1H, s), 6.83-6.85 (1H, d, J = 7.6 Hz), 6.95 (1H, s), 7.22-7.24 (1H, d, J = 7.7 Hz), 7.28 (1H, s), 7.48-7.52 (3H, m), 7.89-7.91 (2H, m), 8.06-8.09 (1H, t, J = 6.0 Hz) |
| 54 | d6-DMSO | 2.27 (3H, s), 2.54 (3H, s), 3.68 (2H, s, br), 3.81 (3H, s), 4.29-4.30 (2H, d, J = 5.9 Hz), 5.17 (2H, s), 6.32 (1H, s), 6.80-6.82 (1H, d, J = 7.6 Hz), 6.96 (1H, s), 7.04-7.06 (1H, d, J = 7.6 Hz), 7.27 (1H, s), 7.48-7.52 (3H, m), 7.78-7.85 (1H, m), 7.89-7.92 (2H, m) |

TABLE 14-continued

NMR data of examples

| Example No | Solvent | Chemical Shift (ppm) |
|---|---|---|
| 55 | CD$_3$OD | 2.18 (3H, s), 2.46 (3H, s), 4.14 (2H, s), 4.57 (2H, s), 5.18 (2H, s), 6.31 (1H, s), 6.96 (2H, d, J = 7.5 Hz), 7.29-7.31 (1H, m), 7.34-7.39 (2H, m), 7.44-7.50 (4H, m). |
| 56 | CD$_3$OD | 2.20 (3H, s), 2.46 (3H, s), 4.15 (2H, s), 4.65 (2H, d, J = 5.5 Hz), 5.19 (2H, s), 6.35 (1H, d, J = 0.6 Hz), 6.97 (2H, d, J = 7.2 Hz), 7.28-7.42 (4H, m), 7.51 (1H, d, J = 8.0 Hz), 7.58 (1H, d, J = 1.6 Hz). |
| 57 | CD$_3$OD | 2.20 (3H, s), 3.76 (2H, s), 4.22 (2H, s), 4.84 (2H, s), 6.30 (1H, d, J = 0.7 Hz), 6.70 (2H, d, J = 7.1 Hz), 7.00 (2H, d, J = 8.0 Hz), 7.04-7.26 (10H, m). |
| 58 | d6-DMSO | 1.29 (3H, t, J = 7.0 Hz), 2.07 (3H, s), 2.36 (3H, s), 3.46-3.89 (2H, br s), 3.74 (2H, s), 3.95 (2H, q, J = 7.0 Hz), 4.34 (2H, d, J = 6.0 Hz), 5.04 (2H, s), 6.33 (1H, s), 6.37 (1H, s), 6.44 (1H, d, J = 7.6 Hz), 6.80 (1H, dd, J = 8.1, 2.3 Hz), 7.17-7.29 (5H, m), 8.12 (1H, t, J = 6.1 Hz). |
| 59 | d6-DMSO | 1.29 (3H, t, J = 7.0 Hz), 2.07 (3H, s), 2.37 (3H, s), 3.74 (2H, s), 3.74-4.10 (2H, br s), 3.96 (2H, q, J = 7.0 Hz), 4.33 (2H, d, J = 6.0 Hz), 4.99 (2H, s), 6.31 (1H, s), 6.81 (2H, d, J = 8.8 Hz), 6.87 (2H, d, J = 8.7 Hz), 7.23 (2H, d, J = 8.2 Hz), 7.28 (2H, d, J = 8.2 Hz), 8.10 (1H, t, J = 6.1 Hz). |
| 60 | d6-DMSO | 2.08 (3H, s), 3.37 (2H, s), 3.98 (2H, q, J = 5.6 Hz), 4.35 (2H, d, J = 6.1 Hz), 5.00 (2H, s), 5.06 (2H, s), 6.32 (1H, s), 6.83 (2H, d, J = 8.6 Hz), 6.96 (2H, d, J = 8.6 Hz), 7.28-7.35 (4H, m), 7.37-7.45 (6H, m), 8.14 (1H, t, J = 6.1 Hz), 8.27-8.38 (2H, s, br) |
| 61 | d6-DMSO | 2.08 (3H, s), 2.37 (3H, s), 3.71 (3H, s), 3.99 (2H, q, J = 5.7 Hz), 4.35 (2H, d, J = 6.1 Hz), 5.00 (2H, s), 6.31 (1H, s), 6.83 (2H, d, J = 8.8 Hz), 6.89 (2H, d, J = 8.8 Hz), 7.31 (2H, d, J = 8.1 Hz), 7.40 (2H, d, J = 8.1 Hz), 8.14 (1H, t, J = 6.1 Hz), 8.23-8.35 (2H, s, br) |
| 62 | d6-DMSO | 2.08 (3H, s), 2.37 (3H, s), 3.98 (2H, d, J = 5.8 Hz), 4.36 (2H, d, J = 6.0 Hz), 5.13 (2H, s), 6.33 (1H, s), 7.32 (2H, d, J = 8.2 Hz), 7.35-7.42 (5H, m), 7.51 (1H, s), 7.74 (1H, d, J = 7.8 Hz), 7.97 (1H, s), 8.19 (1H, t, J = 6.0 Hz), 8.20-8.29 (2H, s, br) |
| 63 | d6-DMSO | 2.07 (3H, s), 2.36 (3H, s), 3.99 (2H, q, J = 5.8 Hz), 4.24 (2H, d, J = 6.0 Hz), 5.14 (2H, s), 6.35 (1H, s), 6.94 (2H, d, J = 8.3 Hz), 7.32 (3H, d, J = 8.1 Hz), 7.40 (2H, d, J = 8.1 Hz), 7.81 (2H, d, J = 8.3 Hz), 7.92 (1H, s), 8.17 (1H, t, J = 6.0 Hz), 8.19-8.27 (2H, s, br) |
| 64 | d6-DMSO | 2.07 (3H, s), 2.36 (3H, s), 3.99 (2H, q, J = 5.6 Hz), 4.36 (2H, d, J = 6.0 Hz), 5.17 (2H, s), 6.36 (1H, s), 7.19 (1H, d, J = 7.3 Hz), 7.31 (1H, s), 7.32 (2H, d, J = 8.0 Hz), 7.39 (2H, d, J = 8.0 Hz), 7.56 (1H, t, J = 7.8 Hz), 7.74 (1H, d, J = 7.7 Hz), 8.15-8.28 (3H, m) |
| 65 | d6-DMSO | 2.05 (3H, s), 2.34 (3H, s), 3.99 (2H, q, J = 5.7 Hz), 4.336 (2H, d, J = 6.0 Hz), 5.21 (2H, s), 6.36 (1H, s), 7.04 (2H, d, J = 8.2 Hz), 7.32 (2H, d, J = 8.0 Hz), 7.40 (2H, d, J = 8.0 Hz), 7.81 (2H, d, J = 8.2 Hz), 8.18 (1H, t, J = 6.0 Hz), 8.25-8.34 (2H, s, br) |
| 66 | d6-DMSO | 2.10 (3H, s), 2.39 (3H, s), 3.98 (4H, d, J = 5.2 Hz), 4.36 (2H, d, J = 6.1 Hz), 5.09 (2H, s), 6.34 (1H, s), 6.83-6.87 (1H, m), 7.13 (1H, s), 7.31 (2H, d, J = 8.1 Hz), 7.36 (2H, d, J = 3.4 Hz), 7.40 (2H, d, J = 8.1 Hz), 8.17 (1H, t, J = 6.1 Hz), 8.24-8.38 (4H, s, br) |
| 67 | d6-DMSO | 2.07 (3H, s), 2.36 (3H, s), 3.70 (4H, s), 4.36 (2H, d, J = 6.1 Hz), 5.11 (2H, s), 6.35 (1H, s), 6.92 (2H, d, J = 8.1 Hz), 7.31 (2H, d, J = 8.1 Hz), 7.40 (2H, d, J = 8.1 Hz), 7.43 (2H, d, J = 8.1 Hz), 8.17 (1H, t, J = 6.1 Hz), 8.23-8.36 (4H, s, br) |
| 68 | d6-DMSO | 1.84 (3H, s), 2.07 (3H, s), 2.36 (3H, s), 3.98 (2H, dt, J = 5.8, 5.7 Hz), 4.19 (2H, d, J = 5.9 Hz), 4.36 (2H, d, J = 6.0 Hz), 5.06 (2H, s), 6.32 (1H, s), 6.84 (2H, d, J = 8.1 Hz), 7.19 (2H, d, J = 8.1 Hz), 7.32 (2H, d, J = 8.1 Hz), 7.40 (2H, d, J = 8.2 Hz), 8.15 (1H, t, J = 6.1 Hz), 8.25 (2H, s, br), 8.31 (1H, d, J = 6.0 Hz). |
| 69 | d6-DMSO | 2.10(3H, s), 2.40(3H, s), 2.72(2H, s, br), 3.69(2H, s), 4.33(2H, d, J = 6.1 Hz), 5.16(2H, s), 6.34(1H, s), 6.80(1H, d, J = 7.7 Hz), 7.20-7.26(5H, m), 7.34-7.47(4H, m), 7.52-7.63(3H, m), 8.08(1H, t, J = 6.1 Hz). |
| 70 | d6-DMSO | 2.10(3H, s), 2.20(2H, s, br), 2.40(3H, s), 3.67(2H, s), 4.33(2H, d, J = 6.0 Hz), 5.13(2H, s), 6.34(1H, s), 6.97(2H, d, J = 8.2 Hz), 7.20-7.26(4H, m), 7.32- |

TABLE 14-continued

NMR data of examples

| Example No | Solvent | Chemical Shift (ppm) |
|---|---|---|
| | | 7.39(1H, m), 7.41-7.47(2H, m), 7.52-7.63(4H, m), 8.08(1H, t, J = 6.1 Hz). |
| 71 | d6-DMSO | 2.11 (3H, s), 2.41 (3H, s), 3.20-3.40 (2H, s, br), 3.69 (2H, s), 4.33 (2H, d, J = 6.1 Hz), 5.18 (2H, s), 6.34 (1H, s), 6.82 (1H, d, J = 7.5 Hz), 7.21 (2H, d, J = 8.1 Hz), 7.25 (2H, d, J = 8.1 Hz), 7.34 (1H, s), 7.45 (1H, t, J = 7.5 Hz), 7.47-7.50 (1H, m), 7.61 (1H, d, J = 7.9 Hz), 7.99-8.01 (1H, m), 8.09 (1H, t, J = 6.1 Hz), 8.57 (1H, dd, J = 1.5, 5.0 Hz), 8.81-8.83 (1H, m) |
| 72 | d6-DMSO | 2.11 (3H, s), 2.41 (3H, s), 3.20-3.40 (2H, br s), 3.68 (2H, s), 4.33 (2H, d, J = 6.1 Hz), 5.19 (2H, s), 6.36 (1H, s), 6.86 (1H, d, J = 7.5 Hz), 7.23 (2H, d, J = 8.1 Hz), 7.25 (2H, d, J = 8.1 Hz), 7.43 (1H, s), 7.45 (1H, t, J = 7.5 Hz), 7.62 (2H, dd, J = 1.5, 4.5 Hz), 7.68 (1H, d, J = 7.5 Hz), 8.09 (1H, t, J = 6.1 Hz), 8.63 (2H, dd, J = 1.5, 4.5 Hz) |
| 73 | d6-DMSO | 2.08 (3H, s), 2.37 (3H, s), 3.04 (4H, t, J = 4.9 Hz), 3.23-3.37 (2H, s, br), 3.68 (2H, s), 3.71 (4H, t, J = 4.9 Hz), 4.33 (2H, d, J = 6.1 Hz), 5.01 (2H, s), 6.19 (1H, 7.6 Hz), 6.31 (1H, s), 6.61 (1H, s), 6.81 (1H, dd, J = 2.1, 9.2 Hz), 7.12-7.15 (1H, m), 7.20 (2H, d, J = 8.2 Hz), 7.25 (2H, d, J = 8.2 Hz), 8.05 (1H, t, J = 6.1 Hz) |
| 74 | d6-DMSO | 1.48-1.54 (2H, m), 1.55-1.59 (4H, m), 2.08 (3H, s), 2.37 (3H, s), 3.05-3.09 (4H, m) 3.25-3.36 (2H, s, br), 3.72 (2H, s), 4.33 (2H, d, J = 6.0 Hz), 5.00 (2H, s)m 6.16 (1H, d, J = 7.5 Hz), 6.31 (1H, s), 6.55 (1H, s), 6.78 (1H, dd, J = 2.0, 8.2 Hz), 7.10 (1H, t, J = 7.8 Hz), 7.22 (2H, d, J = 8.2 Hz), 7.26 (2H, d, J = 8.2 Hz), 8.06 (1H, t, J = 6.0 Hz) |
| 75 | CD$_3$OD | 2.05 (3H, s), 3.61 (3H, s), 3.91 (2H, s), 3.97 (2H, s), 4.46 (2H, s), 6.65 (1H, s), 7.03 (2H, d, J = 7.2 Hz), 7.15 (1H, d, J = 7.3 Hz), 7.22 (2H, d, J = 7.6 Hz), 7.34 (4H, s). |
| 76 | d6-DMSO | 1.92 (3H, s), 3.19-3.42 (2H, s, br), 3.67 (2H, s), 3.85 (2H, s), 4.36 (2H, d, J = 6.1 Hz), 6.57 (1H, d, J = 2.3 Hz), 7.12-7.30 (9H, m), 8.25 (1H, t, J = 6.0 Hz), 11.10 (1H, s, br). |
| 77 | d6-DMSO | 0.91 (3H, t, J = 7.0 Hz), 2.01 (3H, s), 3.69 (2H, s), 3.96 (2H, s), 4.15 (2H, q, J = 7.0 Hz), 4.33 (2H, d, J = 6.1 Hz), 6.69 (1H, s), 7.07 (2H, d, J = 7.2 Hz), 7.14-7.22 (4H, m), 7.25-7.31 (5H, m), 8.36 (1H, t, J = 6.1 Hz) |
| 78 | d6-DMSO | 0.67 (3H, t, J = 7.6 Hz), 1.24-1.34 (2H, m), 2.01 (3H, s), 3.70 (2H, s), 3.95 (2H, s), 4.09 (2H, t, J = 7.6 Hz), 4.32 (2H, d, J = 6.1 Hz), 6.68 (1H, s), 7.07 (2H, d, J = 7.2 Hz), 7.16-7.22 (4H, m), 7.25-7.31 (5H, m), 8.35 (1H, t, J = 6.1 Hz) |
| 79 | d6-DMSO | 1.15 (6H, d, J = 7.6 Hz), 3.68-3.74 (1H, m), 4.00 (2H, s), 4.03-4.13 (1H, m), 4.41 (2H, d, J = 6.0 Hz), 5.40 (2H, s), 7.31-7.41 (6H, m), 7.82 (2H, d, J = 8.2 Hz), 7.93 (1H, s), 8.15 (2H, br.s + HCl salt), 8.28 (1H, s), 8.69 (1H, t, J = 6.0 Hz) |
| 80 | CD$_3$OD | 2.68 (3H, s), 3.89 (2H, s), 4.50 (2H, s), 5.46 (2H, s), 7.21 (1H, s), 7.33 (2H, d, J = 8.8 Hz), 7.36 (2H, d, J = 8.7 Hz), 7.39-7.46 (3H, m), 7.89-7.92 (3H, m). |
| 81 | CD$_3$OD | 2.40 (3H, s), 3.97 (2H, s), 4.48(2H, s), 5.40 (2H, s), 7.36 (4H, s), 7.41-7.46 (4H, m), 7.89-7.93 (2H, m), 8.16 (1H, s). |
| 82 | d6-DMSO | 3.98 (2H, q, J = 5.7 Hz), 4.39 (2H, d, J = 6.0 Hz), 5.61 (2H, s), 7.33 (2H, d, J = 8.1 Hz), 7.41 (2H, d, J = 8.0 Hz), 7.49-7.53 (3H, m), 7.76 (1H, s), 7.91-7.94 (2H, m), 8.15-8.40 (2H, s, br), 8.55 (2H, s), 8.94 (1H, t, J = 5.8 Hz) |
| 83 | d6-DMSO | 3.98 (2H, q, J = 5.64 Hz), 4.39 (2H, d, J = 5.96), 5.61 (2H, s), 7.32 (2H, d, J = 8.16), 7.42 (2H, d, J = 8.16 Hz), 7.50 (3H, m), 7.76 (1H, s), 7.93 (2H, d.d, J = 2.44, 7.16 Hz), 8.33 (2H, s, br), 8.56 (1H, s), 8.96 (1H, t) |
| 84 | CD$_3$OD | 4.05 (2H, s) 4.44 (2H, s) 5.25 (2H, s) 6.96-7.03 (2H, m) 7.22-7.36 (4H, m) 7.39-7.57 (7H, m) 7.66-7.68 (1H, m) 8.09 (1H, s) |
| 85 | d6-DMSO | 1.98 (3H, s), 3.98 (2H, q, J = 5.68 Hz), 4.38 (2H, d J = 5.92 Hz), 5.21 (2H, s), 5.31 (2H, s), 7.15 (2H, d, J = 5.68 Hz), 7.20 (2H, d, J = 8.16 Hz), 7.22 (2H, d, J = 7.60 Hz), 7.31 (2H, d, J = 8.08 Hz), 7.39 (2H, d, J = 8.04 Hz), 7.51 (1H, s), 7.53 (1H, s), 7.89 (1H, s), 8.25 (1H, s), 8.68 (1H, t, J = 6.08 Hz) |
| 86 | d6-DMSO | 2.08 (3H, s), 2.14 (3H, s), 3.98 (2H, q, J = 5.82 Hz), 4.39 (2H, d, J = 6.79 Hz), 5.16 (2H, s), 5.31 (2H, s), 7.07 (2H, d, J = 8.01 Hz), 7.22 (2H, d, J = 8.01 Hz), 7.32 |

TABLE 14-continued

NMR data of examples

| Example No | Solvent | Chemical Shift (ppm) |
|---|---|---|
| | | (2H, d, J = 8.33 Hz), 7.38 (2H, d, J = 8.33 Hz), 7.89 (1H, s), 8.08 (3H, s, br), 8.24 (1H, s), 8.67(1H, t, J = 5.90 Hz). |
| 87 | d6-DMSO | 3.23 (2H, s, br), 3.55 (2H, s, br), 3.88 (6H, s, br), 3.98 (2H, q, J = 5.8 Hz), 4.40 (2H, d, J = 6.0 Hz), 5.39 (2H, s), 7.27-7.36 (6H, m), 7.40 (2H, d, 8.1 Hz), 7.94 (1H, s), 8.25 (2H, s, br), 8.31 (1H, s), 8.71 (1H, s) |
| 88 | d6-DMSO | 3.99 (2H, q, J = 5.19 Hz), 4.41 (2H, d, J = 6.136 Hz), 5.45 (2H, s), 7.00-7.03 (4H, m), 7.14-7.18 (1H, m), 7.33-7.39 (7H, m), 8.07 (3H, s, br), 8.81 (1H, s), 9.07-9.10 (1H, m). |
| 89 | d6-DMSO | 0.88-0.95 (2H, m), 0.97-1.04 (2H, m), 2.50-2.70 (2H, br s), 4.33 (2H, d, J = 6.0 Hz), 5.07 (2H, s), 5.31 (2H, s), 6.21 (1H, td, J = 1.4, 6.7 Hz), 6.40 (1H, d, J = 9.2 Hz), 7.16-7.31 (8H, m), 7.40 (1H, ddd, J = 2.1, 6.6, 8.8 Hz), 7.75 (1H, dd, J = 1.5, 6.8 Hz), 7.87 (1H, s), 8.23 (1H, s), 8.55 (1H, t, J = 6.0 Hz). |
| 90 | d6-DMSO | 2.06 (3H, s), 2.35 (3H, s), 3.86 (2H, s), 4.35 (2H, d, J = 6.1 Hz), 5.06 (4H, s), 6.23 (1H, dt, J = 1.4, 6.7 Hz), 6.32 (1H, s), 6.40 (1H, d, J = 6.8 Hz), 6.86-6.88 (2H, m), 7.23-7.25 (2H, m), 7.27-7.29 (2H, m), 7.32-7.34 (2H, m), 7.42 (1H, ddd, J = 2.1, 6.6, 9.2 Hz), 7.75 (1H, ddd, J = 0.4, 2.0, 6.8 Hz), 8.11 (1H, t, J = 6.0 Hz). |
| 91 | d6-DMSO | 2.07 (3H, s), 2.28 (3H, s), 2.38 (3H, s), 3.67 (2H, s), 4.31 (2H, d, J = 5.8 Hz), 5.07 (4H, s), 6.24 (1H, td, J = 1.4, 6.7 Hz), 6.32-6.37 (1H, m), 6.42 (1H, dd, J = 0.7, 9.1 Hz), 6.87 (2H, d, J = 8.2 Hz), 7.09 (2H, m), 7.17 (1H, d, J = 7.7 Hz), 7.25 (2H, d, J = 8.2 Hz), 7.42 (1H, ddd, J = 2.1, 6.6, 8.8 Hz), 7.72-7.79 (1H, m), 7.93 (1H, t, J = 5.9 Hz). |
| 92 | d6-DMSO | 0.94 (3H, t, J = 7.0 Hz), 1.98 (3H, s), 2.28 (3H, s), 3.67 (2H, s), 3.92 (2H, s), 4.14 (2H, q, J = 7.0 Hz), 4.31 (2H, d, J = 5.8 Hz), 5.03 (2H, s), 6.21 (1H, td, J = 6.7, 1.4 Hz), 6.39 (1H, d, J = 9.1 Hz), 6.70 (1H, s), 7.03 (2H, d, J = 8.1 Hz), 7.06-7.16 (3H, m), 7.20 (2H, d, J = 8.2 Hz), 7.40 (1H, ddd, J = 8.9, 6.6, 2.1 Hz), 7.73 (1H, dd, J = 6.8, 1.6 Hz), 8.23 (1H, t, J = 5.9 Hz). |
| 93 | d6-DMSO | 0.80-0.88 (2H, m), 0.88-0.98 (5H, m), 1.98 (3H, s), 3.92 (2H, s), 4.13 (2H, q, J = 6.9 Hz), 4.31 (2H, d, J = 6.1 Hz), 5.03 (2H, s), 6.21 (1H, td, J = 6.7, 1.4 Hz), 6.39 (1H, d, J = 9.1 Hz), 6.67 (1H, s), 7.02 (2H, d, J = 8.1 Hz), 7.11-7.28 (6H, m), 7.40 (1H, ddd, J = 8.9, 6.6, 2.1 Hz), 7.73 (1H, dd, J = 6.8, 1.6 Hz), 8.32 (1H, t, J = 6.1 Hz). |
| 94 | d6-DMSO | 1.87 (1H, s), 1.96 (1H, t, J = 1.2 Hz), 2.01 (3H, s), 2.32-2.35 (8H, m), 3.69 (1H, s), 4.28 (1H, s), 4.34 (2H, d, J = 4.8 Hz), 5.03-5.04 (4H, m), 6.22 (1H, dt, J = 1.4, 6.7 Hz), 6.28-6.29 (1H, m), 6.38-6.40 (1H, m), 6.83-6.85 (2H, m), 6.92-6.93 (1H, m), 6.98 (1H, s), 7.21-7.23 (2H, m), 7.40 (1H, ddd, J = 2.1, 6.6, 9.2 Hz), 7.75 (1H, ddd, J = 0.4, 2.0, 6.8 Hz) ppm. NH2 not observed |
| 95 | d6-DMSO | 0.95 (3H, t, J = 6.8 Hz), 1.87 (2H, s), 1.94 (3H, s), 1.96 (2H, t, J = 1.24 Hz), 2.31 (6H, s), 3.91 (2H, s), 4.15 (2H, q, J = 6.8 Hz), 4.35 (2H, d, J = 4.9 Hz), 5.04 (2H, s), 6.21 (1H, dt, J = 1.4, 6.7 Hz), 6.38-6.41 (1H, m), 6.21-6.22 (1H, m), 6.89-6.96 (2H, m, 7.01-7.03 (2H, m), 7.19-7.21 (2H, m), 7.41 (1H, ddd, J = 2.1, 6.6, 9.1 Hz), 7.73-7.78 (2H, m) |
| 96 | d6-DMSO | 1.98 (3H, s), 2.07 (3H, s), 2.35 (3H, s), 2.69-3.03 (2H, br s), 3.69 (2H, s), 4.34 (2H, d, J = 6.1 Hz), 5.06 (2H, s), 5.19 (2H, s), 6.26-6.36 (1H, m), 6.85 (2H, d, J = 8.2 Hz), 7.15 (2H, d, J = 8.2 Hz), 7.18-7.31 (5H, m), 7.46-7.55 (1H, m), 8.07 (1H, t, J = 6.2 Hz). |
| 97 | d6-DMSO | 2.04 (3H, s), 2.11 (3H, s), 2.34 (3H, s), 2.41 (3H, s), 3.23 (2H, br s), 3.70 (2H, s), 4.36 (2H, d, J = 5.8 Hz), 5.11 (2H, s), 5.25 (2H, s), 6.40 (1H, s), 6.91 (2H, d, J = 8.0 Hz), 7.08-7.15 (2H, m), 7.19-7.22 (3H, m), 7.29 (1H, s), 7.58 (1H, s), 7.98 (1H, t, J = 5.5 Hz). |
| 98 | d6-DMSO | 0.82-0.90 (2H, m), 0.90-0.96 (2H, m), 1.97 (3H, s), 2.05 (3H, s), 2.35 (3H, s), 2.55 (2H, br s), 4.31 (2H, d, J = 6.1 Hz), 5.05 (2H, s), 5.19 (2H, s), 6.31 (1H, s), 6.84 (2H, d, J = 8.2 Hz), 7.11-7.21 (4H, m), 7.21-7.27 (3H, m), 7.52 (1H, s), 8.05 (1H, t, J = 6.1 Hz). |
| 99 | d6-DMSO | 0.94 (3H, t, J = 7.0 Hz), 1.82 (2H, s, br), 1.98 (6H, m), 2.27 (3H, s), 3.64 (2H, s), 3.92 (2H, s), 4.14 (2H, q, J = 6.9 Hz), 4.30 (2H, d, J = 5.9 Hz), 5.17 (2H, s), 6.70 (1H, |

TABLE 14-continued

NMR data of examples

| Example No | Solvent | Chemical Shift (ppm) |
|---|---|---|
| | | s), 7.02 (2H, d, J = 8.2 Hz), 7.04-7.17 (5H, m), 7.22 (1H, s), 7.49 (1H, s), 8.21 (1H, t, J = 5.9 Hz). |
| 100 | d6-DMSO | 0.82-0.88 (2H, m), 0.88-0.98 (5H, m), 1.98 (6H, s), 3.92 (2H, s), 4.13 (2H, q, J = 6.9 Hz), 4.31 (2H, d, J = 6.1 Hz), 5.17 (2H, s), 6.67 (1H, s), 7.01 (2H, d, J = 8.2 Hz), 7.11 (2H, d, J = 8.2 Hz), 7.16 (2H, d, J = 8.4 Hz), 7.19-7.26 (3H, m), 7.49 (1H, s), 8.32 (1H, t, J = 6.1 Hz). |
| 101 | d6-DMSO | 1.98 (3H, s), 2.01 (3H, s), 2.02-2.14 (2H, s, br), 2.32 (6H, s), 2.34 (3H, s), 3.61 (2H, s), 4.33 (2H, d, J = 5.0 Hz), 5.03 (2H, s), 5.18 (2H, s), 6.29 (1H, s), 6.83 (2H, d, J = 8.2 Hz), 6.95 (2H, s), 7.14 (2H, d, J = 8.2 Hz), 7.22 (1H, s), 7.42 (1H, t, J = 5.0 Hz), 7.51 (1H, s). |
| 102 | d6-DMSO | 0.94 (3H, t, J = 7.0 Hz), 1.94 (3H, s), 1.98 (3H, s), 2.32 (6H, s), 3.66 (2H, s), 3.90 (2H, s), 4.14 (2H, q, J = 6.9 Hz), 4.35 (2H, d, J = 5.0 Hz), 5.17 (2H, s), 6.61 (1H, s), 6.97-7.01 (m, 4H), 7.10 (2H, d, J = 8.2 Hz), 7.22 (1H, s), 7.49 (1H, s), 7.78 (1H, t, J = 5.0 Hz). |
| 103 | | 0.79-0.95 (4H, m), 1.98 (3H, s), 2.36 (2H, br s), 4.34 (2H, d, J = 5.9 Hz), 5.20 (2H, s), 5.30 (2H, s), 7.12-7.27 (9H, m), 7.51 (1H, s), 7.87 (1H, s), 8.22 (1H, s), 8.53 (1H, t, J = 6.0 Hz). |
| 104 | | 1.98 (3H, s), 3.20-3.40 (2H, br s), 3.70 (2H, s), 4.35 (2H, d, J = 6.4 Hz), 5.19 (2H, s), 5.21 (2H, s), 7.12-7.32 (9H, m), 7.52 (1H, d, J = 0.7 Hz), 7.67 (1H, d, J = 1.3 Hz), 7.81 (1H, d, J = 1.3 Hz), 8.38 (1H, t, J = 6.4 Hz). |
| 105 | | 0.81-0.89 (2H, m), 0.89-0.96 (2H, m), 1.98 (3H, s), 2.66 (2H, br s), 4.32 (2H, d, J = 6.4 Hz), 5.17 (2H, s), 5.21 (2H, s), 7.13-7.24 (7H, m), 7.27 (2H, d, J = 8.1 Hz), 7.51 (1H, s), 7.67 (1H, d, J = 1.3 Hz), 7.82 (1H, d, J = 1.2 Hz), 8.35 (1H, t, J = 6.4 Hz). |
| 106 | | 1.98 (3H, s), 2.27 (3H, s), 3.32 (2H, br s), 3.65 (2H, s), 4.34 (2H, d, J = 5.6 Hz), 5.21 (2H, s), 5.30 (2H, s), 7.05-7.25 (8H, m), 7.52 (1H, s), 7.89 (1H, s), 8.24 (1H, s), 8.38 (1H, t, J = 5.7 Hz). |
| 107 | | 1.98 (3H, s), 2.27 (3H, s), 2.19-2.41 (2H, br s), 3.64 (2H, s), 4.34 (2H, d, J = 6.2 Hz), 5.19 (2H, s), 5.21 (2H, s), 7.05 (1H, d, J = 7.9 Hz), 7.08-7.14 (2H, m), 7.18 (2H, d, J = 8.1 Hz), 7.23 (1H, s), 7.28 (2H, d, J = 8.1 Hz), 7.52 (1H, s), 7.69 (1H, d, J = 1.2 Hz), 7.82 (1H, d, J = 1.2 Hz), 8.17 (1H, t, J = 6.2 Hz). |
| 108 | | 1.98 (3H, s), 2.89 (2H, br s), 3.70 (2H, s), 4.39 (2H, d, J = 6.3 Hz), 5.22 (2H, s), 5.61 (2H, s), 7.11-7.36 (9H, m), 7.52 (1H, s), 8.61 (1H, s), 9.02 (1H, t, J = 6.2 Hz). |
| 109 | | 1.91 (2H, br s), 1.98 (3H, s), 2.28 (3H, s), 3.63 (2H, s), 4.38 (2H, d, J = 6.1 Hz), 5.22 (2H, s), 5.61 (2H, s), 7.01-7.16 (3H, m), 7.17-7.26 (3H, m), 7.31 (2H, d, J = 8.2 Hz), 7.52 (1H, s), 8.62 (1H, s), 8.85 (1H, t, J = 6.1 Hz). |
| 110 | | 0.87-1.11 (4H, m), 1.99 (3H, s), 4.39 (2H, d, J = 6.3 Hz), 4.80 (2H, s), 5.22 (2H, s), 5.62 (2H, s), 7.12-7.38 (9H, m), 7.53 (1H, s), 8.62 (1H, s), 9.03 (1H, t, J = 6.3 Hz). |
| 111 | d6-DMSO | 1.97 (3H, s), 2.14-2.30 (2H, s, br), 2.29 (6H, s), 3.62 (2H, s), 4.36 (2H, d, J = 4.8 Hz), 5.20 (2H, s), 5.27 (2H, s), 6.97 (2H, s), 7.16 (2H, d, J = 8.3 Hz), 7.20 (2H, d, J = 8.3 Hz), 7.22 (1H, s), 7.51 (1H, s), 7.86 (1H, s), 7.95 (1H, t, J = 4.7 Hz), 8.23 (1H, s). |
| 112 | d6-DMSO | 1.82-2.00 (2H, s, br), 1.98 (3H, s), 2.31 (6H, s), 3.60 (s, 2H), 4.39 (2H, d, J = 5.5 Hz), 5.17 (2H, s), 5.20 (2H, s), 6.95 (2H, s), 7.17 (2H, d, J = 8.3 Hz), 7.22 (s, 1H), 7.25 (2H, d, J = 8.2 Hz), 7.45 (1H, t, J = 5.4 Hz), 7.51 (1H, m), 7.69 (1H, d, J = 1.3 Hz), 7.77 (1H, d, J = 1.3 Hz). |
| 113 | d6-DMSO | 1.91-2.04 (2H, s, br), 1.98 (3H, s), 2.32 (6H, s), 3.60 (2H, s), 4.43 (2H, d, J = 5.3 Hz), 5.21 (2H, s), 5.59 (2H, s), 6.95 (2H, s), 7.18 (2H, d, J = 8.2 Hz), 7.22 (1H, s), 7.28 (2H, d, J = 8.2 Hz), 7.52 (1H, s), 8.29 (1H, t, J = 5.2 Hz), 8.59 (1H, s). |
| 114 | d6-DMSO | 1.98 (3H, s), 2.28 (3H, s), 2.36 (6H, s), 3.93 (2H, d, J = 5.5 Hz), 4.37 (2H, d, J = 5.0 Hz), 5.18 (2H, s), 5.20 (2H, s), 7.09 (2H, s) 7.14-7.20 (4H, m) 7.23 (1H, s), 7.52 (1H, s), 7.86 (1H, t, J = 4.9 Hz), 8.08 (3H, br s), 8.14 (1H, s). |

TABLE 14-continued

NMR data of examples

| Example No | Solvent | Chemical Shift (ppm) |
|---|---|---|
| 115 | d6-DMSO | 1.98 (3H, s), 2.38 (6H, s), 2.43 (3H, s), 3.94 (2H, d, J = 5.8 Hz), 4.40 (2H, d, J = 5.0 Hz), 5.20 (2H, s), 5.27 (2H, s), 7.06-7.09 (4H, m), 7.15-7.18 (2H, m) 7.23 (1H, s), 7.52 (1H, s), 7.89 (1H, s), 7.99 (1H, t, J = 4.9 Hz), 8.08 (2H, br s), 8.14 (1H, s). |
| 116 | d6-DMSO | 1.98 (3H, s), 2.38 (6H, s), 2.43 (3H, s), 3.94 (2H, d, J = 5.8 Hz), 4.40 (2H, d, J = 5.0 Hz), 5.20 (2H, s), 5.27 (2H, s), 7.06-7.09 (4H, m), 7.15-7.18 (2H, m) 7.23 (1H, s), 7.52 (1H, s), 7.89 (1H, s), 7.99 (1H, t, J = 4.9 Hz), 8.08 (2H, br s), 8.14 (1H, s). |
| 117 | d6-DMSO | 1.99 (3H, s), 2.09 (2H, br s), 3.71 (2H, s), 4.36 (2H, d, J = 5.9 Hz), 5.23 (2H, s), 5.41 (2H, s), 7.02 (1H, d, J = 11.2 Hz), 7.08 (1H, d, J = 7.9 Hz), 7.21 (2H, d, J = 8.1 Hz), 7.24 (1H, s), 7.29 (2H, d, J = 8.1 Hz), 7.42 (1H, t, J = 7.9 Hz), 7.54 (1H, s), 8.44 (1H, s), 8.80 (1H, t, J = 5.9 Hz). |
| 118 | d6-DMSO | 1.98 (3H, s), 2.30 (6H, s), 3.61 (2H, s), 4.36 (2H, d, J = 4.7 Hz), 5.21 (2H, s), 5.36 (2H, s), 6.98 (2H, s), 7.17-2.26 (5H, m), 7.53 (1H, s), 8.20 (1H, t, J = 4.6 Hz), 8.38 (1H, s) |
| 119 | d6-DMSO | 1.70-2.20 (2H, br s), 1.99 (3H, s), 2.18 (3H, d, J = 1.6 Hz), 3.71 (2H, s), 4.36 (2H, d, J = 5.2 Hz), 5.23 (2H, s), 5.40 (2H, s), 7.05 (1H, d, J = 8.0 Hz), 7.21-7.29 (6H, m), 7.54 (1H, s), 8.44 (1H, s), 8.65 (1H, t, J = 5.2 Hz). |
| 121 | d6-DMSO | 0.94 (3H, t, J = 7.0 Hz), 1.98 (8H, m), 3.67 (2H, s), 3.92 (2H, s), 4.14 (2H, q, J = 6.9 Hz), 4.33 (2H, d, J = 6.1 Hz), 5.17 (2H, s), 6.68 (1H, s), 7.01 (2H, d, J = 8.2 Hz), 7.11 (2H, d, J = 8.2 Hz), 7.15-7.29 (5H, m), 7.49 (1H, s), 8.34 (1H, t, J = 6.1 Hz). |
| 122 | d6-DMSO | 0.94 (3H, t, J = 7.0 Hz), 1.98 (3H, s), 3.71 (2H, s), 3.92 (2H, s), 4.13 (2H, q, J = 6.9 Hz), 4.33 (2H, d, J = 6.1 Hz), 5.03 (2H, s), 6.21 (1H, td, J = 6.7, 1.4 Hz), 6.39 (1H, d, J = 9.1 Hz), 6.68 (1H, s), 7.02 (2H, d, J = 8.1 Hz), 7.17-7.23 (4H, m), 7.26 (2H, d, J = 8.2 Hz), 7.40 (1H, ddd, J = 8.8, 6.6, 2.1 Hz), 7.70-7.76 (1H, m), 8.35 (1H, t, J = 6.2 Hz). |
| 123 | d6-DMSO | 1.11 (3H, t, J = 6.9 Hz), 2.05 (3H, s), 3.67 (2H, s), 4.10 (2H, s), 4.34 (2H, d, J = 6.1 Hz), 4.40 (2H, q, J = 6.9 Hz), 6.66 (1H, s), 7.15-7.28 (5H, m), 7.44-7.53 (3H, m), 7.86-7.93 (2H, m), 8.34 (1H, t, J = 6.2 Hz). |
| 124 | d6-DMSO | 2.31 (3H, s), 2.36 (6H, s), 2.80 (3H, s), 3.92 (2H, d, J = 5.72 Hz), 4.39 (2H, d, J = 5.0 Hz), 5.46 (2H, s), 7.09 (2H, s), 7.68-7.75 (2H, m), 7.91-7.92 (1H, m), 7.98-8.07 (1H, m), 8.27 (1H, s), 8.37 (3H, s), 8.62 (1H, d, J = 7.56 Hz). |
| 126 | d6-DMSO | 2.36 (6H, s), 2.87 (3H, s), 3.91 (2H, d, J = 5.6 Hz), 4.41 (2H, d, J = 4.8 Hz), 5.68 (2H, s), 7.13 (2H, s), 7.81 (1H, s), 7.86 (1H, d, J = 8.1 Hz), 8.17-8.34 (4H, m), 8.39 (1H, s), 8.53 (1H, s), 8.78 (1H, br, s). |
| 127 | d6-DMSO | 2.37 (6H, s), 2.89 (3H, s), 3.92 (2H, d, J = 5.36 Hz), 4.43 (2H, d, J = 4.9 Hz), 5.80 (2H, s), 7.14 (2H, s), 7.76-7.82 (1H, m), 7.92 (1H, s), 7.99 (1H, s), 8.27 (1H, d, J = 8.1 Hz), 8.37 (3H, s), 8.64 (1H, s), 8.81 (1H, br, s). |
| 128 | d6-DMSO | 2.07 (3H, s), 2.35 (6H, s), 2.41 (3H, s), 2.63 (3H, s), 3.65 (2H, s), 4.35 (2H, d, J = 4.7 Hz), 5.25 (2H, s), 6.35 (1H, s), 6.97 (2H, s), 7.30-7.34 (2H, m), 7.38 (1H, d, J = 8.1 Hz), 7.51 (1H, br s), 7.89 (1H, d, J = 8.1 Hz), 8.15 (1H, d, J = 8.1 Hz). |
| 129 | d6-DMSO | 2.01 (4H, s), 2.37 (6H, s), 3.65-3.72 (4H, m), 3.91 (2H, d, J = 5.6 Hz), 4.41 (2H, d, J = 4.9 Hz), 5.55 (2H, s), 6.55 (1H, d, J = 6.4 Hz), 7.03 (1H, s), 7.16 (2H, s), 7.92 (1H, d, J = 6.5 Hz), 8.42 (2H, s), 8.49 (1H, s), 8.58 (1H, s). |

Biological Methods

The ability of the compounds of formula (I) to inhibit plasma kallikrein may be determined using the following biological assays:

Determination of the $IC_{50}$ for Plasma Kallikrein

Plasma kallikrein inhibitory activity in vitro was determined using standard published methods (see e.g. Johansen et al., Int. J. Tiss. Reac. 1986, 8, 185; Shori et al., Biochem. Pharmacol., 1992, 43, 1209; Stürzebecher et al., Biol. Chem. Hoppe-Seyler, 1992, 373, 1025). Human plasma kallikrein (Protogen) was incubated at 37° C. with the fluorogenic substrate H-DPro-Phe-Arg-AFC and various concentrations of the test compound. Residual enzyme activity (initial rate of reaction) was determined by measuring the change in optical absorbance at 410 nm and the $IC_{50}$ value for the test compound was determined.

Data acquired from these assays are shown in Table 15 below. Generally, but not exclusively, preferred compounds demonstrate an $IC_{50}$ of less than 200 nM.

TABLE 15

| Example No | IC$_{50}$ (human PKal) nM |
|---|---|
| 1 | 63 |
| 2 | 15 |
| 3 | 6 |
| 4 | 121 |
| 8 | 348 |
| 9 | 543 |
| 10 | 571 |
| 11 | 2419 |
| 12 | 5119 |
| 13 | 2383 |
| 14 | 2295 |
| 15 | 5694 |
| 16 | 186 |
| 17 | 492 |
| 18 | 435 |
| 19 | 768 |
| 20 | 4947 |
| 21 | 4522 |
| 22 | 3269 |
| 23 | 1596 |
| 24 | 431 |
| 25 | 1327 |
| 26 | 437 |
| 27 | 848 |
| 28 | 1326 |
| 29 | 140 |
| 30 | 773 |
| 31 | 251 |
| 32 | 732 |
| 33 | 919 |
| 34 | 3599 |
| 35 | 2100 |
| 36 | 203 |
| 37 | 170 |
| 38 | 2311 |
| 39 | 1092 |
| 40 | 1661 |
| 41 | 4704 |
| 42 | 953 |
| 43 | 196 |
| 44 | 355 |
| 45 | 135 |
| 46 | 1164 |
| 47 | 74 |
| 48 | 624 |
| 49 | 89 |
| 50 | 56 |
| 51 | 341 |
| 52 | 475 |
| 53 | 677 |
| 54 | 30 |
| 55 | 3267 |
| 56 | 3856 |
| 57 | 7178 |
| 58 | 4915 |
| 59 | 2742 |
| 60 | 3115 |
| 61 | 2990 |
| 62 | 6034 |
| 63 | 7338 |
| 64 | 6253 |
| 65 | 4558 |
| 66 | 5383 |
| 67 | 3503 |
| 68 | 2093 |
| 69 | 689 |
| 70 | 4593 |
| 71 | 702 |
| 72 | 3021 |
| 73 | 7580 |
| 74 | 1584 |
| 75 | 4499 |
| 76 | 8767 |
| 77 | 3722 |
| 78 | 4133 |
| 79 | 5546 |
| 80 | 2340 |
| 81 | 695 |
| 82 | 488 |
| 83 | 452 |
| 84 | 8379 |
| 85 | 11 |
| 86 | 7 |
| 87 | 5480 |
| 88 | 6989 |
| 89 | 226 |
| 90 | 114 |
| 91 | 29 |
| 92 | 40 |
| 93 | 2845 |
| 94 | 11 |
| 95 | 16 |
| 96 | 63 |
| 97 | 28 |
| 98 | 701 |
| 99 | 38 |
| 100 | 2321 |
| 101 | 4 |
| 102 | 11 |
| 103 | 694 |
| 104 | 30 |
| 105 | 941 |
| 106 | 2 |
| 107 | 3 |
| 108 | 33 |
| 109 | 5 |
| 110 | 2584 |
| 111 | 1 |
| 112 | 2 |
| 113 | 2 |
| 114 | 0.6 |
| 115 | 8 |
| 116 | 11699 |
| 117 | 51 |
| 118 | 1 |
| 119 | 9 |
| 121 | 155 |
| 122 | 151 |
| 123 | 2149 |
| 124 | 2 |
| 125 | 3 |
| 126 | 3 |
| 127 | 731 |
| 128 | 934 |
| 129 | 24 |

Selected compounds were further screened for inhibitory activity against the related enzyme KLK1. The ability of the compounds of formula (I) to inhibit KLK1 may be determined using the following biological assay:

Determination of the IC$_{50}$ for KLK1

KLK1 inhibitory activity in vitro was determined using standard published methods (see e.g. Johansen et al., Int. J. Tiss. Reac. 1986, 8, 185; Shori et al., Biochem. Pharmacol., 1992, 43, 1209; Stürzebecher et al., Biol. Chem. Hoppe-Seyler, 1992, 373, 1025). Human KLK1 (Callbiochem) was incubated at 37° C. with the fluorogenic substrate H-DVal-Leu-Arg-AFC and various concentrations of the test compound. Residual enzyme activity (initial rate of reaction) was determined by measuring the change in optical absorbance at 410 nm and the IC$_{50}$ value for the test compound was determined.

Data acquired from this assay are shown in Table 16 below:

TABLE 16

(KLK1 Activity)

| Example No | IC$_{50}$ (human KLK1) nM |
|---|---|
| 1 | >10,000 |
| 2 | >10,000 |
| 3 | >10,000 |
| 4 | >10,000 |
| 8 | 6360 |
| 9 | >10,000 |
| 10 | >10,000 |
| 11 | >10,000 |
| 12 | >10,000 |
| 13 | >10,000 |
| 14 | 6370 |
| 15 | >10,000 |
| 16 | >10,000 |
| 17 | >10,000 |
| 18 | >10,000 |
| 19 | >10,000 |
| 20 | 2400 |
| 21 | 7500 |
| 22 | >10,000 |
| 23 | >10,000 |
| 24 | >10,000 |
| 25 | >10,000 |
| 26 | >10,000 |
| 27 | >10,000 |
| 28 | >10,000 |
| 29 | >10,000 |
| 30 | >10,000 |
| 31 | 8080 |
| 32 | >10,000 |
| 33 | >10,000 |
| 34 | >10,000 |
| 35 | >10,000 |
| 36 | >10,000 |
| 37 | >10,000 |
| 38 | >10,000 |
| 39 | >10,000 |
| 40 | >10,000 |
| 41 | >10,000 |
| 42 | >10,000 |
| 43 | >10,000 |
| 44 | >10,000 |
| 45 | >10,000 |
| 46 | 4890 |
| 47 | >10,000 |
| 48 | >10,000 |
| 49 | >10,000 |
| 50 | >10,000 |
| 51 | >10,000 |
| 52 | >10,000 |
| 53 | >10,000 |
| 54 | >10,000 |
| 56 | 5480 |
| 57 | >10,000 |
| 58 | >10,000 |
| 59 | >10,000 |
| 60 | >10,000 |
| 61 | >10,000 |
| 62 | >10,000 |
| 63 | >10,000 |
| 64 | >10,000 |
| 65 | >10,000 |
| 66 | 4230 |
| 67 | 6970 |
| 68 | >10,000 |
| 69 | >10,000 |
| 70 | >10,000 |
| 71 | >10,000 |
| 72 | >10,000 |
| 73 | >10,000 |
| 74 | >10,000 |
| 75 | >10,000 |
| 76 | >10,000 |
| 77 | >10,000 |
| 78 | >10,000 |
| 79 | >10,000 |
| 80 | >10,000 |
| 81 | >10,000 |
| 82 | >8660 |
| 83 | >10,000 |
| 84 | >10,000 |
| 85 | >8510 |
| 86 | >10,000 |
| 87 | >10,000 |
| 88 | >10,000 |
| 89 | >10,000 |
| 90 | >10,000 |
| 91 | >10,000 |
| 92 | 10,000 |
| 93 | >10,000 |
| 94 | 10900 |
| 95 | 3900 |
| 96 | >10,000 |
| 97 | >10,000 |
| 98 | >10,000 |
| 99 | >10,000 |
| 100 | >10,000 |
| 101 | 6310 |
| 102 | 4270 |
| 103 | >10000 |
| 104 | >10000 |
| 105 | >10000 |
| 106 | >10000 |
| 107 | >10000 |
| 108 | >10000 |
| 109 | >10000 |
| 110 | >10000 |
| 111 | >10000 |
| 112 | >10000 |
| 113 | >10000 |
| 114 | >10000 |
| 115 | >10000 |
| 116 | >10000 |
| 117 | >10000 |
| 118 | >10000 |
| 119 | >10000 |
| 121 | >10,000 |
| 122 | >10,000 |
| 123 | >10,000 |
| 124 | 301 |
| 125 | 657 |
| 126 | 566 |
| 127 | >10,000 |
| 128 | 2660 |
| 129 | >10,000 |

Selected compounds were further screened for inhibitory activity against the related enzymes plasmin, thrombin, trypsin, Factor Xa and Factor XIIa. The ability of the compounds of formula (I) to these enzymes may be determined using the following biological assays:

Determination of Enzyme Selectivity

Human serine protease enzymes plasmin, thrombin, trypsin, Factor Xa and Factor XIIa were assayed for enzymatic activity using an appropriate fluorogenic substrate. Protease activity was measured by monitoring the accumulation of liberated fluorescence from the substrate over 5 minutes. The linear rate of fluorescence increase per minute was expressed as percentage (%) activity. The Km for the cleavage of each substrate was determined by standard transformation of the Michaelis-Menten equation. The compound inhibitor assays were performed at substrate Km concentration and activities were calculated as the concentration of inhibitor giving 50% inhibition (IC$_{50}$) of the uninhibited enzyme activity (100%).

Data acquired from these assays are shown in Table 17 below:

TABLE 17

(Selectivity data)

| Example No | IC$_{50}$ (nM) | | | |
|---|---|---|---|---|
| | Thrombin | Trypsin | Plasmin | Factor XIIa |
| 1 | >40000 | >40000 | >40000 | >10000 |
| 2 | >40000 | >40000 | 24805 | >10000 |
| 83 | >40000 | 26565 | 27242 | >8510 |
| 84 | >40000 | >40000 | >40000 | >10000 |
| 101 | | | | >10000 |
| 119 | | | | >40000 |
| 124 | | | | >40000 |
| 125 | | | | >40000 |
| 126 | | | | >40000 |
| 127 | | | | >40000 |

Pharmacokinetics

Pharmacokinetic studies of selected examples were performed to assess the pharmacokinetics following a single oral dose in male Sprague-Dawley rats. Typically, either two or three rats were given a single po dose of 5 mL/kg of a nominal 2 mg/mL (10 mg/kg) composition of test compound in either 5% cremophor:5% ethanol:90% phosphate buffered saline or 20% Labrasol:80% water. Following dosing, blood samples were collected over a period of 8 hours. Typical sample times include 5, 15 and 30 minutes then 1, 2, 4, 6 and 8 hours. Following collection, blood samples were centrifuged and the plasma fraction analysed for concentration of test compound by LCMS. Oral exposure data acquired from these studies are shown below:

TABLE 18

(Oral exposure data)

| Example No. | Dose po (mg/kg) | Cmax (ng/mL) | Tmax (mins) |
|---|---|---|---|
| 1 | 11 | 81 | 280 |
| 2 | 11 | 59 | 300 |
| 37 | 10 | 171 | 210 |
| 43 | 8.9 | 71 | 240 |
| 45 | 10 | 228 | 155 |
| 101 | 9.7 | 67 | 300 |

The invention claimed is:

1. A method of treating a disease or condition in which plasma kallikrein activity is implicated, comprising administration to a subject in need thereof a therapeutically effective amount of a compound of formula (I):

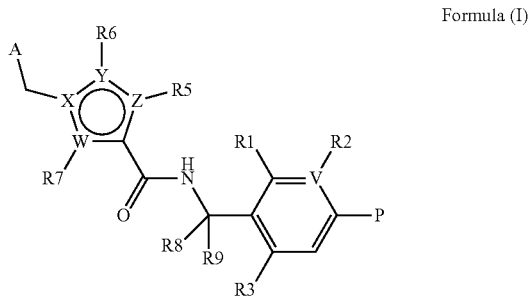

Formula (I)

wherein:
V is C or N such that the aromatic ring containing V is phenyl or pyridine;
R2 is absent when V is N; or, when present, R2 is H, alkyl, alkoxy, CN, halo or CF$_3$;
R1 and R3 are, independently, H, alkyl, alkoxy, CN, halo or CF$_3$;
W, X, Y and Z are, independently, C, N, O, or S, such that the ring containing W, X, Y and Z is a five-membered aromatic heterocycle;
R5, R6 and R7 are, independently, absent, H, alkyl, halo, aryl, heteroaryl, or CF$_3$;
P is —C(R10)(R11)NH$_2$;
R8 and R9 are, independently, H or alkyl, or may together form a cycloalkyl ring;
R10 and R11 are, independently, H or alkyl, or may together form a cycloalkyl ring or a cyclic ether;
A is N-linked morpholine, aryl, or heteroaryl; and wherein alkyl is a linear saturated hydrocarbon having up to 10 carbon atoms (C$_1$-C$_{10}$) or a branched saturated hydrocarbon of between 3 and 10 carbon atoms (C$_3$-C$_{10}$); alkyl is optionally substituted with 1 or 2 substituents which are, independently, (C$_1$-C$_6$)alkoxy, OH, CN, CF$_3$, —COOR12, —CONR12R13, H(CH$_2$)$_{1-3}$CON(R12)(CH$_2$)$_{1-3}$—, fluoro and —NR12R13;
cycloalkyl is a monocyclic saturated hydrocarbon of between 3 and 7 carbon atoms; wherein cycloalkyl is optionally substituted with a substituent which is alkyl, alkoxy or NR12R13;
a cyclic ether is a monocyclic saturated hydrocarbon of between 4 and 7 carbon atoms, wherein one of the ring carbons is replaced by an oxygen atom;
alkoxy is a linear O-linked hydrocarbon of between 1 and 6 carbon atoms (C$_1$-C$_6$) or a branched O-linked hydrocarbon of between 3 and 6 carbon atoms (C$_3$-C$_6$); alkoxy is optionally substituted with 1 or 2 substituents which are, independently, aryl, OH, CN, CF$_3$, —COOR12, —CONR12R13, fluoro, or NR12R13;
aryl is phenyl, biphenyl or naphthyl; aryl may be optionally substituted with 1, 2 or 3 substituents which are, independently, alkyl, alkoxy, OH, halo, CN, -morpholinyl, -piperidinyl, heteroaryl, aryl$^b$, —O-aryl$^b$, —(CH$_2$)$_{1-3}$-aryl$^b$, —(CH$_2$)$_{1-3}$-heteroaryl, —COOR12, —CONR12R13, —(CH$_2$)$_{1-3}$—NR14R15, CF$_3$ and NR12R13;
aryl$^b$ is phenyl, biphenyl or naphthyl, which is optionally substituted with 1, 2 or 3 substituents which are, independently, alkyl, alkoxy, OH, halo, CN, morpholinyl, piperidinyl, —COOR12, —CONR12R13, CF$_3$, or NR12R13;
heteroaryl is a 5, 6, 9 or 10 membered mono- or bi-cyclic aromatic ring, containing, where possible, 1, 2 or 3 ring members which are, independently, N, NR12, S or O; heteroaryl is optionally substituted with 1, 2 or 3 substituents which are, independently, alkyl, alkoxy, OH, halo, CN, morpholinyl, piperidinyl, aryl, —(CH$_2$)$_{1-3}$-aryl, heteroaryl$^b$, —COOR12, —CONR12R13, CF$_3$ or NR12R13;
heteroaryl$^b$ is a 5, 6, 9 or 10 membered mono- or bi-cyclic aromatic ring, containing, where possible, 1, 2 or 3 ring members which are, independently, N, NR12, S or O; wherein heteroaryl$^b$ is optionally substituted with 1, 2 or 3 substituents which are, independently, alkyl, alkoxy, OH, halo, CN, morpholinyl, piperidinyl, aryl, —(CH$_2$)$_{1-3}$-aryl, —COOR12, —CONR12R13, CF$_3$ or NR12R13;
R12 and R13 are, independently, H or alkyl; or R12 and R13 together with the nitrogen to which they are attached form a 4-, 5-, 6- or 7-membered heterocyclic ring which is saturated or unsaturated with 1 or 2 double bonds;

R14 and R15 together with the nitrogen to which they are attached form a 4-, 5-, 6- or 7-membered heterocyclic ring which is saturated or unsaturated with 1 or 2 double bonds, and optionally is oxo substituted;

wherein,
when R5, R6 and R7 are absent or H, then:
either
R10 and R11 together form a cycloalkyl ring or a cyclic ether;
or
A is aryl and aryl is phenyl, biphenyl or naphthyl substituted with 1, 2 or 3 substituents which are, independently, OH, heteroaryl, aryl$^b$, —O-aryl$^b$, —(CH$_2$)$_{1-3}$-aryl$^b$, —(CH$_2$)$_{1-3}$-heteroaryl, —COOR12, —CONR12R13, or —(CH$_2$)$_3$—NR14R15; wherein,
aryl$^b$ is phenyl, biphenyl or naphthyl, wherein aryl$^b$ is substituted with 1, 2 or 3 substituents which are, independently, alkyl, alkoxy, OH, halo, CN, morpholinyl, piperidinyl, —COOR12, —CONR12R13, CF$_3$ or NR12R13; and
heteroaryl is a 5, 6, 9 or 10 membered mono- or bi-cyclic aromatic ring, containing, where possible, 1, 2 or 3 ring members which are, independently, N, NR12, S or O, wherein heteroaryl is substituted with 1, 2 or 3 substituents which are, independently, alkyl, alkoxy, halo, CN, aryl, morpholinyl, piperidinyl, —(CH$_2$)$_{1-3}$-aryl, heteroaryl$^b$, —COOR12, —CONR12R13, CF$_3$ or —NR12R13;
or
A is heteroaryl and heteroaryl is a 5, 6, 9 or 10 membered mono- or bi-cyclic aromatic ring, containing, where possible, 1, 2 or 3 ring members which are, independently, N, NR12, S and O, wherein heteroaryl is substituted with 1, 2 or 3 substituents which are, independently, aryl, —(CH$_2$)$_{1-3}$-aryl, heteroaryl$^b$, —COOR12, or —CONR12R13; wherein,
aryl is phenyl, biphenyl or naphthyl, wherein aryl is substituted with 1, 2 or 3 substituents which are, independently, alkyl, alkoxy, OH, halo, CN, morpholinyl, piperidinyl, heteroaryl, aryl$^b$, —O-aryl$^b$, —(CH$_2$)$_{1-3}$-aryl$^b$, —(CH$_2$)$_{1-3}$-heteroaryl, —COOR12, —CONR12R13, —COR12R13, —(CH$_2$)$_{1-3}$—NR14R15, CF$_3$ or —NR12R13; and
heteroaryl$^b$ is a 5, 6, 9 or 10 membered mono- or bi-cyclic aromatic ring, containing, where possible, 1, 2 or 3 ring members which are, independently, N, NR12, S or O, wherein heteroaryl$^b$ is substituted with 1, 2 or 3 substituents which are, independently, alkyl, alkoxy, halo, CN, morpholinyl, piperidinyl, aryl, —(CH$_2$)$_{1-3}$-aryl, —COOR12, —CONR12R13, CF$_3$ or NR12R13;
or a tautomer, stereoisomer, pharmaceutically acceptable salt or solvate thereof;
wherein the disease or condition in which plasma kallikrein activity is implicated is cerebral haemorrhage, disseminated intravascular coagulation, blood coagulation during cardiopulmonary bypass surgery, or bleeding from post operative surgery.

2. The method of claim 1, wherein at least one of R5, R6 and R7 is alkyl, halo, aryl, heteroaryl or CF$_3$.

3. The method of claim 1, wherein A is:

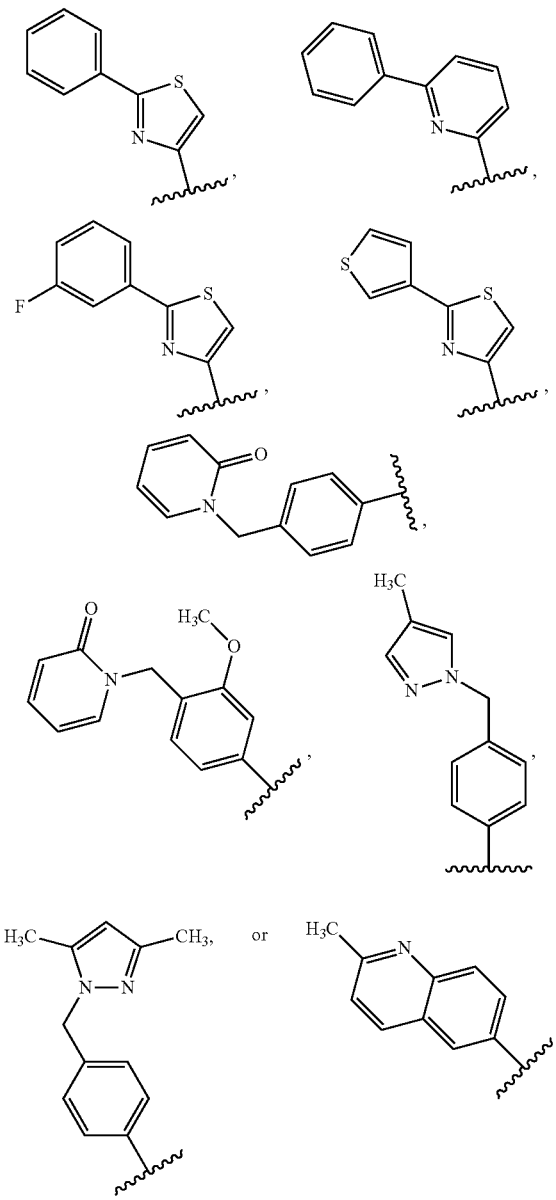

4. The method of claim 1, wherein A is:

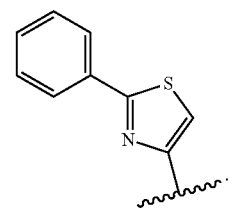 [SMILES: *c1csc(-c2ccccc2)n1]

5. The method of claim 1, wherein R5, R6 and R7 are absent or H; and A is:

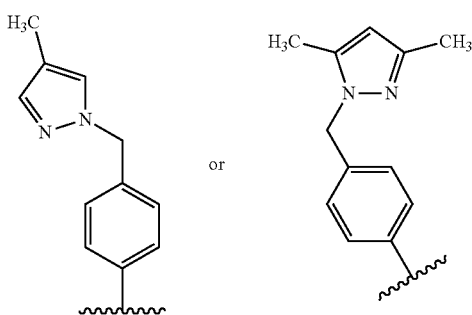

6. The method of claim 1, wherein, X is N and W, Y and Z are C.

7. The method of claim 6, wherein R5 is H, and R6 and R7 are methyl.

8. The method of claim 1, wherein, X and Y are N and W and Z are C.

9. The method of claim 1, wherein, X, Y and Z are N and W is C.

10. The method of claim 1, wherein R8 and R9 are H.

11. The method of claim 1, wherein:
W is C;
X is N;
Y is C;
Z is C;
R5 is H;
R6 and R7 are $CH_3$;
R8 and R9 are H; and
R10 and R11 are both H or together form a cyclopropane ring.

12. The method of claim 1, wherein V is C.

13. The method of claim 1, wherein R1 is alkyl, alkoxy, CN, halo or $CF_3$.

14. The method of claim 1, wherein R1 is alkyl.

15. The method of claim 1, wherein R3 is alkyl.

16. The method of claim 1, wherein the compound of formula (I) is:
2,5-Dimethyl-1-(2-phenyl-thiazol-4-ylmethyl)-1H-pyrrole-3-carboxylic acid 4-aminomethyl-benzylamide;
2,5-Dimethyl-1-(2-phenyl-thiazol-4-ylmethyl)-1H-pyrrole-3-carboxylic acid 4-aminomethyl-2-methyl-benzylamide;
2,5-Dimethyl-1-(2-phenyl-thiazol-4-ylmethyl)-1H-pyrrole-3-carboxylic acid 4-aminomethyl-2,6-dimethyl-benzylamide;
2,5-Dimethyl-1-(2-phenyl-thiazol-4-ylmethyl)-1H-pyrrole-3-carboxylic acid 4-(1-amino-cyclopropyl)-benzylamide;
2,5-Dimethyl-1-(6-phenyl-pyridin-2-ylmethyl)-1H-pyrrole-3-carboxylic acid 4-aminomethyl-benzylamide;
1-[2-(3-Fluoro-phenyl)-thiazol-4-ylmethyl]-2,5-dimethyl-1H-pyrrole-3-carboxylic acid 4-aminomethyl-benzylamide;
2,5-Dimethyl-1-(2-thiophen-3-yl-thiazol-4-ylmethyl)-1H-pyrrole-3-carboxylic acid 4-aminomethyl-benzylamide;
2,5-Dimethyl-1-(2-phenyl-thiazol-4-ylmethyl)-1H-pyrrole-3-carboxylic acid (6-aminomethyl-pyridin-3-ylmethyl)-amide;
2,5-Dimethyl-1-(2-phenyl-thiazol-4-ylmethyl)-1H-pyrrole-3-carboxylic acid 4-aminomethyl-3-fluoro-benzylamide;
2,5-Dimethyl-1-(2-phenyl-thiazol-4-ylmethyl)-1H-pyrrole-3-carboxylic acid 4-aminomethyl-2-fluoro-benzylamide;
2,5-Dimethyl-1-(2-phenyl-thiazol-4-ylmethyl)-1H-pyrrole-3-carboxylic acid 4-aminomethyl-2-chloro-benzylamide;
2,5-Dimethyl-1-(2-phenyl-thiazol-4-ylmethyl)-1H-pyrrole-3-carboxylic acid 4-aminomethyl-2-trifluoromethyl-benzylamide;
2,5-Dimethyl-1-(2-phenyl-thiazol-4-ylmethyl)-1H-pyrrole-3-carboxylic acid 4-aminomethyl-2-methoxy-benzylamide;
1-[4-(4-Methyl-pyrazol-1-ylmethyl)-benzyl]-1H-pyrazole-4-carboxylic acid 4-aminomethyl-benzylamide;
1-[4-(3,5-Dimethyl-pyrazol-1-ylmethyl)-benzyl]-1H-pyrazole-4-carboxylic acid 4-aminomethyl-benzylamide;
2,5-Dimethyl-1-[4-(2-oxo-2H-pyridin-1-ylmethyl)-benzyl]-1H-pyrrole-3-carboxylic acid 4-aminomethyl-benzylamide;
2,5-Dimethyl-1-[4-(2-oxo-2H-pyridin-1-ylmethyl)-benzyl]-1H-pyrrole-3-carboxylic acid 4-aminomethyl-2-methyl-benzylamide;
1-Ethyl-4-methyl-5-[4-(2-oxo-2H-pyridin-1-ylmethyl)-benzyl]-1H-pyrrole-2-carboxylic acid 4-aminomethyl-2-methyl-benzylamide;
2,5-Dimethyl-1-[4-(2-oxo-2H-pyridin-1-ylmethyl)-benzyl]-1H-pyrrole-3-carboxylic acid 4-aminomethyl-2,6-dimethyl-benzylamide;
1-Ethyl-4-methyl-5-[4-(2-oxo-2H-pyridin-1-ylmethyl)-benzyl]-1H-pyrrole-2-carboxylic acid 4-aminomethyl-2,6-dimethyl-benzylamide;
2,5-Dimethyl-1-[4-(4-methyl-pyrazol-1-ylmethyl)-benzyl]-1H-pyrrole-3-carboxylic acid 4-aminomethyl-benzylamide;
2,5-Dimethyl-1-[4-(4-methyl-pyrazol-1-ylmethyl)-benzyl]-1H-pyrrole-3-carboxylic acid 4-aminomethyl-2-methyl-benzylamide;
1-Ethyl-4-methyl-5-[4-(4-methyl-pyrazol-1-ylmethyl)-benzyl]-1H-pyrrole-2-carboxylic acid 4-aminomethyl-2-methyl-benzylamide;
2,5-Dimethyl-1-[4-(4-methyl-pyrazol-1-ylmethyl)-benzyl]-1H-pyrrole-3-carboxylic acid 4-aminomethyl-2,6-dimethyl-benzylamide;
1-Ethyl-4-methyl-5-[4-(4-methyl-pyrazol-1-ylmethyl)-benzyl]-1H-pyrrole-2-carboxylic acid 4-aminomethyl-2,6-dimethyl-benzylamide;
1-[4-(4-Methyl-pyrazol-1-ylmethyl)-benzyl]-1H-imidazole-4-carboxylic acid 4-aminomethyl-benzylamide;
1-[4-(4-Methyl-pyrazol-1-ylmethyl)-benzyl]-1H-pyrazole-4-carboxylic acid 4-aminomethyl-2-methyl-benzylamide;
1-[4-(4-Methyl-pyrazol-1-ylmethyl)-benzyl]-1H-imidazole-4-carboxylic acid 4-aminomethyl-2-methyl-benzylamide;
1-[4-(4-Methyl-pyrazol-1-ylmethyl)-benzyl]-1H-[1,2,3]triazole-4-carboxylic acid 4-aminomethyl-benzylamide;
1-[4-(4-Methyl-pyrazol-1-ylmethyl)-benzyl]-1H-[1,2,3]triazole-4-carboxylic acid 4-aminomethyl-2-methyl-benzylamide;
1-[4-(4-Methyl-pyrazol-1-ylmethyl)-benzyl]-1H-pyrazole-4-carboxylic acid 4-aminomethyl-2,6-dimethyl-benzylamide;
1-[4-(4-Methyl-pyrazol-1-ylmethyl)-benzyl]-1H-imidazole-4-carboxylic acid 4-aminomethyl-2,6-dimethyl-benzylamide;

1-[4-(4-Methyl-pyrazol-1-ylmethyl)-benzyl]-1H-[1,2,3]triazole-4-carboxylic acid 4-aminomethyl-2,6-dimethyl-benzylamide;

1-Ethyl-4-methyl-5-[4-(4-methyl-pyrazol-1-ylmethyl)-benzyl]-1H-pyrrole-2-carboxylic acid 4-aminomethyl-benzylamide;

1-Ethyl-4-methyl-5-[4-(2-oxo-2H-pyridin-1-ylmethyl)-benzyl]-1H-pyrrole-2-carboxylic acid 4-aminomethyl-benzylamide;

5-Methyl-1-[4-(4-methyl-pyrazol-1-ylmethyl)-benzyl]-1H-pyrazole-4-carboxylic acid 4-aminomethyl-2,6-dimethyl-benzylamide;

1-[4-(4-Methyl-pyrazol-1-ylmethyl)-benzyl]-3-trifluoromethyl-1H-pyrazole-4-carboxylic acid 4-aminomethyl-3-fluoro-benzylamide;

1-[4-(4-Methyl-pyrazol-1-ylmethyl)-benzyl]-3-trifluoromethyl-1H-pyrazole-4-carboxylic acid 4-aminomethyl-2,6-dimethyl-benzylamide;

1-[4-(4-Methyl-pyrazol-1-ylmethyl)-benzyl]-3-trifluoromethyl-1H-pyrazole-4-carboxylic acid 4-aminomethyl-3-fluoro-2-methyl-benzylamide;

3-Methyl-1-(2-methyl-quinolin-6-ylmethyl)-1H-pyrazole-4-carboxylic acid 4-aminomethyl-2,6-dimethyl-benzylamide;

5-Methyl-1-(2-methyl-quinolin-6-ylmethyl)-1H-pyrazole-4-carboxylic acid 4-aminomethyl-2,6-dimethyl-benzylamide;

1-(2-Methyl-quinolin-6-ylmethyl)-3-trifluoromethyl-1H-pyrazole-4-carboxylic acid 4-aminomethyl-2,6-dimethyl-benzylamide;

1-(2-Pyrrolidin-1-yl-pyridin-4-ylmethyl)-3-trifluoromethyl-1H-pyrazole-4-carboxylic acid 4-aminomethyl-2,6-dimethyl-benzylamide;

or a pharmaceutically acceptable salt or solvate thereof.

17. The method of claim 1, wherein the disease or condition in which plasma kallikrein activity is implicated is cerebral haemorrhage.

18. The method of claim 1, wherein the disease or condition in which plasma kallikrein activity is implicated is cerebral haemorrhage in hyperglycemic patients.

19. The method of claim 1, wherein the disease or condition in which plasma kallikrein activity is implicated is disseminated intravascular coagulation.

20. The method of claim 1, wherein the disease or condition in which plasma kallikrein activity is implicated is blood coagulation during cardiopulmonary bypass surgery.

21. The method of claim 1, wherein the disease or condition in which plasma kallikrein activity is implicated is bleeding from post-operative surgery.

22. The method of claim 16, wherein the disease or condition in which plasma kallikrein activity is implicated is cerebral haemorrhage.

23. The method of claim 16, wherein the disease or condition in which plasma kallikrein activity is implicated is cerebral haemorrhage in hyperglycemic patients.

24. The method of claim 16, wherein the disease or condition in which plasma kallikrein activity is implicated is disseminated intravascular coagulation.

25. The method of claim 16, wherein the disease or condition in which plasma kallikrein activity is implicated is blood coagulation during cardiopulmonary bypass surgery.

26. The method of claim 16, wherein the disease or condition in which plasma kallikrein activity is implicated is bleeding from post-operative surgery.

* * * * *